US011180521B2

(12) United States Patent
Kremsky et al.

(10) Patent No.: US 11,180,521 B2
(45) Date of Patent: Nov. 23, 2021

(54) NICOTINAMIDE RIBOSIDE ANALOGS, PHARMACEUTICAL COMPOSITIONS, AND USES THEREOF

(71) Applicants: Metro International Biotech, LLC, Birmingham, MI (US); NewSouth Innovations Pty Ltd, Sydney (AU)

(72) Inventors: Jonathan N. Kremsky, Arlington, MA (US); Bruce Szczepankiewicz, Hopkinton, MA (US); Hamish Toop, Sydney (AU); Jonathan Morris, Sydney (AU)

(73) Assignees: Metro International Biotech, LLC, Cambridge, MA (US); NewSouth Innovations Pty Ltd, Sydney (AU)

( * ) Notice: Subject to any disclaimer, the term of this patent is extended or adjusted under 35 U.S.C. 154(b) by 0 days.

(21) Appl. No.: 16/965,747

(22) PCT Filed: Jan. 29, 2019

(86) PCT No.: PCT/US2019/015672
§ 371 (c)(1),
(2) Date: Jul. 29, 2020

(87) PCT Pub. No.: WO2019/152416
PCT Pub. Date: Aug. 8, 2019

(65) Prior Publication Data
US 2021/0032280 A1  Feb. 4, 2021

Related U.S. Application Data

(60) Provisional application No. 62/623,579, filed on Jan. 30, 2018.

(51) Int. Cl.
*C07H 19/048* (2006.01)

(52) U.S. Cl.
CPC .................. *C07H 19/048* (2013.01)

(58) Field of Classification Search
None
See application file for complete search history.

(56) References Cited

U.S. PATENT DOCUMENTS

| | | |
|---|---|---|
| 3,201,389 A | 8/1965 | Fujimoto et al. |
| 3,451,997 A | 6/1969 | Fujimoto et al. |
| 4,411,995 A | 10/1983 | Whitesides et al. |
| 7,560,442 B2 | 7/2009 | Susilo |
| 7,776,326 B2 | 8/2010 | Milbrandt et al. |
| 7,977,049 B2 | 7/2011 | Sinclair et al. |
| 8,481,711 B2 | 7/2013 | Kaminishi et al. |
| 9,169,209 B2 | 10/2015 | Bair et al. |
| 9,295,688 B2 | 3/2016 | Milbrandt et al. |
| 9,458,172 B2 | 10/2016 | Bair et al. |
| 9,676,721 B2 | 6/2017 | Bair et al. |
| 9,822,129 B2 | 11/2017 | Bair et al. |
| 9,855,289 B2 | 1/2018 | Normington et al. |
| 9,861,651 B2 | 1/2018 | Brown et al. |
| 9,919,003 B2 | 3/2018 | Normington et al. |
| 9,975,915 B1 | 5/2018 | Migaud et al. |
| 10,000,519 B2 | 6/2018 | Migaud et al. |
| 10,214,552 B2 | 2/2019 | Fu et al. |
| 10,233,208 B1 | 3/2019 | Carr et al. |
| 10,392,415 B2 | 8/2019 | Livingston et al. |
| 10,392,416 B2 | 8/2019 | Livingston et al. |
| 10,548,913 B2 | 2/2020 | Normington et al. |
| 10,618,927 B1 | 4/2020 | Szczepankiewicz et al. |
| 11,059,847 B2 | 7/2021 | Livingston et al. |
| 2012/0107888 A1 | 5/2012 | Schmalisch et al. |
| 2012/0328526 A1 | 12/2012 | Kristian |
| 2013/0102771 A1 | 4/2013 | Kaminishi et al. |
| 2013/0273034 A1 | 10/2013 | Bair et al. |
| 2013/0295051 A1 | 11/2013 | Bair et al. |
| 2014/0275057 A1 | 9/2014 | Bair et al. |
| 2014/0294805 A1 | 10/2014 | Bair et al. |
| 2015/0104384 A1 | 4/2015 | Bair et al. |
| 2015/0132280 A1 | 5/2015 | Lopez et al. |
| 2015/0175621 A1 | 6/2015 | Bair et al. |
| 2015/0258052 A1 | 9/2015 | Evans et al. |
| 2016/0002266 A1 | 1/2016 | Bair et al. |

(Continued)

FOREIGN PATENT DOCUMENTS

| | | |
|---|---|---|
| CN | 101497638 A | 8/2009 |
| CN | 101601679 B | 8/2011 |

(Continued)

OTHER PUBLICATIONS

International Search Report and Written Opinion for International Application No. PCT/US2019/015672 dated May 15, 2019.
Riemschneider et al., "Zur Beeinflussung von Stoffwechselvorgangcn durch unphysiologische Verbindungen, IV: Nicotinylaminosaureester und Nucleosid-Deritvate," Insect repellent science, 41(3):99-106 (1976).
"Cardiac Medications," Heart.org, http://www.heart.org/en/health-topics/heart-attack/treatment-of-a-heart-attack/cardiac-medications (2015).
"Diabetes Treatment," Drugs.com, https://www.drugs.com/diabetes-treatment.html (2018).
"Medications for Dermatitis," Drugs.com, https://www.drugs.com/condition/dermatitis.html (2018).
"Medications for Obesity," Drugs.com, https://www.drugs.com/condition/obesity.html (2018).

(Continued)

*Primary Examiner* — Traviss C McIntosh, III
(74) *Attorney, Agent, or Firm* — David P. Halstead; Foley Hoag LLP

(57) ABSTRACT

Provided herein are compounds of Formula (I) and their salts, and compositions comprising such compounds that are useful for increasing the amount of NAD⁺ in cells. Also disclosed are methods of using the disclosed compounds and compositions for treating, for example, diseases or disorders related to aging or stress, diabetes, obesity, mitochondrial diseases, neurodegenerative diseases, cardiovascular disease, blood clotting disorders, inflammation, cancer, and/or flushing.

19 Claims, 2 Drawing Sheets

(56) References Cited

U.S. PATENT DOCUMENTS

| | | | |
|---|---|---|---|
| 2016/0168184 A1 | 6/2016 | Migaud et al. | |
| 2016/0287621 A1 | 10/2016 | Sinclair et al. | |
| 2016/0333041 A1 | 11/2016 | Fu et al. | |
| 2016/0355514 A1 | 12/2016 | Bair et al. | |
| 2016/0355539 A1 | 12/2016 | Migaud et al. | |
| 2017/0066724 A1 | 3/2017 | Evans et al. | |
| 2017/0182076 A1 | 6/2017 | Alvarez et al. | |
| 2017/0204131 A1 | 7/2017 | Szczepankiewicz et al. | |
| 2017/0210774 A1 | 7/2017 | Carlson et al. | |
| 2017/0216262 A1 | 8/2017 | Bair et al. | |
| 2017/0267709 A1* | 9/2017 | Migaud | C07H 19/048 |
| 2017/0304338 A1 | 10/2017 | Dellinger et al. | |
| 2017/0368039 A1 | 12/2017 | Kenneth et al. | |
| 2018/0030079 A1 | 2/2018 | Carlson et al. | |
| 2018/0051253 A1 | 2/2018 | Chen | |
| 2018/0086783 A1 | 3/2018 | Carlson et al. | |
| 2018/0104248 A1 | 4/2018 | Lopez et al. | |
| 2018/0134743 A1 | 5/2018 | Migaud et al. | |
| 2018/0147227 A1 | 5/2018 | Normington et al. | |
| 2018/0162895 A1 | 6/2018 | Fu et al. | |
| 2018/0186824 A1 | 7/2018 | Migaud et al. | |
| 2018/0228824 A1 | 8/2018 | Yoshino et al. | |
| 2020/0157136 A1 | 5/2020 | Livingston et al. | |
| 2020/0352966 A1 | 11/2020 | Normington et al. | |
| 2021/0030908 A1 | 2/2021 | Mason | |

FOREIGN PATENT DOCUMENTS

| | | |
|---|---|---|
| CN | 102876759 A | 1/2013 |
| CN | 104367587 B | 6/2018 |
| WO | WO-2010/135520 A1 | 11/2010 |
| WO | WO-2012004917 A1 | 1/2012 |
| WO | WO-2012031196 A1 | 3/2012 |
| WO | WO-2012031197 A1 | 3/2012 |
| WO | WO-2012031199 A1 | 3/2012 |
| WO | WO-2012/094343 A1 | 7/2012 |
| WO | WO-2012/150952 A1 | 11/2012 |
| WO | WO-2013/085555 A2 | 6/2013 |
| WO | WO-2013127266 A1 | 9/2013 |
| WO | WO-2013127267 A1 | 9/2013 |
| WO | WO-2013127268 A1 | 9/2013 |
| WO | WO-2013127269 A1 | 9/2013 |
| WO | WO-2013130943 A1 | 9/2013 |
| WO | WO-2014/074715 A1 | 5/2014 |
| WO | WO-2014/111906 A1 | 7/2014 |
| WO | WO-2014/146044 A1 | 9/2014 |
| WO | WO-2015/014722 A1 | 2/2015 |
| WO | WO-2015/069860 A1 | 5/2015 |
| WO | WO-2015073576 A1 | 5/2015 |
| WO | WO-2015/138969 A1 | 9/2015 |
| WO | WO-2015/186068 A1 | 12/2015 |
| WO | WO-2016014927 A2 | 1/2016 |
| WO | WO-2016086860 A1 | 6/2016 |
| WO | WO-2016/144660 A1 | 9/2016 |
| WO | WO-2016196941 A1 | 12/2016 |
| WO | WO-2017022768 A1 | 2/2017 |
| WO | WO-2017/059249 A1 | 4/2017 |
| WO | WO-2017/062311 A | 4/2017 |
| WO | WO-2017/079195 A1 | 5/2017 |
| WO | WO-2017110317 A1 | 6/2017 |
| WO | WO-2017/114796 A1 | 7/2017 |
| WO | WO-2017145151 A1 | 8/2017 |
| WO | WO-2017185549 A1 | 11/2017 |
| WO | WO-2017/218580 A1 | 12/2017 |
| WO | WO-2018023205 A1 | 2/2018 |
| WO | WO-2018023207 A1 | 2/2018 |
| WO | WO-2018023208 A1 | 2/2018 |
| WO | WO-2018023209 A1 | 2/2018 |
| WO | WO-2018023210 A1 | 2/2018 |
| WO | WO-2018/047715 A1 | 3/2018 |
| WO | WO-2018/047716 A1 | 3/2018 |
| WO | WO-2018/052019 A1 | 3/2018 |
| WO | WO-2018/052020 A1 | 3/2018 |
| WO | WO-2018/089830 A1 | 5/2018 |
| WO | WO-2018/132833 A1 | 7/2018 |
| WO | WO-2018120069 A1 | 7/2018 |
| WO | WO-2018/143258 A1 | 8/2018 |
| WO | WO-2019/152416 A1 | 8/2019 |
| WO | WO-2020/197882 A1 | 10/2020 |

OTHER PUBLICATIONS

"Medications for Peripheral Neuropathy," Drugs.com, https://www.drugs.com/condition/peripheral-neuropathy.html (2018).

"Medications for Thrombotic/Thromboembolic Disorder," Drugs.com, https://www.drugs.com/condition/thrombotic-thromboembolic-disorder.html (2018).

"Sleep Disorders: Medications for Circadian Rhythm Disorders," WebMD, https://www.webmd.com/sleep-disorders/circadian-rhythm-disorder-medications#1 (2018).

"Wound Care Medications," GoodRx.com, https://www.goodrx.com/wound-care/drugs (2018).

Ahmadibeni et al., "Solid-Phase Synthesis of Symmetrical 5',5'-Dinucleoside Mono-, Di-, Tri-, and Tetraphosphodiesters," Organic Letters, 9(22): 4483-4486 (2007).

Anastasi et al., "New antiviral nucleoside prodrugs await application," Current medicinal chemistry, 10(18):1825-1843 (2003).

Asher et al., "SIRT1 Regulates Circadian Clock Gene Expression through PER2 Deacetylation," Cell, 134:317 (2008).

Atkinson et al., "Nicotinamide 6-Mercaptopurine Dinucleotide and Related Compounds: Potential Sources of 6-Mercaptopurine Nucleotide in Chemotherapy," Nature, 196: 35-36 (1962).

Barnea et al., "High-Fat Diet Delays and Fasting Advances the Circadian Expression of Adiponectin Signaling Components in Mouse Liver," Endicrinology 150:161 (2009).

Bauer, "Polymorphism—A Critical Consideration in Pharmaceutical Development, Manufacturing, and Stability," Journal of Validation of Technology, 14(5):15-23 (2008).

Bazzanini et al., "Synthetic approaches to a mononucleotide prodrug of cytarabine," Nucleosides, Nucleotides, and Nucleic Acids, 24(10-12):1635-1649 (2005).

Belenky et al., "Nicotinamide riboside promotes Sir2 silencing and extends lifespan via Nrk and Urh1/Pnp1/Meu1 pathways to NAD+," Cell,129(3):473-484 (2007).

Berghaeuser et al., "A Simple Preparation of an Enzyme Reactor Producing Nicotinamidemononucleotide," Biotechnology Letters, 3(7): 339-344 (1981).

Bobeck et al., "Advances in nucleoside monophosphate prodrugs as anti-HCV agents," Antiviral Therapy—An Official Publication of the International Society for Antiviral Research, 15(7):935-950 (2010).

Bordone et al., "Calorie restriction, SIRT1 and metabolism: understanding longevity," Nat Rev Mol Cell Biol, 6:298-305 (2005).

Borradaile et al., "NAD+, Sirtuins, and Cardiovascular Disease," Current Pharmaceutical Design, 15(1):110-117 (2016).

Brittain et al., "X-Ray Diffraction of Pharmaceutical Materials," Profiles of Drug Substances, Excipients, and Related Methodology, 30:273-319 (2003).

Byrn et al., "Pharmaceutical solids: a strategic approach to regulatory considerations," Pharmaceut Res, 12(7):945-954 (1995).

Caira, "Crystalline Polymorphism of Organic Compounds," Topics in Current Chemistry, 198:163-208 (1998).

CAS Registry No. 108273-23-0 (1987).
CAS Registry No. 108489-22-1 (1987).
CAS Registry No. 1094-61-7 (1984).
CAS Registry No. 150035-58-8 (1993).
CAS Registry No. 906748-40-1 (2006).

Cayman Chemical, "beta-Nicotinamide mononucleotide," Item No. 16411 Product Information (2014).

Cherney, "Osteoarthritis Medications List," Healthline, https://www.healthline.com/health/osteoarthritis/medications-list#nsaids (2016).

Congiatu et al., "Novel potential anticancer naphthyl phosphoramidates of BVdU: separation of diastereoisomers and assignment of the absolute configuration of the phosphorus center," Journal of medicinal chemistry, 49(2): 452-455 (2006).

Corda et al., "Functional aspects of protein mono-ADP-ribosylation," EMBO J, 22(9):1953-1958 (2003).

(56) References Cited

OTHER PUBLICATIONS

Cross et al., "Rules for the Nomenclature of Organic Chemistry. Section E: Sterohemistry," Pure Appl Chem, 45(1):11-30, (1976).
Database Registry Chemical Abstracts, Database Accession No. 807266-77-9, CAS Registry No. 807266-77-9 (Jan. 2, 2005).
Dekker, Polymorphism in Pharmaceutical Solids, First Ed, pp. 184-208 (1999).
Dekker, Polymorphism in Pharmaceutical Solids, First Ed, pp. 7-8 (1999).
Dowden et al., "Chemical Synthesis of the Novel CA 2+ Messenger NAADP," Nucleosides, Nucleotides and Nucleic Acids, 24(5-7):513-518 (2005).
Extended European Search Report for EP Application No. 16833957.0 dated Dec. 21, 2018.
Extended European Search Report received for EP Patent Application No. EP 16852711, dated Feb. 11, 2019.
Fang et al., "Defective Mitophagy in XPA via PARP-1 Hyperactivation and NAD+/SIRT1 Reduction," Cell, 157(4):882-896 (2014).
Garten et al., "Nampt: Linking NAD biology, metabolism, and cancer," Trends Endocrinol Metab, 20(3):130-138 (2009).
Gavande et al., "DNA repair targeted therapy: The past or future of cancer treatment?," Pharmacology & Therapeutics, 160:65-83 (2016).
Gockel et al., "Synthesis of an oligonucleotide with a nicotinamide mononucleotide residue and its molecular recognition in DNA helices," Organic & Biomolecular Chemistry, 13(41):10303-10309 (2015).
Gomes et al., "Declining NAD+ Induces a Pseudohypoxic State Disrupting Nuclear-Mitochondrial Communication druing Aging," Cell, 155(7):1624-1638 (2013).
Guest et al., "Changes in Oxidative Damage, Inflammation and [NAD(H)] with Age in Cerebrospinal Fluid," PLOS One, 9(1):e85335 (2014).
Harrison et al., "Inhibition of Platelet Aggregation and the Platelet Release Reaction By alpha, omega Diadenosine polyphosphates," FEBS Letts 54(1):57-60 (1975).
Hecker et al., "Prodrugs of Phosphates and Phosphonates," Journal of Medicinal Chemistry, 51(8):2328-2345 (2008).
Hirayama, Yuukikagoubutsu Kessyo sakusei Handbook—Genri to Know-how—(Handbook for Preparation of Crystals of Organic Compounds—Principle and Know-how-), Maruzen Co. Ltd., pp. 37-84 (2008).
Imai et al., "NAD+ and sirtuins in aging and disease," Trends in Cell Biol, 24(8):464-471 (2014).
Imai et al., "Transcriptional silencing and longevity protein Sir2 is an NAD-dependent histone deacetylase," Nature, 403:795-800 (2000).
International Search Report and Written Opinion for International Application No. PCT/US2016/045855 dated Nov. 14, 2016.
International Search Report and Written Opinion for International Application No. PCT/US2016/054776 dated Jan. 25, 2017.
International Search Report and Written Opinion for International Application No. PCT/US2020/023318 dated Jun. 24, 2020.
Kohsaka et al., "high-Fat Diet Disrupts Behavioral and Molecular Circadian Rhythms in Mice," Cell Metab, 6:414 (2007).
Lee et al., "A Chemical Synthesis of Nicotinamide Adenine Dinucleotide (NAD+)," Chemical Communications (Cambridge), 8: 729-730 (1999).
Lee, "A practical guide to pharmaceutical polymorph screening & selection," Asian Journal of Pharmaceutical Science 9(4):163-175 (2014).
Lin et al., "Nicotinamide adenine dinucleotide, a metabolic regulator of transcription, longevity and disease," Curr Opin Cell Biol, 15:241-246 (2003).
Liu et al., "A Novel Preparation of Nicotinamide Mononucleotide," Nucleosides & Nucleotides, 13(5): 1215-1216 (1994).
Liu et al., "Enzymatic synthesis of polymers containing nicotinamide mononucleotide," Nucleic Acids Research, 23(18):3742 (1995).
Liu et al., "Synthesis of Phosphodiester-type Nicotinamide Adenine Dinucleotide Analogs," Tetrahedron, 65(40): 8378-8383 (2009).
Makarov et al., "Syntheses and chemical properties of β-nicotinamide riboside and its analogues and derivatives," Beilstein J Org Chem 15:401-430 (2019).
Menissier de Murcia et al., "Functional Interaction between PARP-1 and PARP-2 in chromosome stability and embryonic development in mouse," EMBO J, 22(9):2255-2263 (2003).
Migaud et al., "Probing Aplysia californica Adenosine 5'-Diphosphate Ribosyl Cyclase for Substrate Binding Requirements: Design of Potent Inhibitors," Biochemistry, 38:9105-9114 (1999).
Mikhailopulo et al., "Synthesis of glycosides of nicotinamide and nicotinamide mononucleotide," Synthesis, 5:388-389 (1981).
Moazed, "Enzymatic activities of Sir2 and chromatin silencing," Curr Opin Cell Biol, 13(2):232-238 (2001).
Montgomery et al., "Synthesis of Potential Anticancer Agents. XXVIII. Simple Esters of 6-Mercaptopurine Ribonucleotide2," The Journal of Organic Chemistry, 26(6):1929-1933 (1961).
Moynihan et al., "Increased dosage of mammalian Sir2 in pancreatic ß cells enhances glucose-stimulated insulin secretion in mice," Cell Metab, 2:105-117 (2005).
Nakahata et al., "The NAD+-Dependent Deacetylase SIRT1 Modulates CLOCK-Mediated Chromatin Remodeling and circadian Control," Cell, 134(2):329 (2008).
Nakai et al., Shin Seizaigaku (New Pharmacy), Nanzando Co. Ltd., 1st Edition, 2nd Printing, pp. 102-104, 217-236 (1984).
Park et al., "Nicotinamide Ribose 5'-0-[S-(3-Bromo-2-oxopropyl)] thiophosphate: A New Affinity Label for NMN Sites in Enzymes," Archives of Biochemistry and Biophysics, 303(2):483-488 (1993).
Pertusati et al., "Medicinal chemistry of nucleoside phosphonate prodrugs for antiviral therapy," Antivir Chem Chemother, 22(5):181-203 (2012).
Pfleiderer et al., "Zum Wirkungsmechanismus von Dehydrogenasen V. Uber die Bedeutung des Adenosindiphosphatrestes im Nicotinamid-Adenin-Dinucleotid," Biochimica et Biophysica Acta, 73:39-49 (1963).
Pfleiderer et al., "Zum Wirkungsmechanismus von Dehydrogenasen. Das Reaktionsverhalten von Pyridinnucleotiden (PN) und PN-Modellen mit Sulfit als nucleophilem Agens," Chemische Berichte, 93(12):3083-3099 (1960).
Picard et al., "Sirt1 promotes fat mobilization in white adipocytes by repressing PPAR-y," Nature, 429:771-776 (2004).
Preitner et al., "The Orphan Nuclear Receptor REV-ERBa Controls Circadian Transcription within the Positive Limb of the Mammalian circadian Oscillator," Cell, 110:251 (2002).
Rajman et al., "Therapeutic Potential of NAD-Boosting Molecules: The In Vivo Evidence," Cell Metabolism, 27(3): 529-547 (2018).
Ramsey et al., "Cicadian clock feedback cycle through NAMPT-mediated NAD+ biosynthesis," Science, 324(5927):651-654 (2009).
Redpath et al., "Nicotinamide Benzimidazolide Dinucleotides Non-Cyclisable Analogues of NAD+," Synlett, 25:2331-2336 (2014).
Rodionova et al., "Metabolic and bactericidal effects of targeted suppression of NadD and NadE enzymes in mycobacteria," mBio, 5(1):e00747-13 (2014).
Roskar et al., "Analytical Methods for Quantification of Drug Metabolites in Biological Samples," IntechOpen, Chapter 4:79-126 (2012).
Rudic et al., "BMAL1 and CLOCK, Two Essential Components of the Circadian Clock, Are Involved in Glucose Homeostasis," PLoS Biol, 2:e377 (2004).
Rutter et al., "Regulation of Clock and NPAS2 DNA Binding by the Redox State of NAD Cofactors," Science, 293(5529):510 (2001).
Sarma et al., "Investigations of Inter- and Intramolecular Interactions in Flavin-Adenine Dinucleotide by Proton Magnetic Resonance," Biochemistry, 7(12):4359-4367 (1968).
Sato et al., "A Functional Genomics Strategy Reveals Rora as a Component of the Mammalian Circadian Clock," Neuron, 43:527 (2004).
Sharma et al., "X-ray diffraction: a powerful method of characterizing nanomaterials," Recent Research in Science and Technology, 4:77-79 (2012).
Shioji, Kokei Seizai no Seizo Gijutsu (Manufacture Technology of Solid Tablet), CMC Publishing Co. Ltd., Popular Edition, 1st Printing, pp. 9-14 (2003).

(56) References Cited

OTHER PUBLICATIONS

Smith et al., "A phylogenetically conserved NAD+-dependent protein decetylase activity in the Sir2 protein family," Proc Natl Acad Sci, 97(12):6658-6663 (2000).

Soto-Gamez et al., "Therapeytic interventions for aging: the case of cellular senescence," Drug Discovery Today, 22(5):786-795 (2017).

Stein et al., "Expression of nampt in hippocampal and cortical excitatory neurons is critical for cognitive function," J Neurosci, 34(17): 5800-5815 (2014).

Stein et al., "Scientific ablation on Nampt in adult neural stem cells recapitulates their functional defects during aging," EMBO J, 33(12):1321-1340 (2014).

Stieger et al., "7:Recrystallization of Active Pharmaceutical Ingredients," Crystallization—Science and Technology, 183-204 (2012).

Takahashi et al., "The Genetics of Mammalian Circadian Order and Disorder: Implications for Physiology and Disease," Nat Rev Genet, 9(10):764 (2008).

The Chemical Society of Japan Ed., 4th Edition Jikken Kagaku Kouza 1 Kihon Sousa I (4th Edition Experimental Chemistry 1 Basic Operation I), Maruzen Co. Ltd., 2nd Printing, pp. 184-186 (1996).

Thorpe et al., "Lipoamide Dehydrogenase from Pig Heart. Pyridine Nucleotide Induced Changes in Monoalkylated Two-Electron Reduced Enzyme," Biochemistry, 20:1507-1513 (1981).

Turek et al., "Obesity and Metabolic Syndrome in Circadian Clock Mutant Mice," Science, 308:1043 (2005).

United States Department of Health and Human Services. "Guidance for Industry Pyrogen and Endotoxin Testing: Questions and Answers," pp. 1-10 (2012).

United States Pharmacopeia General Chapter <151> Pyrogen Test, 2 pages.

Walt et al., "An Efficient Chemical and Enzymatic Synthesis of Nicotinamide Adenine Dinucleotide (NAD+)," Journal of the American Chemical Society, 106(1): 234-239 (1984).

Wang et al., "A local mechanism mediates NAD-dependent protection of axon degeneration," J Cell Biol, 170(3):349-355 (2005).

Wiemer et al., "Prodrugs of Phosphnates and Phosphates: Crossing the Membrane Barrier," Topics in Current Chemistry, 360:115-160 (2014).

Woenckhaus, "Synthesen und biochemische Eigenschaften wassertoffubertragender Coenzye modelle," Chemische Berichte, 97(9):2439-2446 (1964).

Yang et al., "NAD+-dependent Deacetylase SIRT3 Regulates Mitochondrial Protein Synthesis by Deacetylation of the Ribosomal Protein MRPL10," J Biol Chem, 285: 7417-7429 (2010).

Yoshino et al., "Nicotinamide Mononucleotide, a Key NAD+ Intermediate, Treats the Pathology of Diet- and Age-Induced Diabetes in Mice," Cell Metab, 14(4): 528-536 (2011).

ß-Nicotinamide Mononucleotide, Item No. 16411 Safety Data Sheet, Cayman Chemical (2015).

\* cited by examiner

NICOTINAMIDE RIBOSIDE ANALOGS, PHARMACEUTICAL COMPOSITIONS, AND USES THEREOF

RELATED APPLICATION

This application is a 371(c) national stage of PCT/US2019/015672, filed Jan. 29, 2019, which claims the benefit of priority to U.S. Provisional Patent Application Ser. No. 62/623,579, filed Jan. 30, 2018, the contents of each of which is incorporated by reference herein in their entirety.

BACKGROUND

Nicotinamide adenine dinucleotide ($NAD^+$) is a natural coenzyme that functions as an intermediary in cellular oxidation and reduction reactions as well as an ADP-ribosyltransferase substrate. Altering intracellular $NAD^+$ levels can improve the health of a cell, but introduction of compounds that enter $NAD^+$ metabolic pathways can also prove toxic to cells. For example, benzamide riboside (BR) is a well-known antitumor agent. BR is a prodrug that can be phosphorylated to its 5'-monophosphate and then converted to its active metabolite benzamide adenine dinucleotide (BAD). That metabolite is an active analogue of $NAD^+$ and an inhibitor of inosine 5'-monophosphate dehydrogenase (IMPHD). IMPHD is linked to malignant transformations. The central nervous system and leukemic cell lines are sensitive to BR. However, BAD also inhibits other dehydrogenases, such as malate dehydrogenase and glutamic acid dehydrogenase, which can induce undesirable side effects. Thus, there is a need to identify compounds and compositions that are capable of altering intracellular $NAD^+$ levels of damaged or diseased cells, preferably by, without causing unacceptable side effects.

SUMMARY

Provided herein are compounds and compositions useful for increasing the amount of $NAD^+$ in cells. Also disclosed are methods of using the disclosed compounds and compositions for treating cell death, cell dysfunction, or aging; insulin resistance, a metabolic syndrome, hypercholesterolemia, atherogenic dyslipidemia, diabetes, or complications thereof; neurological or neurodegenerative disorders; and mitochondrial-related diseases and conditions; or for increasing insulin sensitivity.

Provided herein are compounds having a structure of Formula (I):

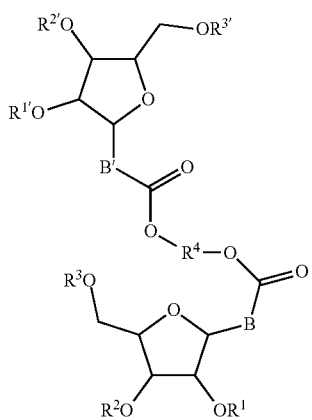

or a pharmaceutically acceptable salt thereof, wherein:
B and B' are each independently

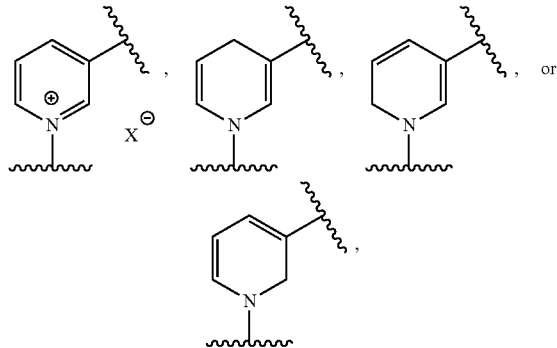

e.g., wherein the nitrogen is bound to the tetrahydrofuran ring;
$X^-$ is a counteranion, such as $Cl^-$, $OH^-$, $SO_4H^-$, $PO_4H^{2-}$, $CH_3COO^-$, $CF_3COO^-$, $PF_6^-$, $CH_3SO_3^-$, $CF_3SO_3^-$, and $PhCO_2^-$;
$R^1$, $R^2$, $R^3$, $R^{1'}$, $R^{2'}$, and $R^{3'}$ are each independently hydrogen, substituted or unsubstituted alkyl, or substituted or unsubstituted —C(O)-alkyl; and
$R^4$ is alkylene, alkenylene, alkynylene, cycloalkylene, cycloalkenylene, heteroalkylene, arylene, aralkylene, heterocyclylene, heteroarylene, or heteroaralkylene, each of which may be substituted or unsubstituted; and
$R^a$ is hydrogen or alkyl.

In certain embodiments, the alkylene group, the alkenylene group, the alkynylene group, the cycloalkylene group, the cycloalkenylene group, the heteroalkylene group, the arylene group, the aralkylene group, the heterocyclylene group, the heteroarylene group, or the heteroaralkylene group of $R^4$ is substituted with one or more substituents selected from halo, OH, $NO_2$, CN, alkyl, alkoxy, alkenyl, alkynyl, —C(O)-alkyl, —C(O)-aryl, —C(O)— heteroaryl, —OC(O)-alkyl, —OC(O)-aryl, —OC(O)-heteroaryl, —$NR^a$C(O)-alkyl, —$NR^a$C(O)-aryl, —$NR^a$C(O)-heteroaryl, cycloalkyl, cycloalkenyl, aryl, and heteroaryl.

In other embodiments, $R^4$ is unsubstituted alkylene, unsubstituted alkylene-, unsubstituted alkenylene, unsubstituted alkynylene, unsubstituted cycloalkylene, unsubstituted cycloalkenylene, unsubstituted heteroalkylene, unsubstituted arylene, unsubstituted aralkylene, unsubstituted heterocyclylene, unsubstituted heteroarylene, or unsubstituted heteroaralkylene.

In still other embodiments, $R^4$ is $C_1$-$C_6$-alkylene, $C_2$-$C_6$-alkenylene, $C_2$-$C_6$-alkynylene, $C_3$-$C_6$-cycloalkylene, $C_3$-$C_6$-cycloalkenylene, arylene, heterocyclylene, heteroarylene, or heteroaryl-$C_2$-$C_6$-alkylene, each of which is unsubstituted or substituted with one or more substituents selected from halo, OH, $NO_2$, CN, $C_1$-$C_4$-alkyl, $C_1$-$C_4$-alkoxy, —C(O)—$C_1$-$C_4$-alkyl, —C(O)-aryl, —C(O)-heteroaryl, —OC(O)—$C_1$-$C_4$-alkyl, —OC(O)-aryl, —OC(O)-heteroaryl, —$NR^a$C(O)—$C_1$-$C_4$-alkyl, —$NR^a$C(O)-aryl, —$NR^a$C(O)-heteroaryl, aryl, and heteroaryl.

Provided herein are pharmaceutical compositions of compounds disclosed herein, e.g., that comprise a pharmaceutically acceptable excipient and a compound of Formula (I) or a pharmaceutically acceptable salt thereof. The pharmaceutical compositions can be used in therapy, e.g., for treating a disease or condition disclosed herein in a subject.

Provided herein are methods of promoting survival of a eukaryotic cell by modulating NAD+ activity in a subject by administering to the subject a therapeutically effective amount of a compound or pharmaceutical composition as disclosed herein.

Provided herein are methods of treating or preventing a disease or disorder associated with cell death, cell dysfunction, or aging in a subject by administering to the subject a compound or pharmaceutical composition as disclosed herein.

Provided herein are methods of treating or preventing insulin resistance, a metabolic syndrome, hypercholesterolemia, atherogenic dyslipidemia, diabetes, abnormal blood glucose concentration, or complications thereof, or for increasing insulin sensitivity in a subject by administering to the subject a compound or a pharmaceutical composition as disclosed herein.

Provided herein are methods of treating or preventing a neurological or neurodegenerative disorder in a subject by administering to the subject a compound or pharmaceutical composition as disclosed herein.

Provided herein are methods for repair of DNA damaged by drug or radiation toxicity in a subject by administering to the subject a compound or pharmaceutical composition as disclosed herein.

Provided herein are methods for treating or preventing cardiovascular diseases and conditions in a subject by administering to the subject a compound or pharmaceutical composition as disclosed herein.

Provided herein are methods for treating or preventing circadian rhythm disorders in a subject by administering to the subject a compound or pharmaceutical composition as disclosed herein.

Provided herein are methods for treating or preventing liver disease in a subject by administering to the subject a compound or pharmaceutical composition as disclosed herein.

Provided herein are methods for treating or preventing retinal diseases and disorders in a subject by administering to the subject a compound or pharmaceutical composition as disclosed herein.

In yet another aspect, provided herein are methods of treating or preventing a mitochondrial-related disease or condition in a subject by administering to the subject a compound or pharmaceutical composition as disclosed herein.

DETAILED DESCRIPTION

Figure 1:
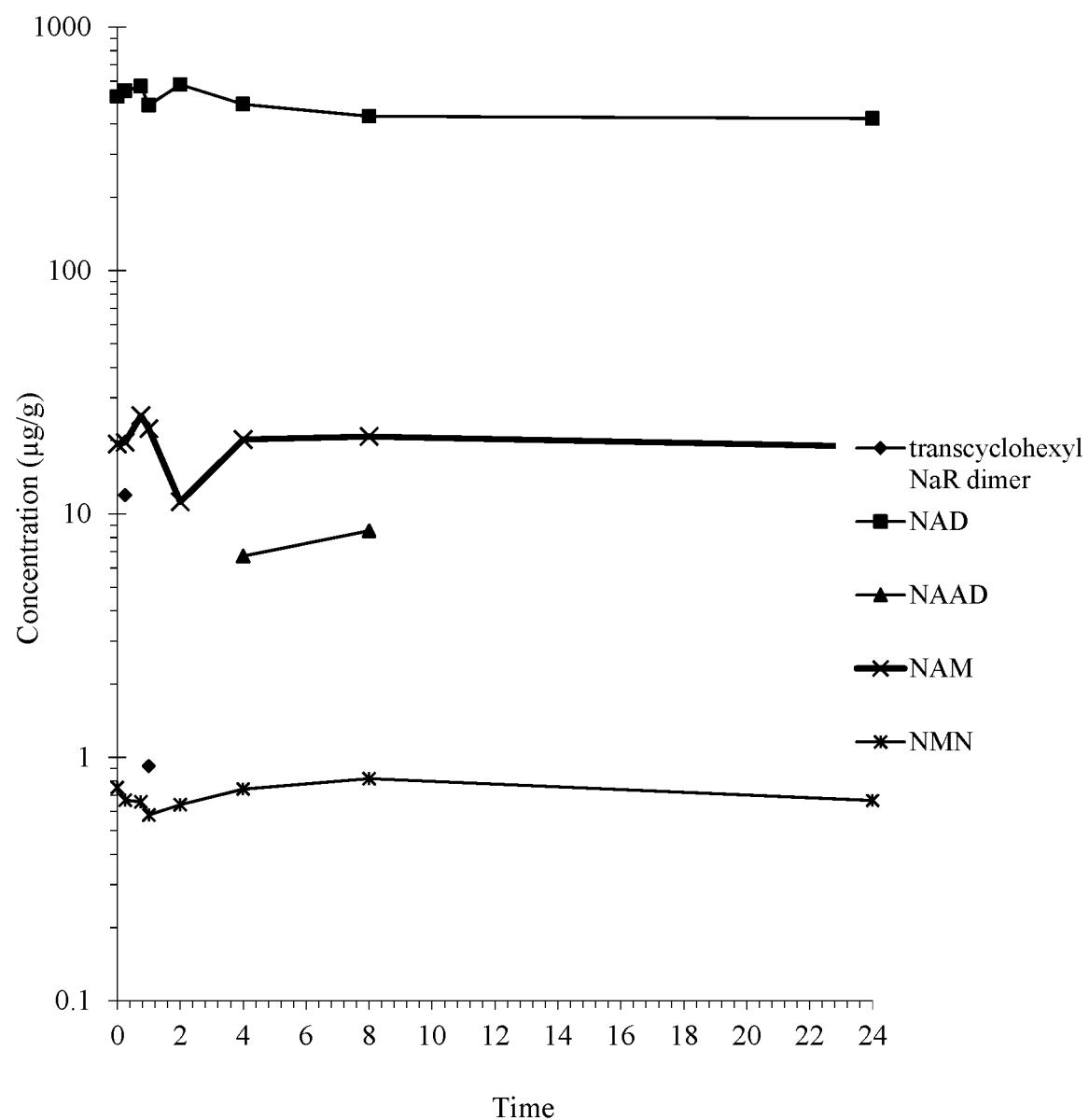
FIG. 1 depicts summary muscle concentrations of trans-cyclohexyl NaR dimer, NAD, NAAD, NAM, and NMN following 500 mg/kg oral gavage administration of trans-cyclohexyl NaR dimer.

NAD+ and its phosphorylated analog, NADP, are indispensable cofactors for numerous oxidoreductases in many organisms. NAD+ and NADP also serve as cofactors for enzymes that do not appear to be involved in oxidation or reduction. For example, many proteins require NAD+ for their activity. NAD+-dependent activity can cause alterations in gene expression, repression of ribosomal DNA recombination, and the health benefits and lifespan extension provided by calorie restriction. Accordingly, compounds capable of modulating NAD+ activity may be useful in a variety of medical conditions in mammals (e.g., humans), such as those that are caused by or associated with changes in gene expression and age of the individual. These medical conditions include disorders related to aging or stress, diabetes, obesity, neurodegenerative diseases, cardiovascular disease, blood clotting disorders, inflammation, cataracts, flushing, cell death, cancer, appetite, and/or weight gain.

Nicotinic acid riboside (NAR) is a pyridine-nucleoside form of vitamin B3 that functions as a precursor to nicotinamide adenine dinucleotide or NAD.

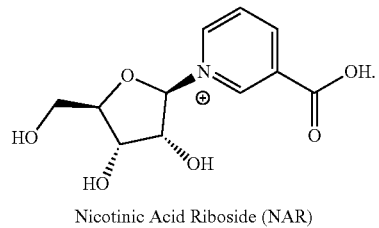

Nicotinic Acid Riboside (NAR)

Accordingly, this invention provides, inter alia, compounds and methods for modulating NAD+ activity. In particular, the compounds disclosed herein comprise one or more NAR molecules covalently linked via a linking group (e.g., a lipophilic linking group, a linking group that influences charge separation, etc.). In preferred embodiments, the compounds disclosed herein comprise an NAR dimer, wherein two NAR subunits (which may comprise modifications such as acetylation) are covalently linked via a linking group.

Compounds disclosed herein may be provided as pharmaceutical compositions. Such pharmaceutical compositions may further comprise one or more pharmaceutically acceptable carriers.

The compounds and pharmaceutical compositions disclosed herein are useful for treating various diseases and conditions, such as disorders related to aging or stress, diabetes, obesity, neurodegenerative diseases, cardiovascular disease, blood clotting disorders, inflammation, cataracts, flushing, cell death, cancer, appetite, and/or weight gain.

Definitions

The term "alkyl" used alone or as part of a larger moiety, such as "alkoxy", "haloalkyl", "cycloalkyl", "heterocycloalkyl", and the like, refers to a straight chained or branched non-aromatic hydrocarbon which is completely saturated. Typically, a straight chained or branched alkyl group has from 1 to about 20 carbon atoms, preferably from 1 to about 10 carbon atoms, unless otherwise defined. Examples of straight chained and branched alkyl groups include, but are not limited to, methyl, ethyl, propyl, isopropyl, n-butyl, sec-butyl, tert-butyl, n-pentyl, n-hexyl, n-heptyl, and n-octyl. A $C_1$-$C_6$ straight chained or branched alkyl group is also referred to as a "lower alkyl" group.

Moreover, the term "alkyl" (or "lower alkyl"), as used herein, is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. The skilled artisan will understand that the moieties substituted on the hydrocarbon chain can themselves be substituted, if appropriate. For example, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed above, except where stability is prohibitive. For example, substitution of alkenyl groups by one or more alkyl, carbocyclyl, aryl, heterocyclyl, or heteroaryl groups is contemplated.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "$C_x$-$C_y$" when used in conjunction with a chemical moiety, such as, for example, acyl, acyloxy, alkyl, alkenyl, alkynyl, or alkoxy is meant to include groups that contain from x to y carbons in the chain, wherein "x" and "y" are integers selected from 1 to about 20, and wherein x is an integer of lesser value than y, and x and y are not the same value. For example, the term "$C_x$-$C_y$-alkyl" refers to substituted or unsubstituted saturated hydrocarbon groups, including straight-chain alkyl and branched-chain alkyl groups that contain from x to y number of carbons in the chain, including haloalkyl groups such as trifluoromethyl and 2,2,2-tirfluoroethyl, etc. The terms "$C_2$-$C_y$-alkenyl" and "$C_2$-$C_y$-alkynyl" refer to substituted or unsubstituted unsaturated aliphatic groups analogous in length and possible substitution to the alkyls described above, but that contain at least one double or triple bond respectively. As applied to heteroalkyls, "$C_x$-$C_y$" indicates that the group contains from x to y number of carbons and heteroatoms in the chain. As applied to carbocyclic structures, such as aryl and cycloalkyl groups, "$C_x$-$C_y$" indicates that the ring comprises x to y number of carbon atoms in the ring. As applied to heterocyclic structures, such as heteroaryl and heterocyclyl groups, "$C_x$-$C_y$" indicates that the ring contains from x to y carbons in the ring.

The term "alkoxy" refers to an alkyl group, preferably a lower alkyl group, having an oxygen attached thereto. Representative alkoxy groups include methoxy, ethoxy, propoxy, tert-butoxy and the like.

The terms "haloalkyl" and "haloalkoxy" refer to alkyl or alkoxy, as the case may be, substituted with one or more halogen atoms. In some embodiments, "haloalkyl" and "haloalkoxy" refer to alkyl or alkoxy, as the case may be, substituted with one or more fluorine, chlorine, bromine, or iodine atoms.

The term "halogen" refers to fluorine or fluoro (F), chlorine or chloro ($C_1$), bromine or bromo (Br), or iodine or iodo (I).

The term "cycloalkyl", as used herein, refers a substituted or unsubstituted cyclic hydrocarbon which is completely saturated. Cycloalkyl includes monocyclic and bicyclic rings. Typically, a monocyclic cycloalkyl group has from 3 to about 10 carbon atoms, more typically 3 to 8 carbon atoms, unless otherwise defined. The second ring of a bicyclic cycloalkyl may be selected from saturated, unsaturated, and aromatic rings. Cycloalkyl includes bicyclic molecules in which one, two, or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "aralkyl", as used herein, refers to an alkyl group substituted with an aryl group.

The term "aryl", as used herein, refers to substituted or unsubstituted single-ring aromatic groups in which each atom of the ring is carbon. Preferably, the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

"The term "heterocyclyl" and "heterocycle", as used herein, refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. Such heterocycles also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, tetrahydrofurans, tetrahydropyrans, and the like. Exemplary tetrahydrofurans and tetrahydropyrans include those with one or more hydroxyl substituents, such as monosaccharides. In some embodiments, heterocyclyl rings can be joined together in a chain separated by a linking atom, such as —O—, or another linking group, such as —$(CH_2)_n$— where n is an integer from 1 to 6. Exemplary linked heterocyclyls include carbohydrates, such as disaccharides, oligosaccharides and polysaccharides.

The term "heteroaryl" includes substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroaralkyl", as used herein, refers to an alkyl group substituted with a heteroaryl group.

Alkyl, alkenyl, alkynyl, haloalkyl, cycloalkyl, aralkyl, aryl, heterocyclyl, and heteroaryl groups having two open valences are sometimes referred to with an "ene" suffix, as in alkylene, alkenylene, alkynylene, haloalkylene, cycloalkylene, aralkylene, arylene, heterocyclylene, and heteroarylene. For example, alkylene groups include methylene, ethylene, propylene, and the like.

The term "counteranion" means any anion that balances the positive charge, if present, of compounds disclosed herein. Representative counteranions include chloride, triflate, sulfate, and the like. Preferred "counteranions" include pharmaceutically acceptable anions that are suitable for administration to mammals, such as humans. Suitable pharmaceutically acceptable counteranions include inorganic anions (such as chloride, bromide, phosphate, nitrate, and sulfate) and organic anions (such as, e.g., acetate, benzenesulfonate, benzoate, methanesulfonate, and toluenesulfonate). See, e.g., Bighley, et al., "Salt Forms of Drugs and Absorption" in *Enclyclopedia of Pharmaceutical Technology*, Swarbrick, J. & Boylan, J. C. (Eds.) Vol. 13, Marcel Dekker: NY (1996) p. 453-499, which is incorporated by reference in its entirety.

The term "substituted" refers to moieties having substituents replacing a hydrogen on one or more carbons or heteroatoms of the moiety. The skilled artisan will understand that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds.

In some embodiments, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, such as, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. The skilled artisan will understand that substituents can themselves be substituted, if appropriate. Unless specifically stated as "unsubstituted", references to chemical moieties herein are understood to include substituted variants. For example, reference to an "aryl" group or moiety implicitly includes both substituted and unsubstituted variants.

In certain embodiments, compounds of the invention may be racemic. In certain embodiments, compounds of the invention may be enriched in one enantiomer. For example, a compound of the invention may have greater than about 30% ee, about 40% ee, about 50% ee, about 60% ee, about 70% ee, about 80% ee, about 90% ee, or even about 95% or greater ee. Compounds of the invention are preferably greater than about 90% ee, most preferably greater than about 95% ee. In certain embodiments, compounds of the invention may have more than one stereocenter. In certain such embodiments, compounds of the invention may be enriched in one or more diastereomer. For example, a compound of the invention may have greater than about 30% de, about 40% de, about 50% de, about 60% de, about 70% de, about 80% de, about 90% de, or even about 95% or greater de. Compounds of the invention are preferably greater than about 90% de, most preferably greater than about 95% de.

In certain embodiments, the therapeutic preparation may be enriched to provide predominantly one enantiomer of a compound (e.g., a compound of Formula (I), (II), (III), (IV), or (V)). An enantiomerically enriched mixture may comprise, for example, at least about 60 mol percent of one enantiomer, or more preferably at least about 75, about 90, about 95, or even about 99 mol percent. In certain embodiments, the compound enriched in one enantiomer is substantially free of the other enantiomer, wherein substantially free means that the substance in question makes up less than about 10%, or less than about 5%, or less than about 4%, or less than about 3%, or less than about 2%, or less than about 1% as compared to the amount of the other enantiomer, e.g., in the composition or compound mixture. For example, if a composition or compound mixture contains about 98 grams of a first enantiomer and about 2 grams of a second enantiomer, it would be said to contain about 98 mol percent of the first enantiomer and only about 2% of the second enantiomer.

In certain embodiments, the therapeutic preparation may be enriched to provide predominantly one diastereomer of a compound (e.g., a compound of Formula (I), (II), (III), (IV), or (V)). A diastereomerically enriched mixture may comprise, for example, at least about 60 mol percent of one diastereomer, or more preferably at least about 75, about 90, about 95, or even about 99 mol percent.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

In certain embodiments, compounds of Formula (I), (II), (III), (IV), and/or (V) may be used alone or conjointly administered with another type of therapeutic compound or agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

Compounds of the Invention

Included in the present disclosure are compounds having a structure of Formula (I):

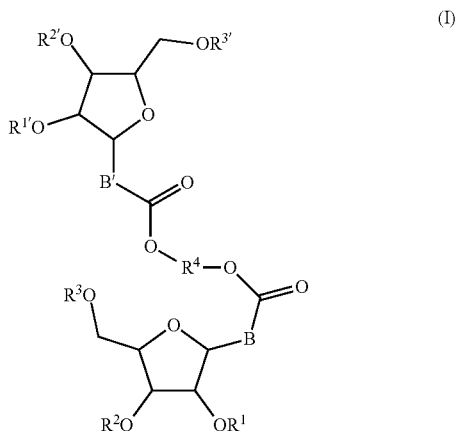
(I)

or a pharmaceutically acceptable salt thereof, wherein:
B and B' are each independently

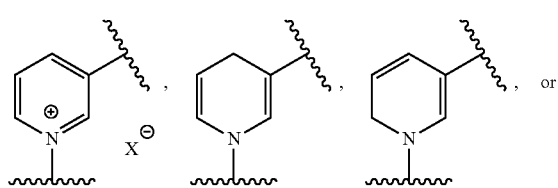

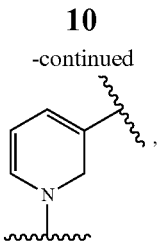

e.g., wherein the nitrogen is bound to the tetrahydrofuran ring;

$X^-$ is a counterion;

$R^1$, $R^2$, $R^3$, $R^{1'}$, $R^{2'}$, and $R^{3'}$ are each, independently hydrogen, substituted or unsubstituted alkyl, or substituted or unsubstituted —C(O)-alkyl; and $R^4$ is alkylene, alkenylene, alkynylene, cycloalkylene, cycloalkenylene, heteroalkylene, arylene, aralkylene, heterocyclylene, heteroarylene, or heteroaralkylene, each of which is substituted or unsubstituted; and $R^a$ is hydrogen or alkyl.

In certain embodiments, the alkylene group, the alkenylene group, the alkynylene group, the cycloalkylene group, the cycloalkenylene group, the heteroalkylene group, the arylene group, the aralkylene group, the heterocyclylene group, the heteroarylene group, or the heteroaralkylene group of $R^4$ is substituted with one or more substituents selected from halo, OH, $NO_2$, CN, alkyl, alkoxy, alkenyl, alkynyl, —C(O)-alkyl, —C(O)-aryl, —C(O)— heteroaryl, —OC(O)-alkyl, —OC(O)-aryl, —OC(O)-heteroaryl, —$NR^a$C(O)-alkyl, —$NR^a$C(O)-aryl, —$NR^a$C(O)-heteroaryl, cycloalkyl, cycloalkenyl, aryl, and heteroaryl.

In some embodiments, the compounds have a structure according to Formula (II):

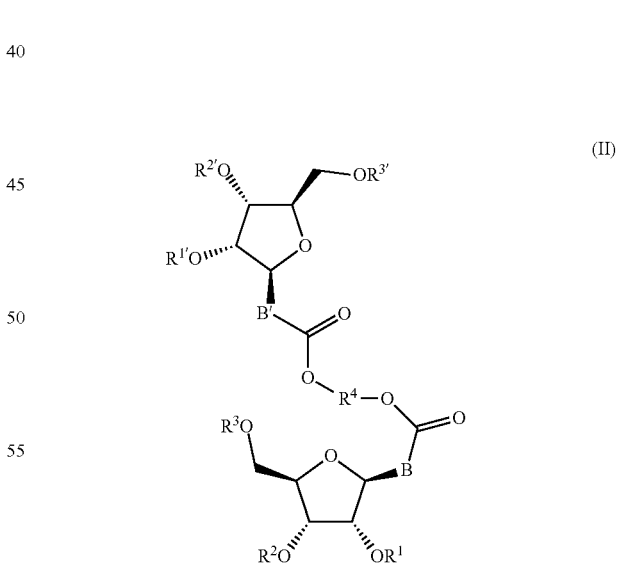
(II)

or a pharmaceutically acceptable salt thereof, wherein the definitions of the variables are as defined for the compounds of Formula (I) above.

In preferred embodiments of the compounds of Formula (I) and (II), B and B' are the same. More preferably, B and B' are both

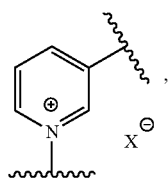

wherein X⁻ is as defined for the compounds of Formula (I).

In certain embodiments, the compounds have a structure according to Formula (III):

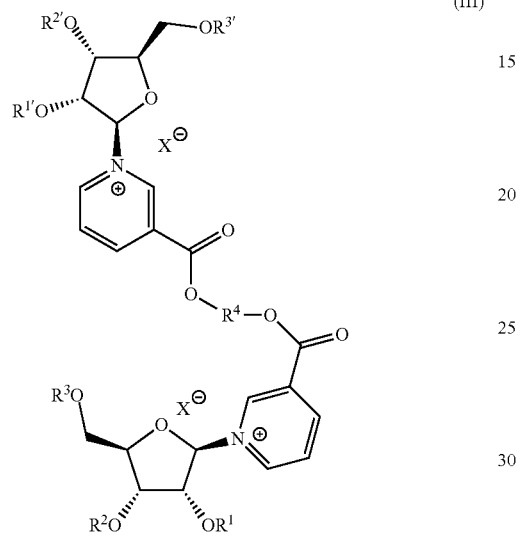

(III)

or a pharmaceutically acceptable salt thereof, wherein the definitions of the variables are as defined for the compounds of Formula (I).

In preferred embodiments of the compounds of Formula (I), (II), and (III), $R^1$ and $R^{1'}$; $R^2$ and $R^{2'}$; $R^3$ and $R^{3'}$ are the same. More preferably, $R^1$, $R^2$, $R^3$, $R^{1'}$, $R^{2'}$, and $R^{3'}$ are the same. Even more preferably, $R^1$, $R^2$, $R^3$, $R^{1'}$, $R^{2'}$, and $R^{3'}$ are each unsubstituted —$C_1$-$C_4$-alkyl or unsubstituted —C(O)—$C_1$-$C_4$-alkyl.

In some such embodiments, the compounds have a structure according to Formula (IV):

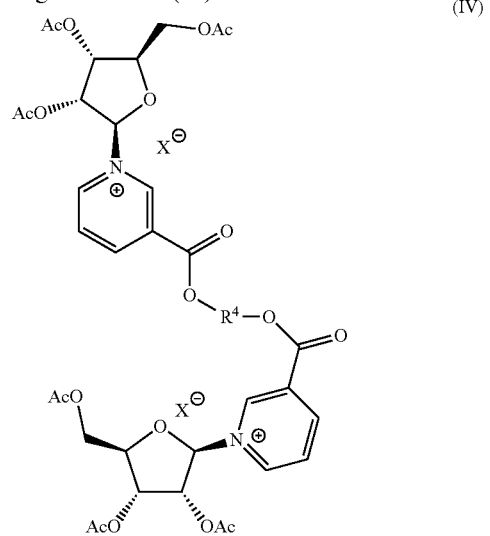

(IV)

or a pharmaceutically acceptable salt thereof, wherein the definitions of the variables are as defined for the compounds of Formula (I).

In other embodiments, the compounds have a structure according to Formula (V):

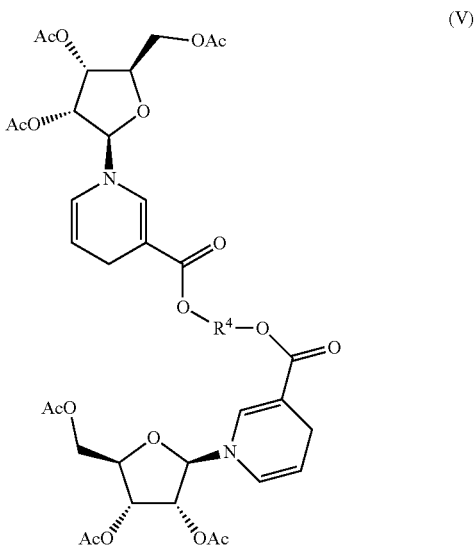

(V)

or a pharmaceutically acceptable salt thereof, wherein the definitions of the variables are as defined for the compounds of Formula (I).

In some embodiments of the compounds of Formula (I), (II), (III), (IV), and (V), $R^4$ is $C_1$-$C_6$-alkylene, $C_2$-$C_6$-alkenylene, $C_2$-$C_6$-alkynylene, $C_3$-$C_6$-cycloalkylene, $C_3$-$C_6$-cycloalkenylene, arylene, heterocyclylene, heteroarylene, or heteroaryl-$C_2$-$C_6$-alkylene, each of which is unsubstituted or substituted with one or more substituents selected from halo, OH, $NO_2$, CN, $C_1$-$C_4$-alkyl, $C_1$-$C_4$-alkoxy, —C(O)—$C_1$-$C_4$-alkyl, —C(O)-aryl, —C(O)-heteroaryl, —OC(O)—$C_1$-$C_4$-alkyl, —OC(O)-aryl, —OC(O)-heteroaryl, —$NR^aC(O)$—$C_1$-$C_4$-alkyl, —$NR^aC(O)$-aryl, —$NR^aC(O)$-heteroaryl, aryl, and heteroaryl. In preferred embodiments, $R^4$ is unsubstituted $C_1$-$C_6$-alkylene, unsubstituted $C_2$-$C_6$-alkenylene, unsubstituted $C_2$-$C_6$-alkynylene, unsubstituted $C_3$-$C_6$-cycloalkylene, unsubstituted arylene, or unsubstituted aralkylene. Alternatively, $R^4$ is $C_1$-$C_6$-alkylene substituted with $C_1$-$C_4$-alkyl or —OC(O)— heteroaryl.

In certain embodiments, $R^4$ is an aralkylene moiety of structural formula:

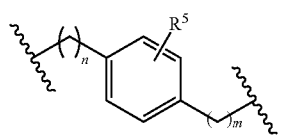

wherein $R^5$ hydrogen, halo, OH, $NO_2$, CN, $C_1$-$C_4$-alkyl, $C_1$-$C_4$-alkoxy, —C(O)—$C_1$-$C_4$-alkyl, —C(O)-aryl, —C(O)-heteroaryl, —OC(O)—$C_1$-$C_4$-alkyl, —OC(O)-aryl, —OC(O)-heteroaryl, -$NR^aC(O)$—$C_1$-$C_4$-alkyl, —$NR^aC(O)$-aryl, —$NR^aC(O)$-heteroaryl, aryl, and heteroaryl; and m and n are each integers from 1 to about 6, wherein the value of m is independent of the value of n.

In certain embodiments of the compounds of Formula (I), (II), (III), (IV), and (V), $R^4$ is selected from:

In some embodiments of the compounds of Formula (I), (II), (III), (IV), and (V), R⁴ is selected from:

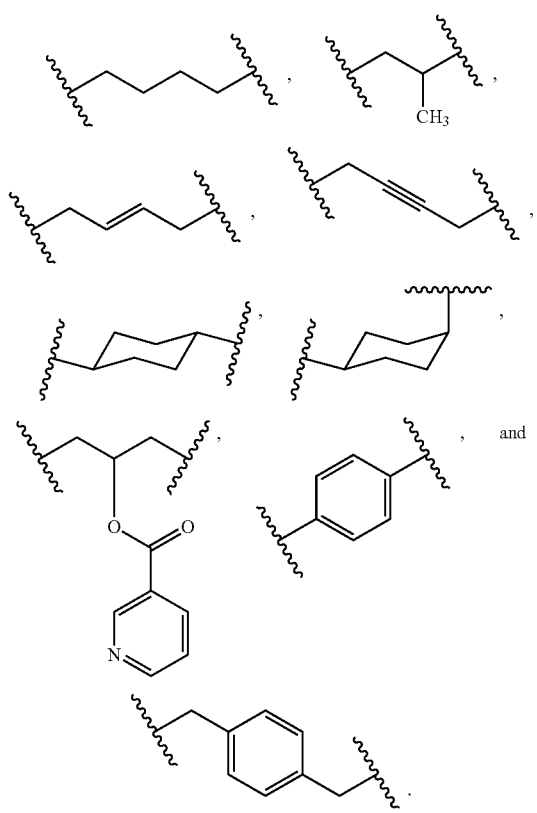

In other embodiments, of the compounds of Formula (I), (II), (III), (IV), and (V), R⁴ is selected from:

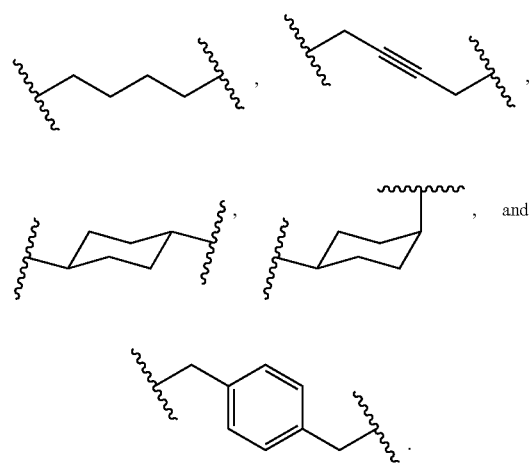

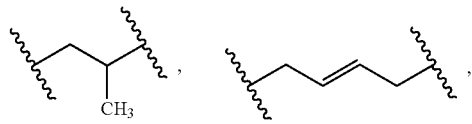

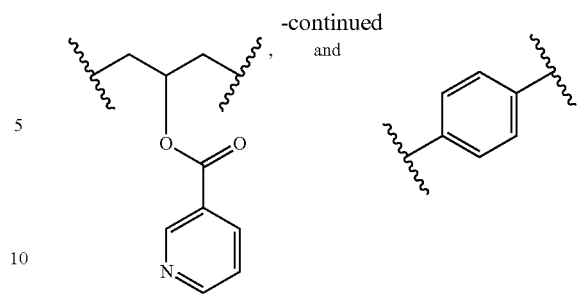

In other embodiments of the compounds of Formula (I), (II), (III), (IV), and (V), R⁴ is

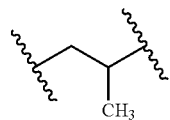

In other embodiments of the compounds of Formula (I), (II), (III), (IV), and (V), R⁴ is

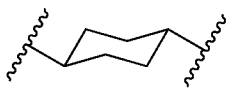

In other embodiments of the compounds of Formula (I), (II), (III), (IV), and (V), R⁴ is heterocycloalkylene selected from monosaccharides, disaccharides, oligosaccharides and polysaccharides, where the oxygen atoms attached to R₄ are oxygen atoms of the monosaccharide, disaccharide, oligosaccharide, or polysaccharide in its unbound form.

In other embodiments of the compounds of Formula (I), (II), (III), (IV), and (V), each X⁻ is independently selected from Cl⁻, OH⁻, SO₄H⁻, HPO₄²⁻, CH₃COO⁻, CF₃COO⁻, BF₄⁻, PF₆⁻, SbF₆⁻, CH₃SO₃⁻, CF₃SO₃⁻, and PhCO₂⁻. Preferably, each X⁻ is independently selected from Cl⁻, SO₄H⁻, CH₃COO⁻, CF₃COO⁻, CF₃SO₃⁻, and CH₃SO₃⁻.

In some embodiments, the compound is selected from:

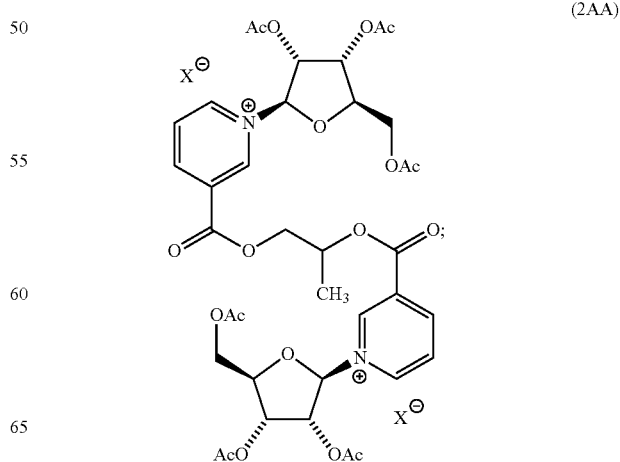

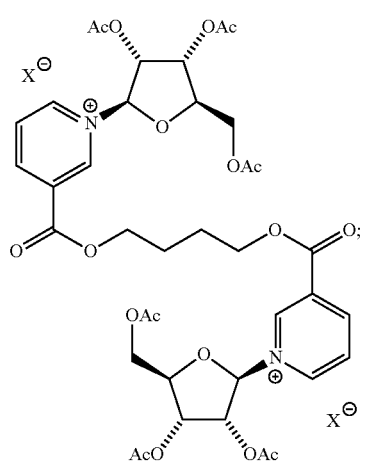
(2BB)
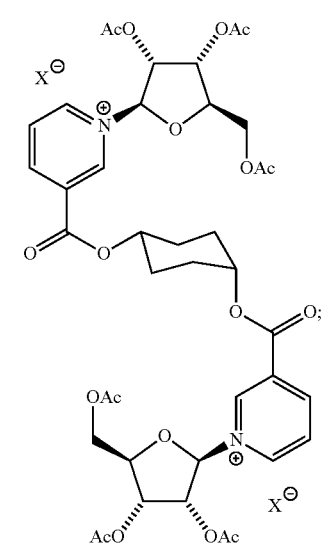
(2CC)
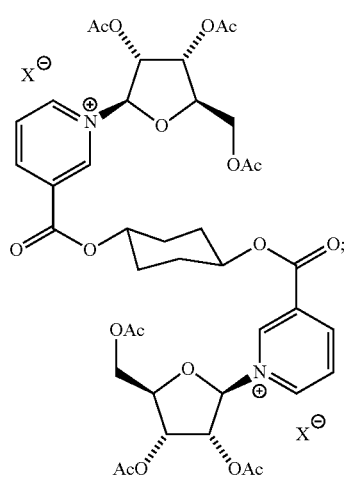
(2DD)
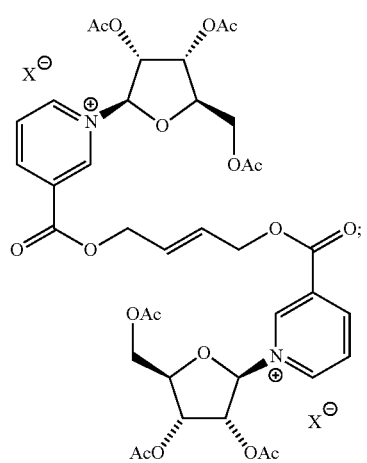
(2EE)
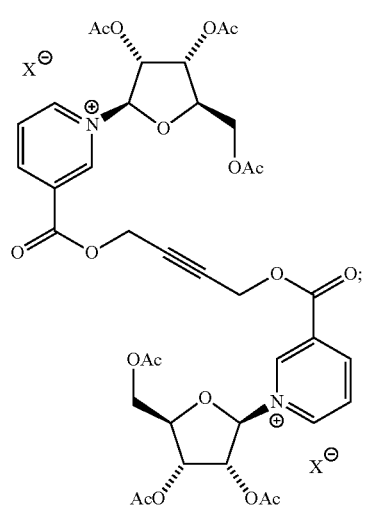
(2FF)
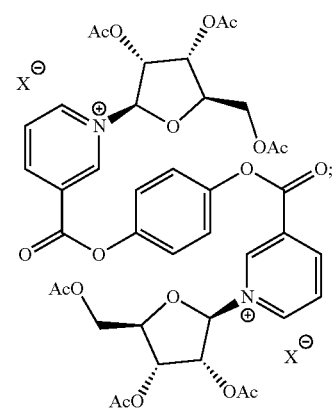
(2GG)

(2HH)
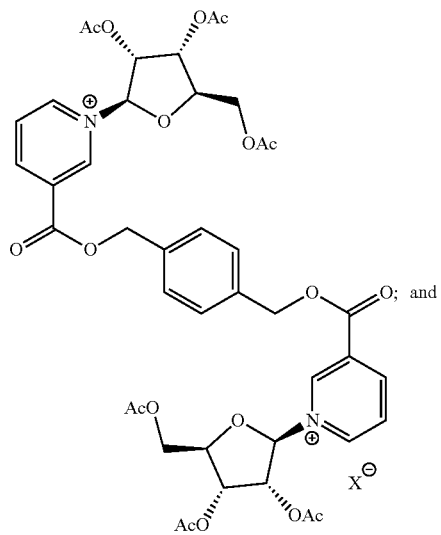
(2II)
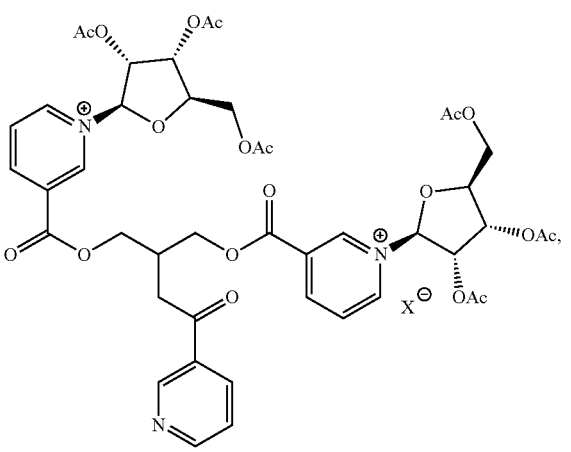
or a pharmaceutically acceptable salt thereof.
In some embodiments, the compound is selected from:
(2A)
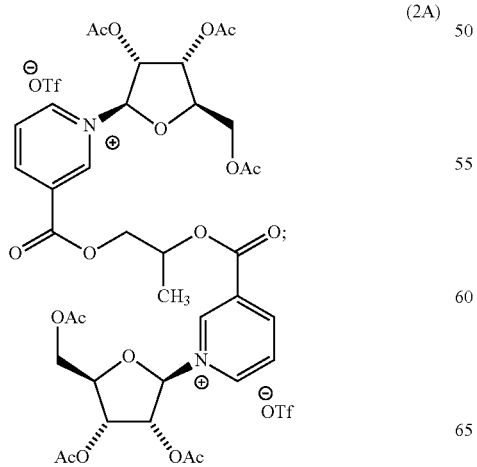
(2B)
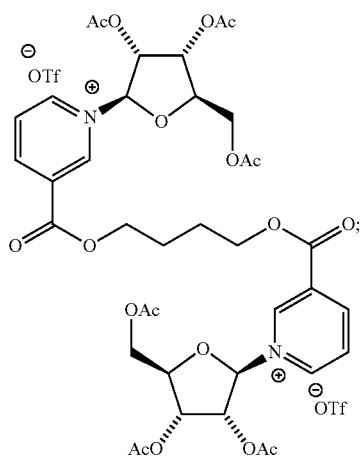
(2C)
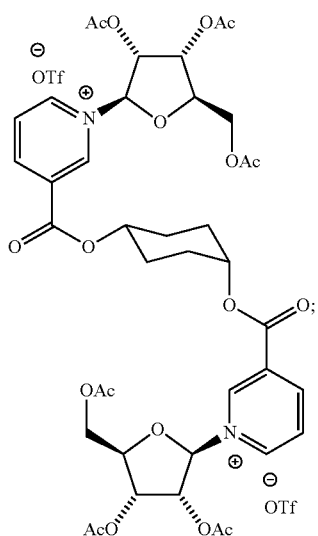
(2D)
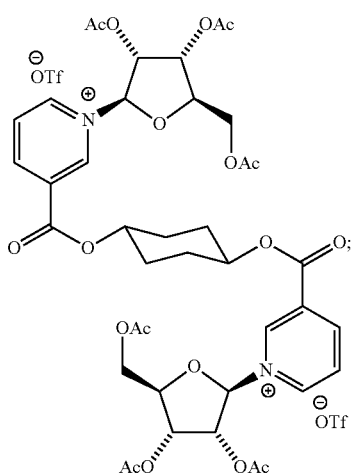

-continued
(2E)
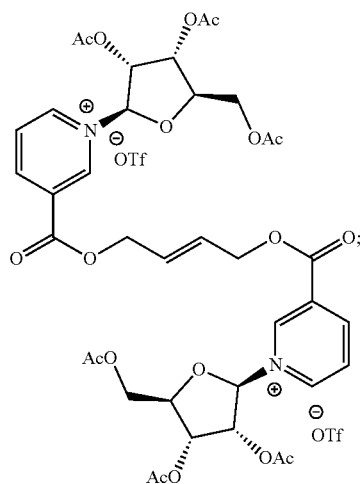
(2F)
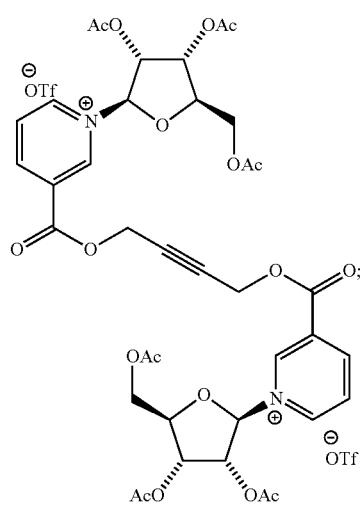
(2G)
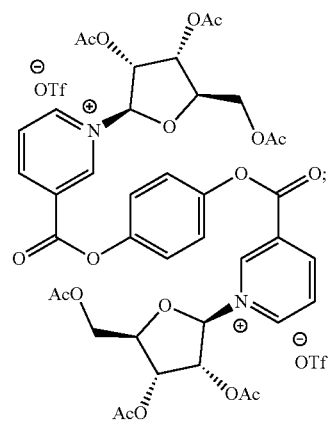
-continued
(2H)
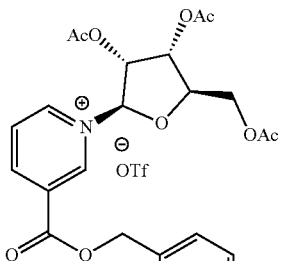
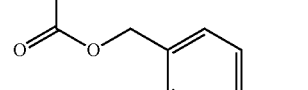
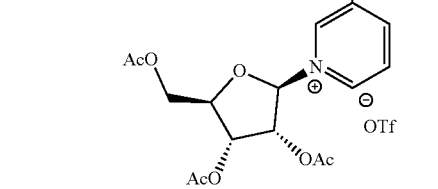
(2I)
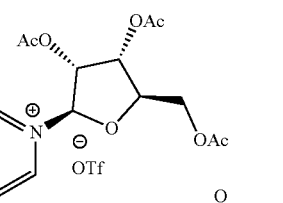
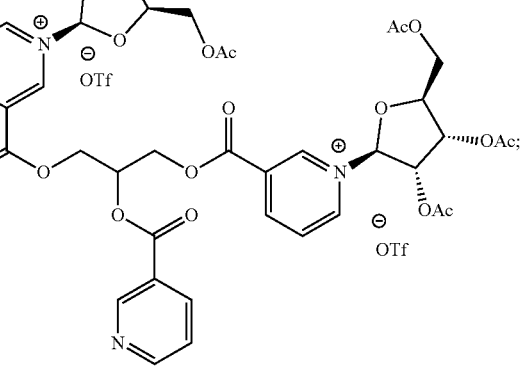
or a pharmaceutically acceptable salt thereof.
In certain preferred embodiments, the compound is selected from:
(2B)
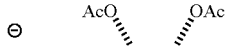

-continued
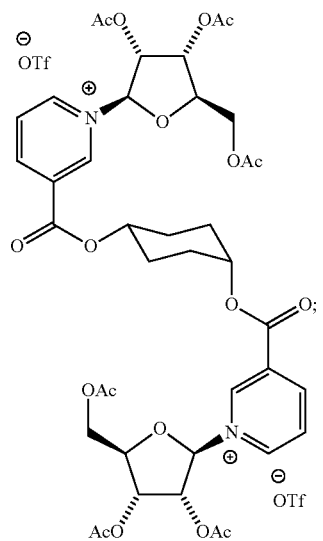
(2C)
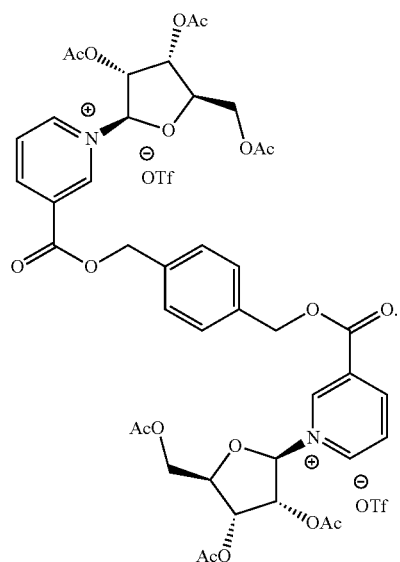
(2H)
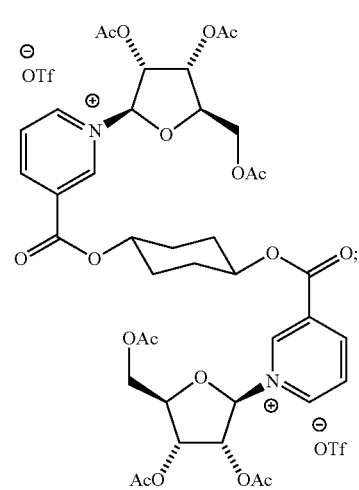
(2D)
In other embodiments, the compound is selected from:
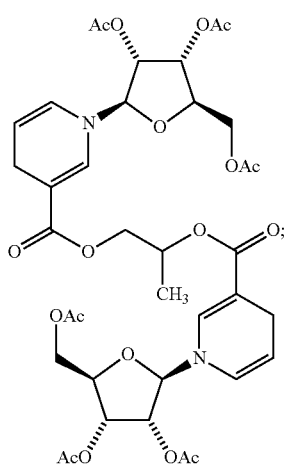
(3A)
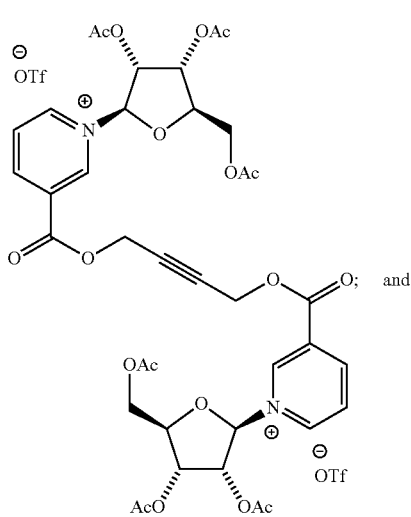
(2F) and
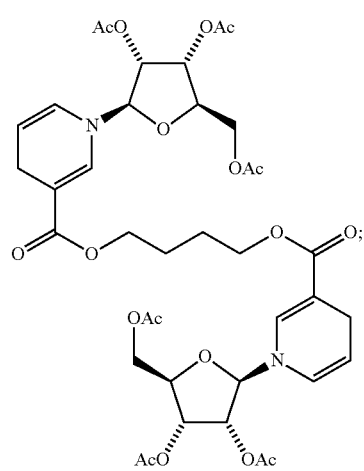
(3B)

(3C)
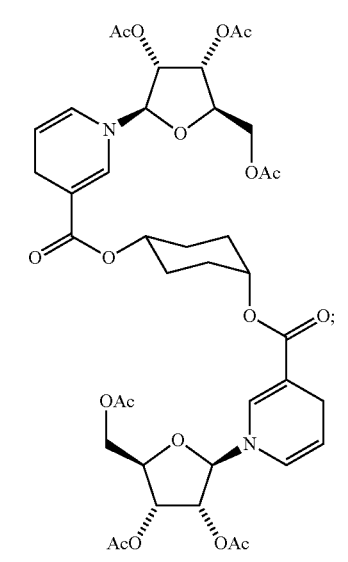
(3D)
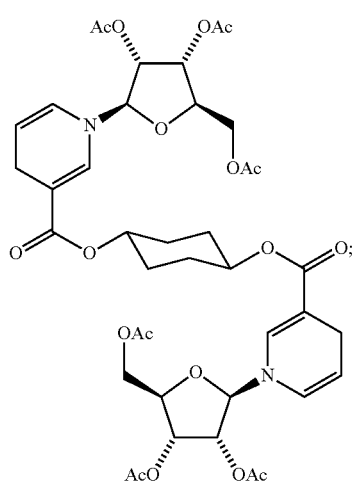
(3E)
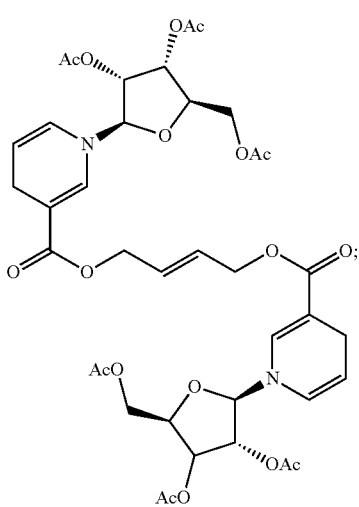
(3F)
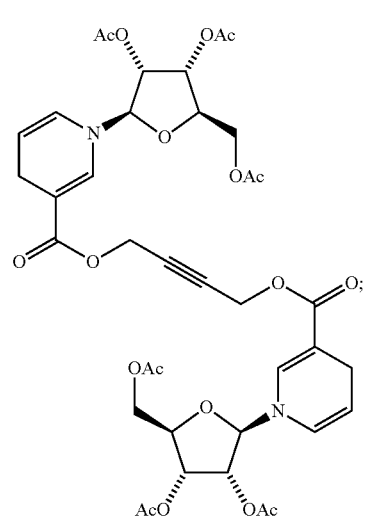
(3G)
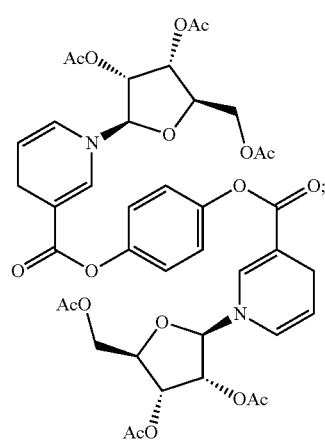
(3H)
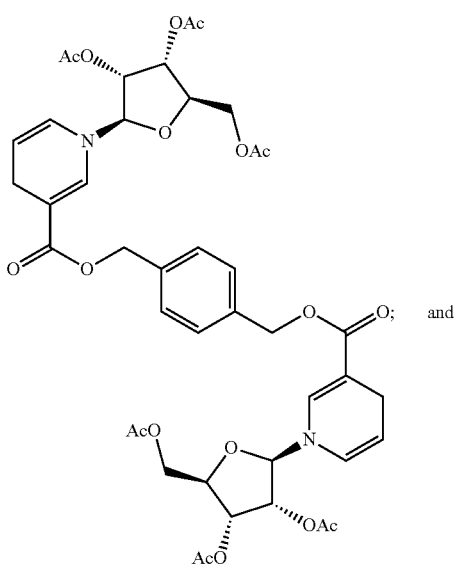
and

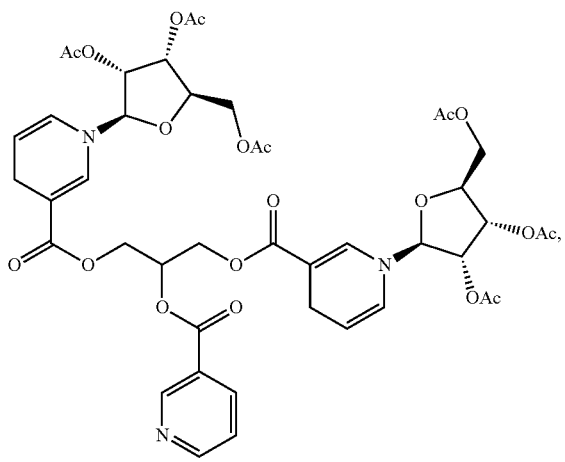

(3I)

or a pharmaceutically acceptable salt thereof.

In some embodiments, the compound is:

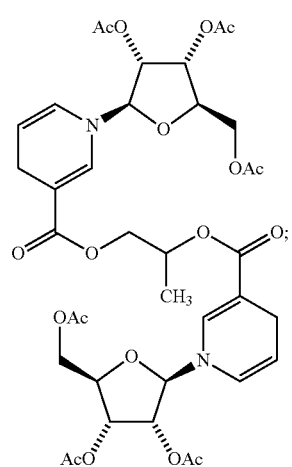

(3A)

or a pharmaceutically acceptable salt thereof.

Bioavailability of the Compounds of the Invention

NAR is strongly hydrophilic (and lipophobic) molecule by virtue of its inherent structure, in particular its pyridinium character. The compounds disclosed herein possess increased lipophobicity by virtue of the covalently linkage joining two nicotinamide riboside derivatives via a lipophilic group (referred to herein as $R^4$).

The lipophilicity of a group may be determined by measuring the partition coefficient of the molecule HZ (where Z is the group in question) between a nonpolar solvent (e.g., ethanol, dioxane, acetone, benzene, n-octanol) and water, at standard temperature and pressure (STP). The lipophilicity may be defined as the logarithm of this partition coefficient; it will then be positive for molecules which prefer the nonpolar solvent. Thus, a lipophilic group is one for which log P is greater than zero.

The partition coefficient (P) is defined as the ratio of the equilibrium concentrations of a dissolved substance in a two-phase system consisting of two largely immiscible solvents. One such system is n-octanol:water; the octanol phase will contain about 20% water and the water phase about 0.008% octanol. Thus, the relevant partition coefficient (Pow) is the ratio of the molar concentration of the solute in octanol (O) saturated with water (w) to its molar concentration in water saturated with octanol. Octanol is a useful surrogate for biological membranes because it, like many membrane components, is amphiphilic.

The biological availability of the compounds disclosed herein may be enhanced by virtue of a form of the compound that, under physiologic conditions, is converted into the therapeutically active agent of the present invention (e.g., a compound of Formula (I), (II), (III), (IV), and/or (V)). Such a form of the compounds disclosed herein can have improved lipophilicity relative to nicotinamide riboside, and this can result in enhanced membrane permeability. One particularly useful form is an ester derivative, e.g., of a hydroxyl substituent. Its utility relies upon the action of one or more of the ubiquitous plasma esterases to catalyze the hydrolysis of ester groups, to release the active compound at or near its site of action. In one form of the compounds disclosed herein, one or more hydroxy groups in the compound can be O-acylated, e.g., acetylated, to make an acylate (e.g., acetyl) derivative.

Methods of Treatment

Nicotinamide adenine dinucleotide (NAD) and its derivative compounds are known as essential coenzymes in cellular redox reactions in all living organisms. Several lines of evidence have also shown that NAD participates in a number of important signaling pathways in mammalian cells, including poly(ADP-ribosyl)ation in DNA repair (Menissier de Murcia et al., EMBO J., (2003) 22, 2255-2263), mono-ADP-ribosylation in the immune response and G protein-coupled signaling (Corda and Di Girolamo, EMBO J., (2003) 22, 1953-8), and the synthesis of cyclic ADP-ribose and nicotinate adenine dinucleotide phosphate (NAADP) in intracellular calcium signaling (Lee, Annu. Rev. Pharmacol. Toxicol., (2001) 41, 317-345). Recently, it has also been shown that NAD and its derivatives play an important role in transcriptional regulation (Lin and Guarente, Curr. Opin. Cell. Biol., (2003) 15, 241-246). In particular, the discovery of Sir2 NAD-dependent deacetylase activity (e.g., Imai et al., Nature, (2000) 403, 795-800; Landry et al., Biochem. Biophys. Res. Commun., (2000) 278, 685-690; Smith et al., Proc. Natl. Acad. Sci. USA, (2000) 97, 6658-6663) drew attention to this new role of NAD.

The Sir2 family of proteins consumes NAD for its deacetylase activity and regulates transcription by deacetylating histones and a number of other transcription regulators. Because of this absolute requirement for NAD, it has been proposed that Sir2 proteins function as energy sensors that convert the energy status of cells to the transcriptional regulatory status of genes (Imai et al., Nature, (2000) 403, 795-800; Imai et al., Cold Spring Harbor Symp. Quant. Biol., (2000) 65, 297-302). Sir2 proteins produce nicotinamide and 0-acetyl-ADP-ribose in addition to the deacetylated protein substrates in their deacetylation reaction (Moazed, Curr. Opin. Cell. Biol., (2001)13, 232-238; Denu, Trends Biochem. Sci., (2003) 28, 41-48; see also FIG. 1), and nicotinamide is eventually recycled into NAD biosynthesis. Unlike other NAD-dependent biochemical reactions, the NAD-dependent deacetylase activity of the Sir2 family of proteins is generally highly conserved from bacteria to mammals (Frye, Biochem. Biophys. Res. Commun., (2000) 273, 793-798), suggesting that the connection between NAD and Sir2 proteins is ancient and fundamental. In mammals, the Sir2 ortholog, Sirt1/Sir2α, has been shown to regulate metabolism in response to nutrient availability (Bordone and Guarente, Nat. Rev. Mol. Cell Biol., (2005) 6, 298-305). In adipocytes, Sirt1 triggers lipolysis and promotes free fatty acid mobilization by repressing PPAR-gamma, a nuclear receptor that promotes adipogenesis (Picard et al., Nature, (2004) 429, 771-776). In hepatocytes, Sirt1 regulates the gluconeogenic and glycolytic pathways in response to fasting by interacting with and deacetylating PGC-1α, a key transcriptional regulator of glucose production in the liver (Rodgers et al., Nature, (2005) 434, 113-118). Additionally, Sirt1 promotes insulin secretion in pancreatic beta cells in response to high glucose partly by repressing Ucp2 expression and increasing cellular ATP levels (Moynihan et al., Cell Metab., (2005) 2, 105-117). While little is known about the regulation of NAD biosynthesis in mammals, NAD biosynthesis may play a role in the regulation of metabolic responses by altering the activity of certain NAD-dependent enzymes such as Sirt1 in a variety of organs and/or tissues.

The NAD biosynthesis pathways have been characterized in prokaryotes by using $Escherichia$ $coli$ and $Salmonella$ $typhimurium$ (Penfound and Foster, Biosynthesis and recycling of NAD, in $Escherichia$ $coli$ and $Salmonella$: Cellular and Molecular Biology, p. 721-730, ed. Neidhardt, F. C., 1996, ASM Press: Washington, D.C.) and recently in yeast (Lin and Guarente, Curr. Opin. Cell. Biol., (2003) 15, 241-246; Denu, Trends Biochem. Sci., (2003) 28, 41-48). In prokaryotes and lower eukaryotes, NAD is synthesized by the de novo pathway via quinolinic acid and by the salvage pathway via nicotinic acid (Penfound and Foster, id.) In yeast, the de novo pathway begins with tryptophan, which is converted to nicotinic acid mononucleotide (NaMN) through six enzymatic steps and one non-enzymatic reaction (Lin and Guarente, Curr. Opin. Cell. Biol., (2003) 15, 241-246). Two genes, BNA1 and QPT1, have been characterized in this pathway in yeast. At the step of NaMN synthesis, the de novo pathway converges with the salvage pathway. The salvage pathway begins with the breakdown of NAD into nicotinamide and O-acetyl-ADP-ribose, which is mainly catalyzed by the Sir2 proteins in yeast. Nicotinamide is then deamidated to nicotinic acid by a nicotinamidase encoded by the PNC1 gene. Nicotinic acid phosphoribosyltransferase (Npt), encoded by the NPT1 gene, converts nicotinic acid to NaMN, which is eventually converted to NAD through the sequential reactions of nicotinamide/nicotinic acid mononucleotide adenylyltransferase (encoded by NMA1 and/or NMA2) and NAD synthetase (encoded by QNS1).

Many aspects of mammalian behavior and physiology are coordinated through interconnected networks of 24-hour central and peripheral oscillators that synchronize cycles of fuel storage and utilization to maintain organismal homeostasis. In mice, circadian disruption has been tied to metabolic disturbance (F. W. Turek et al., Science 308, 1043 (2005); R. D. Rudic et al., PLoS Biol. 2, e377 (2004)), while conversely, high-fat diet alters both behavioral and molecular rhythms (A. Kohsaka et al., Cell Metab. 6, 414 (2007); M. Barnea, Z. Madar, O. Froy, Endocrinology 150, 161 (2009)). The underlying mechanism of the mammalian clock consists of a transcription-translation feedback loop in which CLOCK and BMAL1 activate transcription of Cryptochrome (Cry1 and 2) and Period (Per1, 2, and 3), leading to subsequent repression of CLOCK:BMAL1 by CRY and PER proteins (J. S. Takahashi, H. K. Hong, C. H. Ko, E. L. McDearmon, Nat. Rev. Genet. 9, 764 (2008)). An additional feedback loop involves the transcriptional regulation of Bmal1 by ROR and REV-ERB (N. Preitner et al., Cell 110, 251 (2002); T. K. Sato et al., Neuron 43, 527 (2004)). Previous studies have also implicated a role for cellular NAD+ in the regulation of CLOCK and NPAS2 activity (J. Rutter, M. Reick, L. C. Wu, S. L. McKnight, Science 293, 510 (2001)), an observation consistent with the recent finding that the NAD+-dependent protein deacetylase SIRT1 modulates activity of the clock complex (Y. Nakahata et al., Cell 134, 329 (2008); G. Asher et al., Cell 134, 317 (2008)).

Provided herein are methods for using the disclosed compounds and pharmaceutical compositions thereof. The disclosed compounds and pharmaceutical compositions thereof can be useful for a variety of therapeutic applications including, for example, treating and/or reducing a wide variety of diseases and disorders including, for example, diseases or disorders related to aging or stress, diabetes, obesity, neurodegenerative diseases, cardiovascular disease, blood clotting disorders, inflammation, cancer, and/or flushing, etc. The methods comprise administering to a subject in need thereof a disclosed compound and/or pharmaceutical composition thereof.

In certain embodiments, the disclosed compounds and pharmaceutical compositions thereof may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated using the disclosed compounds and pharmaceutical compositions thereof prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with the nicotinamide riboside analog preparations or pharmaceutical compositions, or may have a subset of cells/tissue treated locally with the disclosed compounds and pharmaceutical compositions thereof. In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In other embodiments, the disclosed compounds and/or a pharmaceutical composition thereof can be used to treat skin conditions. Exemplary skin conditions that may be treated in accordance with the methods described herein include disorders or diseases associated with or caused by inflammation, sun damage, or natural aging. For example, the compositions find utility in the treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including pemphigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In other embodiments, the disclosed compounds and pharmaceutical compositions thereof may be used for the treatment of wounds and/or burns to promote healing, including, for example, first-, second- or third-degree burns and/or thermal, chemical or electrical burns.

The disclosed compounds and pharmaceutical compositions thereof can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amyotropic lateral sclerosis, and muscular dystrophy; AIDS; fulminant hepatitis; diseases linked to degeneration of the brain, such as Creutzfeld-Jakob disease, retinitis pigmentosa, and cerebellar degeneration; myelodysplasis such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure, or radiation exposure.

The disclosed compounds and pharmaceutical compositions thereof can also be administered to a subject suffering from an acute disease, e.g., damage to an organ or tissue, e.g., a subject suffering from stroke or myocardial infarction or a subject suffering from a spinal cord injury. The disclosed compounds and pharmaceutical compositions thereof may also be used to repair an alcoholic's liver.

In certain embodiments, the invention provides a method extending the lifespan of a cell, extending the proliferative capacity of a cell, slowing aging of a cell, promoting the survival of a cell, delaying cellular senescence in a cell, mimicking the effects of calorie restriction, increasing the resistance of a cell to stress, or preventing apoptosis of a cell, by contacting the cell with a nicotinamide mononucleotide based derivative compound. Recent studies have demonstrated the role NAD+ plays in the aging process and in age-related diseases and conditions. See, e.g., Imai, et al., "NAD+ and sirtuins in aging and disease" Trends in Cell Biol. 2014 24(8): 464-471; and Gomes, et al. "Declining NAD+ Induces a Pseudohypoxic State Disrupting Nuclear-Mitochondrial Communication during Aging" Cell 2013 155:1624-1638.

The methods described herein may be used to increase the amount of time that cells, particularly primary cells (e.g., cells obtained from an organism, e.g., a human), may be kept alive in an ex vivo cell culture. Embryonic stem (ES) cells and pluripotent cells, and cells differentiated therefrom, may also be treated with a nicotinamide mononucleotide based or derivative compound to keep the cells, or progeny thereof, in culture for longer periods of time. Such cells can also be used for transplantation into a subject, e.g., after ex vivo modification.

In certain embodiments, cells that are intended to be preserved for long periods of time may be treated with a nicotinamide mononucleotide based derivative compound. The cells may be in suspension (e.g., blood cells, serum, biological growth media, etc.) or in tissues or organs in a subject. For example, blood collected from an individual for purposes of transfusion may be treated with a nicotinamide mononucleotide based derivative compound to preserve the blood cells for longer periods of time. Additionally, blood to be used for forensic purposes may also be preserved using a nicotinamide mononucleotide based derivative compound. Other cells that may be treated to extend their lifespan or protect against apoptosis include cells for consumption, e.g., cells from non-human mammals (such as meat) or plant cells (such as vegetables).

Nicotinamide mononucleotide based derivative compounds may also be applied during developmental and growth phases in mammals, plants, insects or microorganisms, in order to, e.g., alter, retard or accelerate the developmental and/or growth process.

In certain embodiments, nicotinamide mononucleotide based derivative compounds may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated with the nicotinamide mononucleotide based derivative compound prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with a nicotinamide mononucleotide based derivative compound or may have a subset of cells/tissue treated locally with a nicotinamide mononucleotide based derivative compound. In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In certain embodiments, cells may be treated with a nicotinamide mononucleotide based derivative compound that increases the level of NAD+ in vivo, e.g., to increase their lifespan or prevent apoptosis. For example, skin can be protected from aging (e.g., developing wrinkles, loss of elasticity, etc.) by treating skin or epithelial cells with a nicotinamide mononucleotide based derivative compound that increases the level of intracellular NAD+. In exemplary embodiments, skin is contacted with a pharmaceutical or cosmetic composition comprising a nicotinamide mononucleotide based derivative compound that increases the level of intracellular NAD+. Exemplary skin afflictions or skin conditions that may be treated in accordance with the methods described herein include disorders or diseases associated with or caused by inflammation, sun damage or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In other embodiments, a nicotinamide mononucleotide based derivative compound that increases the level of intracellular NAD+ may be used for the treatment of wounds and/or burns to promote healing, including, for example, first-, second- or third-degree burns and/or thermal, chemical or electrical burns. The formulations may be administered topically, to the skin or mucosal tissue, as an ointment, lotion, cream, microemulsion, gel, solution or the like, as further described herein, within the context of a dosing regimen effective to bring about the desired result.

Topical formulations comprising one or more nicotinamide mononucleotide based derivative compounds that increase the level of intracellular NAD+ may also be used as preventive, e.g., chemopreventive, compositions. When used in a chemopreventive method, susceptible skin is treated prior to any visible condition in a particular individual.

In certain embodiments, a nicotinamide mononucleotide based derivative compound that increases the level of intracellular NAD+ may be used for treating or preventing a disease or condition induced or exacerbated by cellular senescence in a subject; methods for decreasing the rate of senescence of a subject, e.g., after onset of senescence; methods for extending the lifespan of a subject; methods for treating or preventing a disease or condition relating to lifespan; methods for treating or preventing a disease or condition relating to the proliferative capacity of cells; and methods for treating or preventing a disease or condition resulting from cell damage or death. In certain embodiments, the method does not act by decreasing the rate of occurrence of diseases that shorten the lifespan of a subject. In certain embodiments, a method does not act by reducing the lethality caused by a disease, such as cancer.

In certain embodiments, a nicotinamide mononucleotide based derivative compound that increases the level of intracellular NAD+ may be administered to a subject in order to generally increase the lifespan of its cells and to protect its cells against stress and/or against apoptosis. Treating a subject with a compound described herein may be similar to subjecting the subject to hormesis, i.e., mild stress that is beneficial to organisms and may extend their lifespan.

A nicotinamide mononucleotide based derivative compound that increases the level of intracellular NAD+ can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amyotropic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasis such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure or radiation exposure.

A nicotinamide mononucleotide based derivative compound that increases the level of intracellular NAD+ can also be administered to a subject suffering from an acute disease, e.g., damage to an organ or tissue, e.g., a subject suffering from stroke or myocardial infarction or a subject suffering from a spinal cord injury. A nicotinamide mononucleotide based derivative compound that increases the level of intracellular NAD+ may also be used to repair an alcoholic's liver.

In certain embodiments, the invention provides methods for treating and/or preventing a cardiovascular disease by administering to a subject in need thereof a nicotinamide mononucleotide based derivative compound that increases the level of intracellular NAD+. The benefits of NAD+ in treating cardivasular diseases has been described in several studies, such as Borradaile, et al., "NAD+, Sirtuins, and Cardiovascular Disease" Current Pharmaceutical Design 2016 15(1):110-117.

In other embodiments, provided herein is a method for treating a cardiovascular disease by administering to a subject in need thereof a disclosed compound and/or a pharmaceutical composition thereof. Cardiovascular diseases that can be treated using the disclosed compounds and pharmaceutical compositions thereof include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable using compositions and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated include those related to platelet aggregation, the retinal arterioles, the glomerular arterioles, the vasa nervorum, cardiac arterioles, and associated capillary beds of the eye, the kidney, the heart, and the central and peripheral nervous systems. The disclosed compounds and pharmaceutical compositions thereof may also be used for increasing HDL levels in plasma of an individual.

Yet other disorders that may be treated with a nicotinamide mononucleotide based derivative compound that increases the level of intracellular NAD+ include restenosis, e.g., following coronary intervention, and disorders relating to an abnormal level of high density and low density cholesterol.

The disclosed compounds and pharmaceutical compositions thereof may be administered to subjects who have recently received or are likely to receive a dose of radiation or toxin. In one embodiment, the dose of radiation or toxin is received as part of a work-related or medical procedure, e.g., working in a nuclear power plant, flying an airplane, an X-ray, CAT scan, or the administration of a radioactive dye for medical imaging; in such an embodiment, the compound is administered as a prophylactic measure. In other embodiments, the radiation or toxin exposure is received unintentionally, e.g., as a result of an industrial accident, habitation in a location of natural radiation, terrorist act, or act of war involving radioactive or toxic material. In such a case, the disclosed compounds and pharmaceutical compositions thereof are preferably administered as soon as possible after the exposure to inhibit apoptosis and the subsequent development of acute radiation syndrome.

In some embodiments, the invention relates to the use of a nicotinamide mononucleotide based derivative to prevent adverse effects and protect cells from toxicity. Toxicity may be an adverse effect of radiation or external chemicals on the cells of the body. Examples of toxins are pharmaceuticals, drugs of abuse, and radiation, such as UV or X-ray light. Both radiative and chemical toxins have the potential to damage biological molecules such as DNA. This damage typically occurs by chemical reaction of the exogenous agent or its metabolites with biological molecules, or indirectly through stimulated production of reactive oxygen species (e.g., superoxide, peroxides, hydroxyl radicals). Repair systems in the cell excise and repair damage caused by toxins.

Enzymes that use NAD+ play a part in the DNA repair process. Specifically, the poly(ADP-ribose) polymerases (PARPs), particularly PARP-1, are activated by DNA strand breaks and affect DNA repair. The PARPs consume NAD+ as an adenosine diphosphate ribose (ADPR) donor and synthesize poly(ADP-ribose) onto nuclear proteins such as histones and PARP itself. Although PARP activities facilitate DNA repair, overactivation of PARP can cause significant depletion of cellular NAD+, leading to cellular necrosis. The apparent sensitivity of NAD+ metabolism to genotoxicity has led to pharmacological investigations into the inhibition of PARP as a means to improve cell survival. Numerous reports have shown that PARP inhibition increases NAD+ concentrations in cells subject to genotoxicity, with a resulting decrease in cellular necrosis. See, e.g., Fang, et al., Defective Mitophagy in XPA via PARP-1 Hyperactivation and NAD+/SIRT1 Reduction. Cell 2014 157:882-896. Nevertheless, cell death from toxicity still occurs, presumably because cells are able to complete apoptotic pathways that are activated by genotoxicity. Thus, significant cell death is still a consequence of DNA/macromolecule damage, even with inhibition of PARP. This consequence suggests that improvement of $NAD^+$ metabolism in genotoxicity can be partially effective in improving cell survival but that other proteins that modulate apoptotic sensitivity, such as sirtuins, may also play important roles in cell responses to genotoxins.

Physiological and biochemical mechanisms that determine the effects of chemical and radiation toxicity in tissues are complex, and evidence indicates that NAD+ metabolism is an important aspect of cell stress response pathways. For example, upregulation of NAD+ metabolism, via nicotinamide/nicotinic acid mononucleotide (NMNAT) overexpression, has been shown to protect against neuron axonal degeneration, and nicotinamide used pharmacologically has been recently shown to provide neuron protection in a model of fetal alcohol syndrome and fetal ischemia. Such protective effects could be attributable to upregulated NAD+ biosynthesis, which increases the available NAD+ pool subject to depletion during genotoxic stress. This depletion of NAD+ is mediated by PARP enzymes, which are activated by DNA damage and can deplete cellular NAD+, leading to necrotic death. Another mechanism of enhanced cell protection that could act in concert with upregulated NAD+ biosynthesis is the activation of cell protection transcriptional programs regulated by sirtuin enzymes.

In other embodiments, the disclosed compounds and pharmaceutical compositions thereof may be useful for treating age-related disorders, such as, for example, cancer.

Exemplary cancers that may be treated using the disclosed compounds and pharmaceutical compositions thereof include those of the brain and kidney; hormone-dependent cancers including breast, prostate, testicular, and ovarian cancers; lymphomas, and leukemias. Other diseases that can be treated include autoimmune diseases, e.g., systemic lupus erythematosus, scleroderma, and arthritis, in which autoimmune cells should be removed. Viral infections such as herpes, HIV, adenovirus, and HTLV-1 associated malignant and benign disorders can also be treated by administration of the disclosed compounds and pharmaceutical compositions thereof.

In some embodiments, the disclosed compounds and pharmaceutical compositions thereof can be used to treat patients suffering from neurodegenerative diseases, and traumatic or mechanical injury to the central nervous system (CNS) or peripheral nervous system (PNS). Examples of neurodegenerative diseases include, but are not limited to, Alzheimer's disease (AD), Parkinson's disease (PD), Huntington disease (HD), amyotrophic lateral sclerosis (ALS; Lou Gehrig's disease), diffuse Lewy body disease, choreaacanthocytosis, primary lateral sclerosis, ocular diseases (ocular neuritis), chemotherapy-induced neuropathies (e.g., from vincristine, paclitaxel, bortezomib), diabetes-induced neuropathies and Friedreich's ataxia.

In certain embodiments, the disclosed compounds and pharmaceutical compositions thereof may be used to treat multiple sclerosis (MS), including relapsing MS and monosymptomatic MS, and other demyelinating conditions, such as, for example, chronic inflammatory demyelinating polyneuropathy (CIDP), or symptoms associated therewith.

In some embodiments, the disclosed compounds and pharmaceutical compositions thereof may be used to treat trauma to the nerves, including, trauma due to disease, injury (including surgical intervention), or environmental trauma (e.g., neurotoxins, alcoholism, etc.).

The disclosed compounds and pharmaceutical compositions thereof may also be useful to treat and alleviate symptoms of various peripheral nervous system (PNS) disorders. PNS disorders include a wide range of disorders in which the nerves outside of the brain and spinal cord— peripheral nerves—have been damaged. Peripheral neuropathy may also be referred to as peripheral neuritis, or if many nerves are involved, the terms polyneuropathy or polyneuritis may be used. PNS disorders may be the result of, for example, leprosy, diabetes, Guillain-Barre syndrome, and others.

Other PNS diseases treatable with the disclosed compounds and pharmaceutical compositions thereof include Brachial Plexus Neuropathies: diseases of the cervical and first thoracic roots, nerve trunks, cords, and peripheral nerve components of the brachial plexus. Clinical manifestations include regional pain, paresthesia; muscle weakness, and decreased sensation in the upper extremity. These disorders may be associated with trauma, including birth injuries; thoracic outlet syndrome; neoplasms, neuritis, radiotherapy; and other conditions (see Adams et al. *Principles of Neurology*, 6th ed. pp. 1351-2). Diabetic neuropathies (peripheral, autonomic, and cranial nerve disorders that are associated with diabetes mellitus) usually result from diabetic microvascular injury involving small blood vessels that supply nerves (vasa nervorum). Relatively common conditions which may be associated with diabetic neuropathy include third nerve palsy; mononeuropathy; mononeuropathy multiplex; diabetic amyotrophy; a painful polyneuropathy; autonomic neuropathy; and thoracoabdominal neuropathy (see Adams et al., *Principles of Neurology*, 6th ed., p. 1325); mononeuropathies (disease or trauma involving a single peripheral nerve in isolation, or out of proportion to evidence of diffuse peripheral nerve dysfunction).

Mononeuropathy multiplex refers to a condition characterized by multiple isolated nerve injuries. Mononeuropathies may result from a wide variety of causes, including ischemia; traumatic injury; compression; connective tissue diseases; cumulative trauma disorders; and other conditions; Neuralgia (intense or aching pain that occurs along the course or distribution of a peripheral or cranial nerve); Peripheral Nervous System; and Neoplasms (neoplasms that arise from peripheral nerve tissue). This includes neurofibromas; Schwannomas; granular cell tumors; and malignant peripheral nerve sheath tumors. See DeVita Jr et al., *Cancer: Principles and Practice of Oncology*, 5th ed, pp 750-1). Other causes include Nerve Compression Syndromes (mechanical compression of nerves or nerve roots from internal or external causes). These may result in a conduction block to nerve impulses, due to, for example, myelin sheath dysfunction, or axonal loss. The nerve and nerve sheath injuries may be caused by ischemia; inflammation; a direct mechanical effect; and Neuritis (a general term indicating inflammation of a peripheral or cranial nerve). Clinical manifestation may include pain; paresthesias; paresis; or hyperthesia; and Polyneuropathies (diseases of multiple peripheral nerves). The various forms are categorized by the type of nerve affected (e.g., sensory, motor, or autonomic), by the distribution of nerve injury (e.g., distal vs. proximal), by nerve component primarily affected (e.g., demyelinating vs. axonal), by etiology, or by pattern of inheritance.

Axon degeneration occurs frequently in neurodegenerative diseases and peripheral neuropathies. The degeneration of transected axons is delayed in Wallerian degeneration slow (Wlds) mice with the overexpression of a fusion protein with the nicotinamide adenine dinucleotide (NAD+) synthetic enzyme, nicotinamide mononucleotide adenylyltransferase (Nmnat1). Both Wld(s) and Nmnat1 themselves are functional in preventing axon degeneration in neuronal cultures.

NAD+ levels decrease in injured, diseased, or degenerating neural cells and preventing this NAD+ decline efficiently protects neural cells from cell death. See, Araki & Milbrandt "Increased nuclear NAD+ biosynthesis and SIRT1 activation prevent axonal degeneration" Science. 2004 Aug. 13; 305(5686):1010-3 and Wang et al., "A local mechanism mediates NAD-dependent protection of axon degeneration" J Cell Biol. 170(3):349-55 (2005) hereby incorporated by reference in their entirety. As the nicotinamide mononucleotide based compounds disclosed herein are capable of increasing intracellular levels of NAD+, these compounds are useful as a therapeutic or nutritional supplement in managing injuries, diseases, and disorders affecting the central nervous system and the peripheral nervous system, including, but not limited to, trauma or injury to neural cells, diseases or conditions that harm neural cells, and neurodegenerative diseases or syndromes. The correlation of increased NAD+ synthesis with beneficial outcomes in neural injuries and diseases or conditions has been discussed in, e.g., Stein et al., "Expression of Nampt in Hippocampal and Cortical Excitatory Neurons Is Critical for Cognitive Function" The Journal of Neuroscience 2014 34(17):5800-5815; and Stein et al., "Specific ablation of Nampt in adult neural stem cells recapitulates their functional defects during aging" EMBO J. 2014 33:1321-1340.

Some neurodegenerative diseases, neurodegenerative syndromes, diseases and conditions that harm neural cells, and injury to neural cells are described below.

Essential tremor (ET) is the most common movement disorder. It is a syndrome characterized by a slowly progressive postural and/or kinetic tremor, usually affecting both upper extremities.

Parkinson's disease (PD) is a progressive neurodegenerative disorder associated with a loss of dopaminergic nigrostriatal neurons.

Alzheimer's disease (AD) is the most common form of dementia. It is a progressive degenerative disease of the brain, strongly associated with advanced age. Over time, people with the disease lose their ability to think and reason clearly, judge situations, solve problems, concentrate, remember useful information, take care of themselves, and even speak. A number of neurodegenerative diseases such as Alzheimer's disease execute their biological impact in the brain. It is preferred that nicotinamide mononucleotide based compounds disclosed herein are capable of passing the blood-brain-barrier (BBB).

Huntington's disease (HD) is an incurable, adult-onset, autosomal dominant inherited disorder associated with cell loss within a specific subset of neurons in the basal ganglia and cortex.

Ataxia is defined as an inability to maintain normal posture and smoothness of movement. Neurologic symptoms and signs such as seizures and movement disorders (e.g., dystonia, chorea) may accompany ataxia.

Catatonia is a state of apparent unresponsiveness to external stimuli in a person who is apparently awake.

Epilepsy is defined as a chronic condition characterized by spontaneous, recurrent seizures; seizure is defined as a clinical event associated with a transient, hypersynchronous neuronal discharge.

Neuroleptic malignant syndrome (NMS) refers to the combination of hyperthermia, rigidity, and autonomic dysregulation that can occur as a serious complication of the use of antipsychotic drugs.

Chorea is an involuntary abnormal movement, characterized by abrupt, brief, nonrhythmic, nonrepetitive movement of any limb, often associated with nonpatterned facial grimaces. Chorea gravidarum (CG) is the term given to chorea occurring during pregnancy.

Cortical basal ganglionic degeneration (CBGD) clinical characteristics include progressive dementia, parkinsonism, and limb apraxia. Dysfunction of the central or peripheral nervous system pathways may cause autonomic dysfunction.

Dystonia is a syndrome of sustained muscle contractions, usually producing twisting and repetitive movements or abnormal postures. Writer's cramp is a form of task-specific focal dystonia.

Mental retardation (MR) is a condition in which intellectual capacity is limited significantly. Developmental disability describes a condition that limits an individual's ability to perform activities and roles as expected in a certain social environment. Frequently, MR and developmental disabilities are present simultaneously as a consequence of brain damage.

Neuroacanthocytosis is a progressive neurologic disease characterized by movement disorders, personality changes, cognitive deterioration, axonal neuropathy, and seizures. Most patients have acanthocytosis on peripheral blood smear at some point during the course of the disease.

Pelizaeus-Merzbacher disease (PMD) and X-linked spastic paraplegia type 2 (SPG2) are at opposite ends of a clinical spectrum of X-linked diseases caused by mutations of the same gene, the proteolipid protein 1 (PLP1) gene, and resulting in defective central nervous system (CNS) myelination. Clinical signs usually include some combination of nystagmus, stridor, spastic quadriparesis, hypotonia, cognitive impairment, ataxia, tremor, and diffuse leukoencephalopathy on MRI scans.

Progressive supranuclear palsy (PSP), also known as Steele-Richardson-Olszewski syndrome, is a neurodegenerative disease that affects cognition, eye movements, and posture.

Striatonigral degeneration (SND) is a neurodegenerative disease that represents a manifestation of multiple system atrophy (MSA). The other manifestations are Shy-Drager syndrome (e.g., autonomic failure predominates) and sporadic olivopontocerebellar degeneration (sOPCA, cerebellum predominates).

Ischemic stroke occurs due to a loss of blood supply to part of the brain, initiating the ischemic cascade. Brain tissue ceases to function if deprived of oxygen for more than 60 to 90 seconds and after a few hours will suffer irreversible injury possibly leading to death of the tissue, i.e., infarction. Atherosclerosis may disrupt the blood supply by narrowing the lumen of blood vessels leading to a reduction of blood flow, by causing the formation of blood clots within the vessel, or by releasing showers of small emboli through the disintegration of atherosclerotic plaques. Embolic infarction occurs when emboli formed elsewhere in the circulatory system, typically in the heart as a consequence of atria fibriliation, or in the carotid arteries. These break off, enter the cerebral circulation, then lodge in and occlude brain blood vessels.

Due to collateral circulation within the region of brain tissue affected by ischemia, there is a spectrum of severity. Thus, part of the tissue may immediately die while other parts may only be injured and could potentially recover. The ischemia area where tissue might recover is referred to as the ischemic penumbra.

As oxygen or glucose becomes depleted in ischemic brain tissue, the production of high energy phosphate compounds such as adenine triphosphate (ATP) fails, leading to failure of energy dependent processes necessary for tissue cell survival. This sets off a series of interrelated events that result in cellular injury and death. These include the failure of mitochondria, which can lead further toward energy depletion and may trigger cell death due to apoptosis. Other processes include the loss of membrane ion pump function leading to electrolyte imbalances in brain cells. There is also the release of excitatory neurotransmitters, which have toxic effects in excessive concentrations.

Spinal cord injury, or myelopathy, is a disturbance of the spinal cord that results in loss of sensation and mobility. The two common types of spinal cord injury are: trauma: automobile accidents, falls, gunshots, diving accidents, etc. and disease: polio, spina bifida, tumors, Friedreich's ataxia, etc. It is important to note that the spinal cord does not have to be completely severed for there to be a loss of function. In fact, the spinal cord remains intact in most cases of spinal cord injury.

Traumatic brain injury (TBI), also called intracranial injury, or simply head injury, occurs when a sudden trauma causes brain damage. TBI can result from a closed head injury or a penetrating head injury and is one of two subsets of acquired brain injury (ABI). The other subset is non-traumatic brain injury (e.g., stroke, meningitis, anoxia). Parts of the brain that can be damaged include the cerebral hemispheres, cerebellum, and brain stem. Symptoms of a TBI can be mild, moderate, or severe, depending on the extent of the damage to the brain. Outcome can be anything from complete recovery to permanent disability or death. A coma can also affect a child's brain. The damage from TBI can be focal, confined to one area of the brain, or diffuse, involving more than one area of the brain. Diffuse trauma to the brain is frequently associated with concussion (a shaking of the brain in response to sudden motion of the head), diffuse axonal injury, or coma. Localized injuries may be associated with neurobehavioral manifestations, hemiparesis or other focal neurologic deficits.

Another insult to the brain that can cause injury is anoxia. Anoxia is a condition in which there is an absence of oxygen supply to an organ's tissues, even if there is adequate blood flow to the tissue. Hypoxia refers to a decrease in oxygen supply rather than a complete absence of oxygen, and ischemia is inadequate blood supply, as is seen in cases in which the brain swells. In any of these cases, without adequate oxygen, a biochemical cascade called the ischemic cascade is unleashed, and the cells of the brain can die within several minutes. This type of injury is often seen in near-drowning victims, in heart attack patients (particularly those who have suffered a cardiac arrest), or in people who suffer significant blood loss from other injuries that then causes a decrease in blood flow to the brain due to circulatory (hypovolemic) shock.

The disclosed compounds and pharmaceutical compositions thereof can also be used to treat blood coagulation disorders (or hemostatic disorders). As used interchangeably herein, the terms "hemostasis", "blood coagulation", and "blood clotting" refer to the control of bleeding, including the physiological properties of vasoconstriction and coagulation.

The disclosed compounds also provide anticoagulation and antithrombotic treatments aiming at inhibiting the formation of blood clots in order to treat blood coagulation disorders, such as myocardial infarction, stroke, loss of a limb by peripheral artery disease or pulmonary embolism.

As used interchangeably herein, "modulating or modulation of hemostasis" and "regulating or regulation of hemostasis" includes the induction (e.g., stimulation or increase) of hemostasis, as well as the inhibition (e.g., reduction or decrease) of hemostasis.

In some embodiments, provided herein are methods for reducing or inhibiting hemostasis in a subject by administering a disclosed compound or a pharmaceutical composition comprising the compound. The compounds, compositions and methods disclosed herein are useful for the treatment of thrombotic disorders. As used herein, the term "thrombotic disorder" includes any disorder or condition characterized by excessive or unwanted coagulation or hemostatic activity, or a hypercoagulable state. Examples of thrombotic disorders include, but are not limited to, thromboembolism, deep vein thrombosis, pulmonary embolism, stroke, myocardial infarction, miscarriage, thrombophilia associated with anti-thrombin III deficiency, protein C deficiency, protein S deficiency, resistance to activated protein C, dysfibrinogenemia, fibrinolytic disorders, homocystinuria, pregnancy, inflammatory disorders, myeloproliferative disorders, arteriosclerosis, angina, e.g., unstable angina, disseminated intravascular coagulation, thrombotic thrombocytopenic purpura, cancer metastasis, sickle cell disease, glomerular nephritis, and drug induced thrombocytopenia (including, for example, heparin induced thrombocytopenia).

In addition, the disclosed compounds and pharmaceutical compositions thereof may be administered to reduce thrombotic events or to reduce re-occlusion during or after therapeutic clot lysis or procedures such as angioplasty or surgery.

The disclosed compounds and pharmaceutical compositions thereof may also be used for treating or reducing weight gain or obesity in a subject. For example, the disclosed compounds and pharmaceutical compositions thereof may be used to treat hereditary obesity, dietary obesity, hormone related obesity, obesity related to the administration of medication, to reduce the weight of a subject, or to reduce weight gain in a subject. A subject in need of such a treatment may be a subject who is obese, likely to become obese, overweight, or likely to become overweight. Subjects who are likely to become obese or overweight can be identified, for example, based on family history, genetics, diet, activity level, medication intake, or various combinations thereof.

In other embodiments, the disclosed compounds and pharmaceutical compositions thereof may be administered to subjects suffering from a variety of other diseases and conditions that may be treated by promoting weight loss in the subject. Such diseases include, for example, high blood pressure, hypertension, high blood cholesterol, dyslipidemia, type 2 diabetes, insulin resistance, glucose intolerance, hyperinsulinemia, coronary heart disease, angina pectoris, congestive heart failure, stroke, gallstones, cholecystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), bladder control problems (such as stress incontinence); uric acid nephrolithiasis; psychological disorders (such as depression, eating disorders, distorted body image, and low self-esteem). Stunkard A J, Wadden T A. (Editors) *Obesity: theory and therapy*, Second Edition. New York: Raven Press, 1993. Patients with AIDS can develop lipodystrophy or insulin resistance in response to combination therapies for AIDS.

In other embodiments, the disclosed compounds and pharmaceutical compositions thereof may be used for inhibiting adipogenesis or fat cell differentiation, whether in vitro or in vivo. In particular, high circulating levels of insulin and/or insulin like growth factor (IGF) 1 can be inhibited from recruiting preadipocytes to differentiate into adipocytes. Such methods may be used for treating obesity.

In other embodiments, the disclosed compounds and pharmaceutical compositions thereof may be used for reducing appetite and/or increasing satiety, thereby causing weight loss or avoidance of weight gain. A subject in need of such a treatment may be a subject who is overweight, obese or a subject likely to become overweight or obese.

In other embodiments, the disclosed compounds and pharmaceutical compositions thereof may be used to treat a subject who has cachexia or may be likely to develop cachexia. A method may further comprise monitoring in the subject the state of the disease. Methods for promoting appetite and/or weight gain may include, for example, prior identifying a subject as being in need of decreased fat or lipid metabolism, e.g., by weighing the subject, determining the BMI of the subject. The method may also include monitoring the subject, e.g., during and/or after administration of the disclosed compounds or pharmaceutical compositions thereof. The administering can include one or more dosages, e.g., delivered in boluses or continuously. Monitoring can include evaluating a hormone or a metabolite. Exemplary hormones include leptin, adiponectin, resistin, and insulin. Exemplary metabolites include triglycerides, cholesterol, and fatty acids.

In other embodiments, the disclosed compounds and pharmaceutical compositions thereof may be administered to reduce drug-induced weight gain. For example, the disclosed compounds and pharmaceutical compositions thereof may be administered conjointly with medications that may stimulate appetite or cause weight gain, in particular, weight gain due to factors other than water retention.

Examples of medications that may cause weight gain, include for example, diabetes treatments, including, for example, sulfonylureas (such as glipizide and glyburide), thiazolidinediones (such as pioglitazone and rosiglitazone), meglitinides, nateglinide, repaglinide, sulphonylurea medicines, and insulin; anti-depressants, including, for example, tricyclic antidepressants (such as amitriptyline and imipramine), irreversible monoamine oxidase inhibitors (MAOIs), selective serotonin reuptake inhibitors (SSRIs), bupropion, paroxetine, and mirtazapine; steroids, such as, for example, prednisone; hormone therapy; lithium carbonate; valproic acid; carbamazepine; chlorpromazine; thiothixene; beta blockers (such as propranolol); alpha blockers (such as clonidine, prazosin and terazosin); and contraceptives including oral contraceptives (birth control pills) or other contraceptives containing estrogen and/or progesterone (Depo-Provera, Norplant, Ortho), testosterone, or Megestrol. In exemplary embodiments, the disclosed compounds and pharmaceutical compositions thereof may be administered as part of a smoking cessation program to reduce weight gain or reduce weight already gained.

In some embodiments, the disclosed compounds and pharmaceutical compositions thereof may be used for treating a metabolic disorder, such as insulin-resistance, a pre-diabetic state, type II diabetes, and/or complications thereof.

Administration of the disclosed compounds and pharmaceutical compositions thereof may increase insulin sensitivity and/or decrease insulin levels in a subject. A subject in need of such a treatment may be a subject who has insulin resistance or other precursor symptom of type II diabetes, who has type II diabetes, or who is likely to develop any of these conditions. For example, the subject may be a subject having insulin resistance, e.g., having high circulating levels of insulin and/or associated conditions, such as hyperlipidemia, dyslipogenesis, hypercholesterolemia, impaired glucose tolerance, high blood glucose sugar level, other manifestations of syndrome X, hypertension, atherosclerosis, and lipodystrophy.

Provided herein is a process for regulating the concentration of blood glucose in a mammal. As utilized herein, regulating the concentration of blood glucose refers to any increase, decrease, and/or maintenance in or of the concentration of blood glucose as compared to a previously determined level.

Compounds of the present invention may be administered to a mammal in need of such treatment. For example, the mammal may require an increase in blood glucose concentration. Alternatively, the mammal may require a decrease in blood glucose concentration. Or, the mammal may require maintenance of blood glucose concentration above, at, or below a particular level or within a particular range (e.g., through a series of increases and/or decreases, or through no increases or decreases). The blood glucose concentration-regulating compounds may also be administered to a mammal as a prophylactic measure; that is, the mammal is in need of treatment to prevent or delay the occurrence or onset of a medical condition such as, for example, type 1 or type 2 diabetes.

The ability to regulate the concentration of blood glucose in a mammal according to the processes described herein (e.g., by administering to a mammal a blood glucose regulating amount of a compound of the present invention may be advantageous in the treatment and/or prevention of a variety of complications, diseases, and/or illnesses. The role of increased NAD$^+$ levels on metabolic diseases and conditions has been described in, for example, Yoshino et al., "Nicotinamide mononucleotide, a key NAD+ intermediate treats the pathophysiology of diet-and age-induced diabetes" Cell Metab. 2011 14:528-536; and Garten, et al., "Nampt: Linking NAD biology, metabolism, and cancer" Trends Endocrinol Metab. 2009 20(3):130-138. In general, the present invention may be utilized to treat a variety of acute, intermediate stage, and chronic conditions that may be affected by systemic NAD biosynthesis either directly or indirectly.

For example, the regulation of blood glucose concentration may be effective in the treatment and/or prophylaxis of such medical conditions as brain ischemia-induced hypoglycemia, hypoglycemic brain injury caused by, e.g., congenital hyperinsulinism in children, and/or other conditions that severely reduce blood glucose levels. Alternatively, the regulation of blood glucose concentration may be effective in counteracting the effects of the injection of an excessive amount of insulin, or an insufficient dietary or vitamin intake (e.g., deficiencies in vitamin B3 (niacin, which is derived from nicotinic acid and nicotinamide) can result in pellagra, the classic niacin deficiency disease, characterized by bilateral dermatitis, diarrhea, and dementia).

Further, regulation of blood glucose concentration may be effective in the treatment and/or prophylaxis of hypoglycemia, hyperglycemia, impaired glucose tolerance, impaired fasting glucose, and type 1 and type 2 diabetes.

The regulation of blood glucose concentration according to the methods described herein may also be advantageous in counteracting the effects of blood glucose concentration-decreasing drugs such as acetaminophen, alcohol, anabolic steroids, clofibrate, disopyramide, gemfibrozil, monoamine oxidase inhibitors (MAOIs), pentamidine, or sulfonylurea medications (such as glipizide, glyburide, and glimepiride).

Other conditions having a plausible connection to NAD biosynthesis, such as dementia, may also be beneficially treated and/or prevented by blood glucose regulation. See, e.g., Guest, et al., "Changes in Oxidative Damage, Inflammation and [NAD(H)] with Age in Cerebrospinal Fluid" PLOS One. January 2014 9(1): e85335.

The increase, decrease, and/or maintenance of blood glucose concentration can be quantified, for example, by percentage above, below, or in between one or more previously determined levels, or can be quantified by a particular blood glucose concentration or a range thereof.

For example, the blood glucose concentration may be increased to at least about 5% above a previously determined level; to at least about 10% above a previously determined level; to at least about 25% above a previously determined level; to at least about 50% above a previously determined level; to at least about 75% above a previously determined level; to at least about 100% above a previously determined level; to at least about 150% above a previously determined level; or to at least about 200% above a previously determined level. By way of another example, the blood glucose concentration may be decreased to at least about 5% below a previously determined level; to at least about 10% below a previously determined level; to at least about 25% below a previously determined level; to at least about 50% below a previously determined level; to at least about 75% below a previously determined level; to at least about 100% below a previously determined level; to at least about 150% below a previously determined level; or to at least about 200% below a previously determined level. By way of yet another example, the blood glucose concentration may be maintained (e.g., by a series of increases and/or decreases, or by no increases and/or decreases) at a concentration that is no more than about 50% greater or about 50% less than a previously determined level; e.g., no more than about 40% greater or about 40% less; no more than about 30% greater or about 30% less; no more than about 20% greater or about 20% less; no more than about 10% greater or about 10% less; or no more than about 5% greater or about 5% less.

Alternatively, the blood glucose concentration may be maintained (e.g., by a series of increases and/or decreases, or by no increases and/or decreases) at, above, or below a particular blood glucose concentration or within a desired range of blood glucose concentrations. For example, the blood glucose concentration may be maintained at a concentration of greater than about 60 mg/dL; greater than about 70 mg/dL; greater than about 100 mg/dL; greater than about 110 mg/dL; or greater than about 125 mg/dL. Alternatively, the blood glucose concentration may be maintained at a concentration of less than about 200 mg/dL; less than about 175 mg/dL; less than about 150 mg/dL; less than about 125 mg/dL; less than about 110 mg/dL; or less than about 100 mg/dL. By way of another example, the blood glucose concentration may be maintained at a concentration of from about 60 mg/dL to about 140 mg/dL; from about 90 mg/dL to about 130 mg/dL; from about 100 mg/dL to about 125 mg/dL; or from about 110 mg/dL to about 125 mg/dL.

The disclosed compounds and pharmaceutical compositions thereof can also be used to treat a disease or disorder associated with inflammation. Exemplary inflammatory conditions include, for example, multiple sclerosis, rheumatoid arthritis, psoriatic arthritis, degenerative joint disease, spondouloarthropathies, gouty arthritis, systemic lupus erythematosus, juvenile arthritis, rheumatoid arthritis, osteoarthritis, osteoporosis, diabetes (e.g., insulin dependent diabetes mellitus or juvenile onset diabetes), menstrual cramps, cystic fibrosis, inflammatory bowel disease, irritable bowel syndrome, Crohn's disease, mucous colitis, ulcerative colitis, gastritis, esophagitis, pancreatitis, peritonitis, Alzheimer's disease, shock, ankylosing spondylitis, gastritis, conjunctivitis, pancreatitis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, vasculitis, thermal injury (i.e., sunburn), necrotizing enterocolitis, granulocyte transfusion associated syndrome, and/or Sjogren's syndrome. Exemplary inflammatory conditions of the skin include, for example, eczema, atopic dermatitis, contact dermatitis, urticaria, scleroderma, psoriasis, and dermatosis with acute inflammatory components.

In other embodiments, the disclosed compounds and pharmaceutical compositions thereof may be used to treat allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, the disclosed compounds and pharmaceutical compositions thereof may be used to treat autoimmune diseases and/or inflammation associated with autoimmune diseases such as organ-tissue autoimmune diseases (e.g., Raynaud's syndrome), scleroderma, myasthenia gravis, transplant rejection, endotoxin shock, sepsis, psoriasis, eczema, dermatitis, multiple sclerosis, autoimmune thyroiditis, uveitis, systemic lupus erythematosus, Addison's disease, autoimmune polyglandular disease (also known as autoimmune polyglandular syndrome), and Grave's disease.

The circadian clock is encoded by a transcription-translation feedback loop that synchronizes behavior and metabolism with the light-dark cycle. It has been unexpectedly discovered that both the rate-limiting enzyme in mammalian NAD+ biosynthesis, nicotinamide phosphoribosyltransferase (NAMPT), and levels of NAD+, display circadian oscillations which are regulated by the core clock machinery in mice. Inhibition of NAMPT promotes oscillation of the clock gene Per2 by releasing CLOCK:BMAL1 from suppression by SIRT1. In turn, the circadian transcription factor CLOCK binds to and up-regulates Nampt, thus completing a feedback loop involving NAMPT/NAD$^-$ and SIRT1/CLOCK:BMAL1. See, e.g., Ramsey et al., "Circadian clock feedback cycle through NAMPT-mediated NAD+ biosynthesis" Science 2009 324:651-654.

Thus, the periodic variation in NAMPT-mediated NAD+ biosynthesis suggests that it impacts physiologic cycles and possibly the sleep-wake and fasting-feeding cycle. Without being bound by a single theory, it is believed that NAD+ serves as a critical "metabolic oscillator" for the rhythmic regulation of response to environmental cues through control of SIRT1 activity. Compounds disclosed herein may be used to affect a circadian feedback loop through NAMPT-mediated NAD+ biosynthesis and/or a pathway underlying the temporal coupling of metabolic, physiologic, and circadian cycles in mammals.

The recognition of a regulatory pathway involving NAMPT/NAD-SIRT1/CLOCK:BMAL1 has broad implications for understanding how physiologic and behavioral cycles are coordinated with the environmental light-dark cycle. For instance, during sleep, when animals are normally quiescent and fasting, the levels of NAMPT steadily increase, peaking at the beginning of the wakefulness period and coinciding with feeding. As a result of the increase in NAMPT, $NAD^+$ rises to stimulate SIRT1, which orchestrates an appropriate metabolic response in liver involving a switch from catabolic to anabolic pathways.

In certain embodiments, the present invention provides methods for regulation of the core clock machinery (sometimes also referred to as the circadian clock) of a mammal, thereby affecting behaviors, activities, and/or biological functions that occur in or are affected by a diurnal or circadian cycle and that are regulated, at least in part, by the circadian clock. Generally, the methods involve the administration of a therapeutic or prophylactic amount of a circadian clock-regulating compound to a patient or mammal in need of regulation of the circadian clock.

The methods of treatment disclosed herein are generally directed to methods of regulating the circadian clock, thereby regulating or affecting biological functions that are regulated by (sometimes also said to be affected by, affiliated with, or mediated by) the activity of the circadian clock. Typically, these biological functions display a pattern of activity and inactivity that is generally repeated approximately every 24 hours, oscillating between "active" and "inactive" states during the 24 hour period.

Thus, the present invention provides methods of regulating the activity of the circadian clock by administering to a mammal in need thereof a circadian-clock regulating compound. Generally, the regulation of the activity of the circadian clock is the result of the regulation of CLOCK:BMAL1, which is achieved according to the present methods by regulating the activity of SIRT1. The activity of SIRT1 is generally regulated according to the present methods by administration of a circadian clock-regulating compound, and in certain embodiments, by administration of a compound that affects the $NAD^+$ pathway. The regulation of the circadian clock thereby permits regulation of activities mediated by the circadian clock.

According to the present invention, the activity of the circadian clock may be increased, decreased, or maintained by the administration of a circadian clock-regulating compound. Accordingly, biological functions (sometimes also referred to as biological activities) that are regulated by the activity of the circadian clock may also be increased, decreased, or maintained. In addition, these biological functions may also be time shifted; that is to say, an activity that typically occurs during a particular period, such as for example, during daytime or daylight hours (sometimes also referred to as the light cycle) or during the night or nighttime hours (sometimes also referred to as the dark cycle) may be shifted such that the activity occurs during the dark or light cycle, respectively, instead.

Any of a number of biological functions that are typically affected by the activity of the circadian clock may be regulated by the methods of the present invention. Thus, the present methods may be used to treat disorders or disease states that are the result of, for example, the irregular, inadequate, or pathological function of the circadian clock. Similarly, the present methods may be used to treat disorders or symptomatology caused by exogenous factors that affect the proper function or activity of the circadian clock or that require a "resetting" of the clock. For example, administration of circadian clock-regulating compound to a patient experiencing a metabolic disorder provides therapeutic benefit not only when the patient's serum NMN or NAD level is increased, but also when an improvement is observed in the patient with respect to other disorders that accompany the metabolic disorder, like weight loss or gain. In some treatment regimens, the circadian clock-regulating compound of the invention may be administered to a patient at risk of developing a disorder as described herein or to a patient reporting one or more of the physiological symptoms of such a disorder, even though a diagnosis of a metabolic disorder may not have been made.

Examples of disorders, disease states, or symptomatology that may be treated according to the methods of the present invention include, but are not limited to, travel to or across one or more time zones, a change in work shifts, night shift work, or a change in the physical status of a mammal caused by, for example, pregnancy or administration of medications of any kind. Accordingly, the methods of the present invention may be used to treat or prevent disorders, symptoms of disorders, or symptoms caused by exogenous factors. Such disorders and symptoms may include, for example, metabolic disorders, such as improper cycling or timing of feeding and fasting cycles, hyperglycemia, hypoglycemia, or diabetes; sleep disorders, such as insomnia, advanced sleep phase syndrome, delayed sleep phase syndrome, inconsistent sleep/wake cycles, or narcolepsy or to improve wakefulness in individuals suffering from excessive sleepiness; and symptoms caused by exogenous factors, such as, travel to or across one or more time zones (jet lag), shifting into or out of daylight savings time, a change in work shifts or night shift work, pregnancy, or medications being taken for unrelated diseases or disorders.

Accordingly, in certain embodiments, the present invention is directed to a method of regulating a biological function in a mammal, the function being affected by the circadian clock. The method comprises administering a therapeutic or prophylactic (sometimes also referred to as a circadian clock-regulating) amount of a circadian clock-regulating compound to the mammal. The biological function can be, for example, any one of the biological functions described herein. In certain embodiments, the invention comprises a method of treating a metabolic disorder in a mammal and comprises administering a therapeutic or prophylactic amount of a circadian clock-regulating compound to the mammal. In other embodiments, the invention comprises a method of treating a disorder in a mammal mediated by the function of the circadian clock and comprises administering a therapeutic or prophylactic amount of a circadian clock-regulating compound to the mammal. According to any one of these embodiments, the circadian clock-regulating compound may be, for example, nicotinamide, nicotinamide mononucleotide (NMN), nicotinamide adenine dinucleotide (NAD); salts and prodrugs thereof; nicotinamide phosphoribosyltransferase (NAMPT); and combinations thereof, as described in greater detail below. In other embodiments, the circadian clock-regulating compound may be an antagonist of any one of the compounds listed above, thereby exacting an effect opposite that of nicotinamide, nicotinamide mononucleotide (NMN), nicotinamide adenine dinucleotide (NAD); salts and prodrugs thereof, nicotinamide phosphoribosyltransferase (NAMPT); and combinations thereof.

In certain embodiments, the present invention is directed to a method of regulating metabolic activity of a mammal comprising administering to the mammal a therapeutic amount of a circadian clock-regulating compound. In certain embodiments, the metabolic activity of the mammal is increased. In other embodiments, the metabolic activity is decreased. In yet other embodiments, the metabolic activity of the mammal is maintained at a desired level, thereby preventing fluctuations in activity/inactivity. In still other embodiments, the metabolic activity is caused to occur in the light cycle (as opposed to its typical occurrence in the dark cycle). In other embodiments, the metabolic activity is caused to occur in the dark cycle (as opposed to its typical occurrence in the light cycle). In certain embodiments, the circadian clock-regulating compound is administered to the mammal in order to increase the anabolic activity of the liver (e.g., increase the activity of the metabolic pathways of the liver or shift or switch liver activity from catabolism to anabolism). In other embodiments, the circadian clock-regulating compound is administered to the mammal in order to increase the catabolic activity of the liver (e.g., decrease the activity of the metabolic process).

The disclosed compounds and pharmaceutical compositions thereof may also be used for reducing the incidence or severity of flushing and/or hot flashes which are symptoms of a disorder. In certain embodiments, the disclosed compounds and pharmaceutical compositions thereof may be used to reduce flushing side effects of a vasodilator or an antilipemic agent (including anticholesteremic agents and lipotropic agents).

In other embodiments, the method involves the use of the disclosed compounds and pharmaceutical compositions thereof to reduce flushing side effects of antidepressants or anti-psychotic agent. For instance, the disclosed compounds and pharmaceutical compositions thereof can be used conjointly with a serotonin reuptake inhibitor, a 5HT2 receptor antagonist, an anticonvulsant, a norepinephrine reuptake inhibitor, an alpha-adrenorecep tor antagonist, an NK-3 antagonist, an NK-1 receptor antagonist, a PDE4 inhibitor, an Neuropeptide Y5 Receptor Antagonists, a D4 receptor antagonist, a 5HT1A receptor antagonist, a 5HT1D receptor antagonist, a CRF antagonist, a monoamine oxidase inhibitor, or a sedative-hypnotic drug.

In certain embodiments, the disclosed compounds and pharmaceutical compositions thereof may be used as part of a treatment conjointly with a serotonin reuptake inhibitor (SRI) to reduce flushing. In certain preferred embodiments, the SRI is a selective serotonin reuptake inhibitor (SSRI), such as a fluoxetinoid (fluoxetine, norfluoxetine) or anefazodonoid (nefazodone, hydroxynefazodone, oxonefazodone). Other exemplary SSRIs include duloxetine, venlafaxine, milnacipran, citalopram, fluvoxamine, paroxetine and sertraline. The disclosed compounds and pharmaceutical compositions thereof can also be used as part of a treatment conjointly with sedative-hypnotic drug, such as selected from a benzodiazepine (such as alprazolam, chlordiazepoxide, clonazepam, chlorazepate, clobazam, diazepam, halazepam, lorazepam, oxazepam and prazepam), Zolpidem, and barbiturates. In other embodiments, the disclosed compounds and pharmaceutical compositions thereof may be used as part of a treatment conjointly with a 5-HT1A receptor partial agonist, such as selected from buspirone, flesinoxan, gepirone and ipsapirone. The disclosed compounds and pharmaceutical compositions thereof can also be used as part of a treatment conjointly with a norepinephrine reuptake inhibitor, such as selected from tertiary amine tricyclics and secondary amine tricyclics. Exemplary tertiary amine tricyclics include amitriptyline, clomipramine, doxepin, imipramine and trimipramine. Exemplary secondary amine tricyclics include amoxapine, desipramine, maprotiline, nortriptyline and protriptyline. In certain embodiments, the disclosed compounds and pharmaceutical compositions thereof may be used as part of a treatment conjointly with a monoamine oxidase inhibitor, such as selected from isocarboxazid, phenelzine, tranylcypromine, selegiline and moclobemide.

In other embodiments, the disclosed compounds and pharmaceutical compositions thereof may be used to reduce flushing side effects of chemotherapeutic agents, such as cyclophosphamide, and tamoxifen.

In other embodiments, the disclosed compounds and pharmaceutical compositions thereof may be used to reduce flushing side effects of calcium channel blockers, such as amlodipine. In other embodiments, the disclosed compounds and pharmaceutical compositions thereof may be used to reduce flushing side effects of antibiotics. For example, the disclosed compounds and pharmaceutical compositions thereof can be used conjointly with levofloxacin. Levofloxacin is used to treat infections of the sinuses, skin, lungs, ears, airways, bones, and joints caused by susceptible bacteria.

The disclosed compounds and pharmaceutical compositions thereof may be used for treating viral infections (such as infections by influenza, herpes or papilloma virus) or as antifungal agents.

In addition to regulating circadian rhythms and protect neural cells from cell death, sirtuins such as SIRT3, SIRT4, and SIRT5 are found in mitochondria. SIRT3 is expressed at high levels in metabolically active tissue. Modulation of SIRT3 has a variety of physiological applications for muscle cells including mimicking calorie restriction or exercise, increasing mitochodrial biogenesis or metabolism, sensitizing a cell to glucose uptake, increasing fatty acid oxidation, and decreasing reactive oxygen species. In addition, SIRT3 is demonstrated herein to be involved in promoting cell survival during genotoxic stress. Thus modulation of SIRT3 levels also has applications in mediating cell survival.

Increasing the protein or activity level of SIRT3 in a muscle cell can mimic the benefits of calorie restriction or exercise. In some embodiments, the invention relates to methods for increasing mitochondrial biogenesis or metabolism or for boosting mitochondrial activity/endurance in a muscle cell by contacting a muscle cell with an agent IS that increases the protein or activity level of SIRT3 in the cell. In some embodiments, the invention relates to methods for sensitizing a muscle cell to glucose uptake by contacting a muscle cell with an agent that increases the protein or activity level of SIRT3 in the cell. Further embodiments of the invention relate to methods for increasing fatty acid oxidation in a muscle cell by contacting a muscle cell with an agent that increases the protein or activity level of SIRT3 in the cell. Some embodiments of the invention relate to methods for decreasing reactive oxygen species (ROS) in a muscle cell by contacting the muscle cell with an agent that increases the protein or activity level of SIRT3 in the cell.

Increasing levels of SIRT3 benefits many diseases and disorders affected by metabolism within mitochondria. Increasing SIRT3 may be useful in any subjects in need of metabolic activation of one or more of their muscles, e.g., smooth muscles or cardiac muscles or muscle cells thereof. A subject may be a subject having cachexia or muscle wasting.

Increasing SIRT3 may also be used to increase or maintain body temperature, e.g., in hypothermic subjects. Alternatively, inhibiting SIRT3 may be used to reduce body temperature, e.g., in subjects having fever or hyperthermia.

Generally, activation of SIRT3 may be used to stimulate the metabolism of any type of muscle, e.g., muscles of the gut or digestive system, or the urinary tract, and thereby may be used to control gut motility, e.g., constipation, and incontinence.

Other embodiments in which it would be useful to increase SIRT3 include repair of muscle, such as after a surgery or an accident, increase of muscle mass; and increase of athletic performance.

Thus the invention provides methods in which beneficial effects are produced by contacting one or more muscle cells with an agent that increases the protein or activity level of SIRT3 in the cell. These methods effectively facilitate, increase or stimulate one or more of the following: mimic the benefits of calorie restriction or exercise in the muscle cell, increase mitochondrial biogenesis or metabolism, increase mitochondrial activity and/or endurance in the muscle cell, sensitize the muscle cell to glucose uptake, increase fatty acid oxidation in the muscle cell, decrease reactive oxygen species (ROS) in the muscle cell, increase PGC-1a and/or ucp3 and/or GLUT4 expression in the muscle cell, and activate AMP activated protein kinase (AMPK) in the muscle cell.

Various types of muscle cells can be contacted in accordance with the invention. In some embodiments, the muscle cell is a skeletal muscle cell. In certain embodiments, the muscle cell is a cell of a slow-twitch muscle, such as a soleus muscle cell. The methods of the invention include, in some embodiments, administering, to a subject in need of such treatment, an agent that increases the protein or activity level of SIRT3 in cells of the subject.

The cell that is contacted or the subject that is treated in the aforementioned methods preferably is a cell in need of SIRT3 increase in protein or activity level. In certain embodiments, the cell is a diseased cell of a subject.

Also provided are methods for regulating skeletal muscle metabolism or skeletal muscle energy homeostasis in a subject. In such methods, an agent that modulates the protein or activity level of SIRT3 in the subject, i.e., the SIRT3 modulators described herein, is administered to a subject in need thereof.

Also provided are methods for increasing the protein level of SIRT3 in a muscle cell or in muscles of a subject. Such methods include subjecting a cell or a subject to caloric restriction or fasting, or administering to a subject in need thereof an agent that increases the protein or activity level of SIRT3 in a muscle cell. Diseases, disorders and conditions in which such methods are useful include mitochondrial diseases, metabolic disorders, neurologic disorders, muscular disorders, cardiovascular diseases, and excessive weight or obesity. Specific metabolic disorders, diseases or conditions include insulin resistance, diabetes, diabetes related conditions or disorders, or metabolic syndrome. Other metabolic disorders will be known to the skilled person.

Mitochondrial diseases that can be treated include diseases that show a variety of symptoms caused by dysfunction of mitochondria in cells. The mitochondrial diseases may be classified in various ways by biochemical abnormalities, clinical symptoms or types of DNA abnormalities. Types named as KSS (chronic progressive external ophthalmoplegia), MERRF (myoclonus epilepsy associated with ragged-red fibers; Fukuhara syndrome), MELAS, Leber's disease, Leigh encephalopathia and Pearson's disease are widely known. Among them, MELAS is a type mainly showing stroke-like episodes, occupies 30% or more of the whole and is believed to be the most frequent type in the mitochondrial disease.

Methods of treating a mitochondria-related disease or condition in a subject also are disclosed. The methods can include administering to the subject a therapeutically effective amount of a disclosed compound or pharmaceutical composition as provided herein. In one embodiment, the mitochondrial-related disease or disorder includes, but is not limited to, Alpers's Disease, CPEO-Chronic progressive external ophthalmoplegia, Kearns-Sayra Syndrome (KSS), Leber Hereditary Optic Neuropathy (LHON), MELAS-mitochondrial myopathy, encephalomyopathy, lactic acidosis, and stroke-like episodes, MERRF-myoclonic epilepsy and ragged-red fiber disease, NARP-neurogenic muscle weakness, ataxia, and retinitis pigmentosa, Pearson Syndrome, platinum-based chemotherapy induced ototoxicity, Cockayne syndrome, xeroderma pigmentosum A, Wallerian degeneration, and HIV-induced lipodystrophy.

In some embodiments, the mitochondrial-related disease or disorder is a muscle structure disorder, a neuronal activation disorder, a muscle fatigue disorder, a muscle mass disorder, a metabolic disease, a cancer, a vascular disease, an ocular vascular disease, a muscular eye disease, or a renal disease.

In certain embodiments, the muscle structure disorder is selected from Bethlem myopathy, central core disease, congenital fiber type disproportion, distal muscular dystrophy (MD), Duchenne & Becker MD, Emery-Dreifuss MD, facioscapulohumeral MD, hyaline body myopathy, limb-girdle MD, a muscle sodium channel disorders, myotonic chondrodystrophy, myotonic dystrophy, myotubular myopathy, nemaline body disease, oculopharyngeal MD, or stress urinary incontinence.

In other embodiments, the neuronal activation disorder is selected from amyotrophic lateral sclerosis, Charcot-Marie-Tooth disease, Guillain-Barre syndrome, Lambert-Eaton syndrome, multiple sclerosis, myasthenia gravis, nerve lesion, peripheral neuropathy, spinal muscular atrophy, tardy ulnar nerve palsy, and toxic myoneural disorder.

In other embodiments, the muscle fatigue disorder is selected from chronic fatigue syndrome, diabetes (type I or II), glycogen storage disease, fibromyalgia, Friedreich's ataxia, intermittent claudication, lipid storage myopathy, MELAS, mucopolysaccharidosis, Pompe disease, or thyrotoxic myopathy; the muscle mass disorder is cachexia, cartilage degeneration, cerebral palsy, compartment syndrome, critical illness myopathy, inclusion body myositis, muscular atrophy (disuse), sarcopenia, steroid myopathy, and systemic lupus erythematosus.

In other embodiments, the beta oxidation disease is selected from systemic carnitine transporter, carnitine palmitoyltransferase (CPT) II deficiency, very long-chain acyl-CoA dehydrogenase (LCHAD or VLCAD) deficiency, trifunctional enzyme deficiency, medium-chain acyl-CoA dehydrogenase (MCAD) deficiency, short-chain acyl-CoA dehydrogenase (SCAD) deficiency, and ribo flavin-responsive disorders of β-oxidation (RR-MADD).

In other embodiments, the metabolic disease is selected from hyperlipidemia, dyslipidemia, hypercholesterolemia, hypertriglyceridemia, HDL hypocholesterolemia, LDL hypercholesterolemia and/or HLD non-cholesterolemia, VLDL hyperproteinemia, dyslipoproteinemia, apo lipoprotein A-I hypoproteinemia, atherosclerosis, disease of arterial sclerosis, disease of cardiovascular systems, cerebrovascular disease, peripheral circulatory disease, metabolic syndrome, syndrome X, obesity, diabetes (type I or II), hyperglycemia, insulin resistance, impaired glucose tolerance, hyperinsulinism, diabetic complication, cardiac insufficiency, cardiac infarction, cardiomyopathy, hypertension, Nonalcoholic fatty liver disease (NAFLD), Nonalcoholic steatohepatitis (NASH), thrombus, Alzheimer disease, neurodegenerative disease, demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, and pancreatitis.

In other embodiments, the vascular disease is selected from peripheral vascular insufficiency, peripheral vascular disease, intermittent claudication, peripheral vascular disease (PVD), peripheral artery disease (PAD), peripheral artery occlusive disease (PAOD), and peripheral obliterative arteriopathy.

In other embodiments, the ocular vascular disease is selected from age-related macular degeneration (AMD), stargardt disease, hypertensive retinopathy, diabetic retinopathy, retinopathy, macular degeneration, retinal haemorrhage, and glaucoma.

In other embodiments, the muscular eye disease is selected from strabismus, progressive external ophthalmoplegia, esotropia, exotropia, a disorder of refraction and accommodation, hypermetropia, myopia, astigmatism, anisometropia, presbyopia, a disorders of accommodation, and internal ophthalmoplegia.

In other embodiments, the renal disease is selected from glomerulonephritis, glomerulosclerosis, nephrotic syndrome, hypertensive nephrosclerosis, acute nephritis, recurrent hematuria, persistent hematuria, chronic nephritis, rapidly progressive nephritis, acute renal failure (also known as acute kidney injury), chronic renal failure, diabetic nephropathy, and Bartter's syndrome.

In other embodiments, the mitochondrial-related disease is cancer. Examples of such cancer include, but are not limited to, cancers of the colon, large intestine, skin, breast, prostate, ovary, and/or lung.

In certain embodiments, the mitochondrial-related disease or condition is selected from genetic lipodystrophy, non-alcoholic fatty liver disease (NAFLD), non-alcoholic steatohepatitis (NASH), renal ischemia/reperfusion injury (IRI), Duchenne & Becker muscular dystrophy, diabetes (type I or type II), obesity, and sarcopenia.

Photoreceptor neuronal cell death and vision can be rescued by NMN administration. In certain embodiments, nicotinamide phosphoribosyl transferase (NAMPT)-mediated NAD biosynthesis can play a role in for rod and/or cone PR neuron survival. In certain embodiments, decreased NAD levels can cause impaired mitochondrial function in PR neurons, alterations in TCA cycle metabolites, and can lead to cell death and blindness.

Deleting NAMPT can lead to photoreceptor death, loss of normal retinal structure and function, and vision loss. In some cases, damage to photoreceptor neurons and their function can be reversed with supplementation of NMN, an NAMPT enzymatic reaction product. Disclosed herein are methods of administering NMN to restore NAD levels in the retina. In some embodiments, NMN supplementation can be an effective therapeutic intervention for many retinal degenerative diseases.

Provided herein are methods of treating, preventing, and reducing risk of diseases associated with photoreceptor dysfunction, including, without limitation, age-related macular degeneration (AMD), inherited and acquired retinal diseases such as, without limitation, retinitis pigmentosa (RP), rod and cone dystrophism, and Leber's congenital amaurosis (LCA) by administration of NMN to a subject. In certain embodiments, NMN administration can be an effective intervention for the prevention and/or treatment of orphan retinal degenerative diseases including but not limited to rod dystrophy, cone dystrophy, retinitis pigmentosa, other inherited retinal degenerations, Leber's congenital amaurosis (LCA) and acquired retinal degenerations such as, but not limited to, age-related macular degeneration, photoreceptor degeneration following retinal detachment.

In some embodiments, these methods can comprise administering to a subject a pharmaceutically effective amount of nicotinamide mononucleotide (NMN). In some embodiments, a pharmaceutically effective amount of nicotinamide mononucleotide (NMN) can be an amount effective for increasing retinal NAD levels.

Disclosed herein are methods of treating macular degeneration in a subject. In some embodiments, the methods include treating aberrant retinal NAD levels in a subject, including aberrantly low retinal NAD levels. These methods comprise administering NMN to a subject. In some embodiments, the methods include treating retinal degeneration in a subject. In some embodiments, the methods include treating photoreceptor damage in a subject. In some embodiments, the methods include treating photoreceptor degeneration in a subject.

In some embodiments, the methods include treating vision loss associated with retinal degeneration in a subject. In some embodiments, the methods include treating aberrant retinal structure in a subject. In some embodiments, the methods include increasing retinal NAD levels in a subject.

In some embodiments, the methods include reducing the risk of developing macular degeneration in a subject. In some embodiments, the methods include reducing risk of developing aberrant retinal NAD levels in a subject. In some embodiments, the methods include reducing the risk of developing retinal degeneration in a subject. In some embodiments, the methods include reducing the risk of developing photoreceptor damage/degeneration in a subject. In some embodiments, the methods include reducing the risk of developing vision loss associated with retinal degeneration in a subject. In some embodiments, the methods include reducing the risk of developing aberrant retinal structure in a subject.

In some embodiments, the methods include treating a retina disease in a subject. In some embodiments, a retinal disease that can be treated by administration of NMN can be retinitis pigmentosa (RP), Leber's congenital amaurosis (LCA), rod dystrophy, cone dystrophy, rod-cone dystrophy, cone-rod dystrophy, age-related macular degeneration, photoreceptor degeneration following retinal detachments, or a combination thereof.

Also disclosed herein are methods of treating a disease or disorder that would benefit from increased $NAD^+$ levels, for example by increasing in vivo levels of $NAD^+$ (e.g., intracellular $NAD^+$ levels, levels of $NAD^+$ in tissues or plasma, and/or overall $NAD^+$ levels in an organism). In some embodiments, provided herein are uses of a compound of Formula (I), (II), (III), (IV), or (V), or a pharmaceutically acceptable salt thereof, or a pharmaceutical composition comprising the compound, for the preparation of a medicament for promoting survival of a eukaryotic cell by modulating $NAD^+$ activity.

In certain embodiments, provided herein is a compound of Formula (I), (II), (III), (IV), or (V), or a pharmaceutically acceptable salt thereof, or a pharmaceutical composition comprising the compound, for use in promoting survival of a eukaryotic cell by modulating $NAD^+$ activity.

In some embodiments, provided herein are uses of a compound of Formula (I), (II), (III), (IV), or (V), or a pharmaceutically acceptable salt thereof, or a pharmaceutical composition comprising the compound, for the preparation of a medicament for treating or preventing a disease or disorder associated with cell death, cell dysfunction, or aging.

In some embodiments, provided herein is a compound of Formula (I), (II), (III), (IV), or (V), or a pharmaceutically acceptable salt thereof, or a pharmaceutical composition comprising the compound, for use in treating or preventing a disease or disorder associated with cell death, cell dysfunction, or aging.

In some embodiments, provided herein are uses for a compound of Formula (I), (II), (III), (IV), or (V), or a pharmaceutically acceptable salt thereof, or a pharmaceutical composition comprising the compound, for the preparation of a medicament for treating or preventing insulin resistance, a metabolic syndrome, hypercholesterolemia, atherogenic dyslipidemia, diabetes, or complications thereof, or for increasing insulin sensitivity.

In some embodiments, provided herein is a compound of Formula (I), (II), (III), (IV), or (V), or a pharmaceutically acceptable salt thereof, or a pharmaceutical composition comprising the compound, for use in treating or preventing insulin resistance, a metabolic syndrome, hypercholesterolemia, atherogenic dyslipidemia, diabetes, or complications thereof, or for increasing insulin sensitivity.

In some embodiments, provided herein are uses of a compound of Formula (I), (II), (III), (IV), or (V), or a pharmaceutically acceptable salt thereof, or a pharmaceutical composition comprising the compound, for the preparation of a medicament for treating or preventing a neurological or neurodegenerative disorder.

In some embodiments, provided herein is a compound of Formula (I), (II), (III), (IV), or (V), or a pharmaceutically acceptable salt thereof, or a pharmaceutical composition comprising the compound, for use in treating or preventing a neurological or neurodegenerative disorder.

In some embodiments, provided herein are uses of a compound of Formula (I), (II), (III), (IV), or (V), or a pharmaceutically acceptable salt thereof, or a pharmaceutical composition comprising the compound, for the preparation of a medicament for the treatment or prevention of a mitochondrial-related disease or condition.

In some embodiments, provided herein is a compound of Formula (I), (II), (III), (IV), or (V), or a pharmaceutically acceptable salt thereof, or a pharmaceutical composition comprising the disclosed compound, for use in treating or preventing a mitochondrial-related disease or condition.

Pharmaceutical Compositions and Administration Thereof

The compositions and methods disclosed herein may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a disclosed compound and a pharmaceutically acceptable carrier.

Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection, or the like. The composition can also be present in a transdermal delivery system, e.g., a skin patch. The composition can also be present in a solution suitable for topical administration, such as an ointment or cream.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary, or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697, and 2005/004074; and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to about 99.5% (more preferably, about 0.5 to about 90.0%) of active ingredient in combination with a pharmaceutically acceptable carrier.

In some embodiments of the invention, a compound of the invention is conjointly administered with one or more additional compounds/agents. In certain such embodiments, the one or more additional agents are selected from PPAR agonists and antagonists, AMPK activators, PARP inhibitors, SIRT-activating compounds, CD38 inhibitors, and acetyl-CoA carboxylase inhibitors, and the pharmaceutically acceptable salts of these compounds.

In certain such embodiments, the conjoint administration is simultaneous. In certain such embodiments, the compound of the invention is co-formulated with the one or more additional compounds. In certain other such embodiments, the compound of the invention is administered separately but simultaneously with the one or more additional compounds. In certain such embodiments, the conjoint administration is sequential, with administration of the compound of the invention preceding or following the administration of the one or more additional compound by minutes or hours.

Methods of introduction of a compound of the invention may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. "Therapeutically effective amount" refers to the concentration of a compound that is sufficient to elicit the desired therapeutic effect. It is generally understood that the effective amount of the compound will vary according to the weight, sex, age, and medical history of the subject. Other factors that influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) *Harrison's Principles of Internal Medicine* 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six, or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, a week, or more of one another. Thus, an individual who receives such treatment can benefit from a combined effect of different therapeutic compounds.

This invention includes the use of pharmaceutically acceptable salts of compounds of the invention in the compositions and methods of the present invention. In certain embodiments, contemplated salts of the invention include, but are not limited to, alkyl, dialkyl, trialkyl, or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn, or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Exemplary pharmaceutically acceptable formulations of the compound of Formula (I), (II), (III), or (IV), and the preparations thereof, can be found in PCT Patent Publication No. WO 2015/186068, incorporated herein by reference.

The invention now being generally described, it will be more readily understood by reference to the following examples, which are included merely for purposes of illustration of certain aspects and embodiments of the present invention, and are not intended to limit the invention.

EXEMPLIFICATION

Chemical Synthesis

General Procedures $^1$H NMR and $^{13}$C NMR were recorded on a Bruker Avance III 300 (300 MHz, $^1$H; 75 MHz, $^{13}$C) with BBFO probe, Bruker Avance III 400 (400 MHz, $^1$H; 100 MHz, $^{13}$C) with BBFO probe with, or without, a Prodigy cryoprobe CPPBBO, Bruker Avance III 500 (500 MHz, $^1$H; 125 MHz, $^{13}$C) with a TBI probe or Bruker Avance III 600 (600 MHz, $^1$H; 150 MHz, $^{13}$C) with either a TBI probe or a TCI probe with Prodigy cryoprobe installed. Data was acquired and processed using TopSpin 3.2 software. Chemical shifts are expressed in parts per million (PPM) on the δ scale. Chemical shifts in CDCl$_3$ were referenced relative to CHCl$_3$ (7.26 ppm) for $^1$HNMR (Fulmer et al. *Organometallics* 2010, 29, 2176-2179).

HRMS were performed on an Orbitrap LTQ XL (Thermo Fisher Scientific, San Jose, Calif., USA) ion trap mass spectrometer using a nanospray (nano-electrospray) ionization source to generate ions from the analyte in solution. The instrument was calibrated with a standard calibration solution (as outlined in the instrument manual) on the day of analysis using direct infusion with the nanospray source. The instrument conditions were optimized for sensitivity on each compound of interest using LC tune software. The analysis was carried out in positive ion mode using the orbitrap FTMS analyser at a resolution of 100000. Samples, 5 μL, (1 μg/mL in methanol or acetonitrile), were injected with a glass syringe and inserted into the nanospray source. Ions generated were measured over the mass range 150 to 2000. Data was acquired in full scan mode over 60 seconds. Data was analyzed using the Qual Browser feature in Xcaliber 2.1 (Thermo Fisher Scientific, San Jose, Calif., USA).

Unless otherwise stated all reactions were performed in flame dried glassware under an atmosphere of dry argon. Reaction temperatures refer to the external bath temperature. Concentration of solvents was performed under reduced pressure on a rotary evaporator after which, residual solvent was removed under high vacuum (~0.1 mm/Hg).

Reagents and solvents were purchased from commercial sources and used without further purification, unless stated below. Reagents and solvents used in reactions were purified according to well established procedures (Perrin et al. *Purification of Laboratory Chemicals,* 3rd Edn. ed., Pergamon Press Ltd., Great Britain, 1988). In particular, methanol was distilled from magnesium and stored over 3 Å molecular sieves under argon. Triethylamine was distilled from calcium hydride immediately prior to use. Acetonitrile and dichloromethane were obtained from a PureSolv dry solvent system (Innovative Technology, Inc. model #PS-MD-7). Petroleum spirit used for chromatography consisted of the fraction 40-60° C.

Analytical thin layer chromatography was conducted on Merck, aluminium-backed silica plates 60 F$_{254}$ or silica gel 60 RP-C$_{18}$ F$_{254}$ plates and visualised using UV light and stained with a dip of either a ninhydrin, potassium permanganate, vanillin or phosphomolybdic acid solution.

Flash chromatography was routinely performed using either Grace Davison Discovery Sciences, Davisil LC60A 40-63 micron silica gel or Grace Davison Discovery Sciences, Davisil 633NC18E 35-70 micron reverse phase C$_{18}$ silica gel, following published guidelines (Still et al. *J. Org. Chem.* 1978, 43, 2923-2925). Compounds were dry loaded onto the column. Solvent was eluted using a Thomson SINGLE StEP pump at the flow rate recommended by the manufacturer (Thomson Instrument Company, Oceanside, Calif., USA). Deactivated silica gel was prepared by washing a column packed with silica gel with neat triethylamine (5 column volumes). After drying, the column was washed with n-hexane to remove any residual triethylamine. C$_{18}$ reverse phase silica gel was recycled after use by washing with four column volumes of each: DMSO, dichloromethane, methanol, methanol/0.1% TFA and water.

Example 1: Acylation of Diols

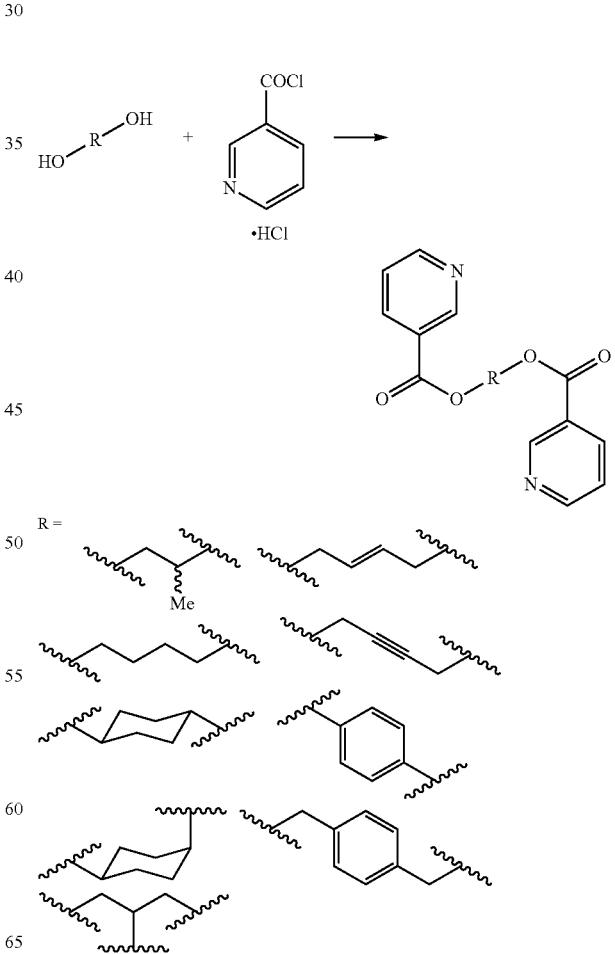

Nicotinoyl chloride hydrochloride (2.5 equiv.) was added portion-wise to a solution of diol (1 equiv.), triethylamine (5 equiv.) and 4-(dimethylamino)pyridine (5 mol %) in dichoromethane (1.0 M) at 0° C. The solution was stirred at 0° C. for 30 min. then, the cold bath was removed and the solution was stirred at room temperature for 18 h. The reaction mixture was diluted with saturated aqueous sodium bicarbonate solution (5-10× volume of solvent) and extracted with dichloromethane (3× solvent volume). The organic extracts were combined and washed with saturated aqueous sodium bicarbonate solution, water and brine then dried ($Na_2SO_4$). The solvent was removed under reduced pressure to afford the products.

*Note: the cis/trans-1,4-cyclohexanediol compounds were synthesized from a 50:50 mixture of the cis/trans-1,4-cyclohexanediol. The mixture of products could be easily separated by recrystallization from acetone, to afford the trans-isomer followed by flash chromatography on deactivated silica gel, eluting with 700% ethyl acetate/petroleum spirit, to afford the cis-isomer.

TABLE 1

| Compound | Characterization Data |
|---|---|
| 1A | Yield: 98 %<br><br>$^1$H NMR (400 MHz; $CDCl_3$) δ 1.49 (d, J = 6.5 Hz, 3H), 4.50 (dd, J = 12.1, 6.8 Hz, 1H), 4.59 (dd, J = 12.1, 3.4 Hz, 1H), 5.54-5.62 (m, 1H), 7.36-7.40 (m, 2H), 8.25-8.30 (m, 2H), 8.76-8.78 (m, 2H), 9.19 (d, J = 1.9 Hz, 1H), 9.21 (d, J = 1.9 Hz, 1H).<br><br>HRMS (ESI-MS) m/z calcd for $C_{14}H_{14}N_2O_4Na$ $(M + Na)^+$ 309.0851, found 309.0815. |
| 1B | Yield: 93 %<br><br>$^1$H NMR (400 MHz; $CDCl_3$) δ 1.95-1.98 (m, 4H), 4.42-4.45 (m, 4H), 7.39 (ddd, J = 8.0, 4.9, 0.9 Hz, 2H), 8.29 (ddd, J = 8.0, 2.3, 1.8 Hz, 2H), 8.77 (dd, J = 4.9, 1.8 Hz, 2H), 9.22 (dd, J = 2.3, 0.9 Hz, 2H).<br><br>HRMS (ESI-MS) m/z calcd for $C_{16}H_{16}N_2O_4Na$ $(M + Na)^+$ 323.1008, found 323.0992. |
| 1C | Yield: 38 %*<br><br>$^1$H NMR (400 MHz; $CDCl_3$) δ 1.90-1.98 (m, 4H), 2.02-2.11 (m, 4H), 5.19-5.24 (m, 2H), 7.42 (ddd, J = 7.9, 4.8, 0.9 Hz, 2H), 8.34 (ddd, J = 8.0, 2.2, 1.8 Hz, 2H), 8.79 (dd, J = 4.9, 1.8 Hz, 2H), 9.28 (dd, J = 2.2, 0.9 Hz, 2H).<br><br>HRMS (ESI-MS) m/z calcd for $C_{18}H_{18}N_2O_4Na$ $(M + Na)^+$ 349.1164, found 349.1151. |

TABLE 1-continued

| Compound | Characterization Data |
|---|---|
| 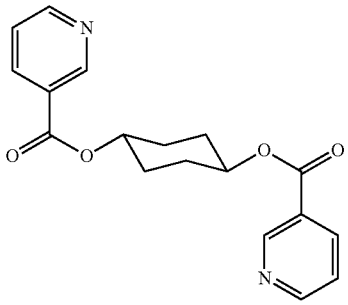<br>1D | Yield: 46 %*<br><br>¹H NMR (400 MHz; CDCl₃) δ 1.76-1.89 (m, 4H), 2.12-2.22 (m, 4H), 5.17-5.22 (m, 2H), 7.41 (ddd, J = 8.0, 4.9, 0.8 Hz, 2H), 8.31 (ddd, J = 8.0, 2.2, 1.8 Hz, 2H), 8.79 (dd, J = 4.9, 1.8 Hz, 2H), 9.24 (dd, J = 2.2, 0.8 Hz, 2H).<br><br>HRMS (ESI-MS) m/z calcd for $C_{18}H_{18}N_2O_4Na$ (M + Na)⁺ 349.1164, found 349.1150. |
| 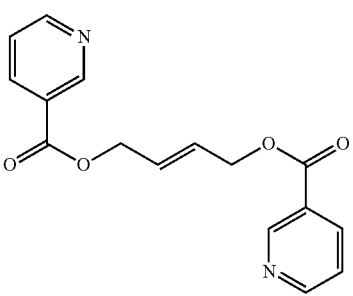<br>1E | Yield: 74 %<br><br>¹H NMR (400 MHz; CDCl₃) δ 4.91-4.92 (m, 4H), 8.08-8.10 (m, 2H), 7.43 (ddd, J = 8.0, 4.9, 0.8 Hz, 2H), 8.34 (ddd, J = 8.0, 2.1, 1.8 Hz, 2H), 8.80 (dd, J = 4.9, 1.8 Hz, 2H), 9.26 (dd, J = 2.1, 0.8 Hz, 2H).<br><br>HRMS (ESI-MS) m/z calcd for $C_{16}H_{14}N_2O_4Na$ (M + Na)⁺ 321.0851, found 321.0835. |
| 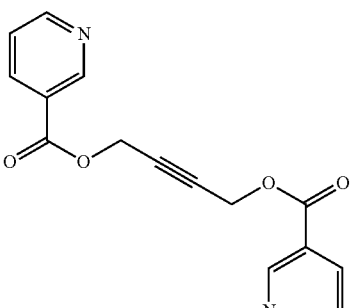<br>1F | Yield: 89 %<br><br>¹H NMR (400 MHz; CDCl₃) δ 5.02 (s, 4H), 8.08-8.10 (m, 2H), 7.41 (ddd, J = 8.0, 4.9, 0.8 Hz, 2H), 8.33 (ddd, J = 8.0, 2.1, 1.8 Hz, 2H), 8.80 (dd, J = 4.9, 1.8 Hz, 2H), 9.25 (dd, J = 2.1, 0.8 Hz, 2H).<br><br>HRMS (ESI-MS) m/z calcd for $C_{16}H_{12}N_2O_4Na$ (M + Na)⁺ 319.0695, found 319.0678. |
| 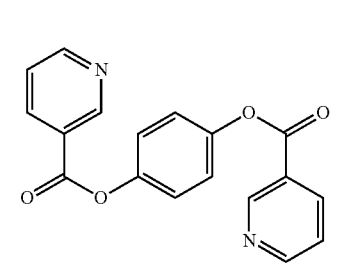<br>1G | Yield: 91 %<br><br>¹H NMR (400 MHz; CDCl₃) δ 7.33 (s, 4H), 7.51 (ddd, J = 8.0, 4.9, 0.8 Hz, 2H), 8.48 (ddd, J = 8.0, 2.1, 1.8 Hz, 2H), 8.88 (dd, J = 4.9, 1.8 Hz, 2H), 9.42 (dd, J = 2.1, 0.8 Hz, 2H).<br><br>HRMS (ESI-MS) m/z calcd for $C_{18}H_{12}N_2O_4Na$ (M + Na)⁺ 343.0695, found 343.0681. |

TABLE 1-continued

| Compound | Characterization Data |
|---|---|
| 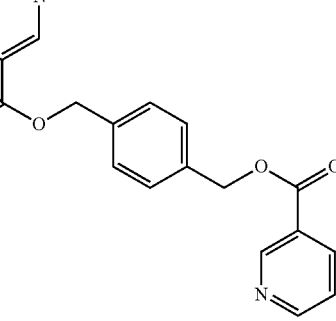<br>1H | Yield: 98 %<br><br>$^1$H NMR (400 MHz; CDCl$_3$) δ 5.41 (s, 4H), 7.43 (ddd, J = 8.1, 4.9, 0.8 Hz, 2H), 7.49 (s, 4H), 8.35 (ddd, J = 8.1, 2.1, 1.8 Hz, 2H), 8.79 (dd, J = 4.9, 1.8 Hz, 2H), 9.26 (dd, J = 2.1, 0.8 Hz, 2H).<br><br>HRMS (ESI-MS) m/z calcd for C$_{20}$H$_{16}$N$_2$O$_4$Na (M + Na)$^+$ 371.1008, found 371.0990. |
| 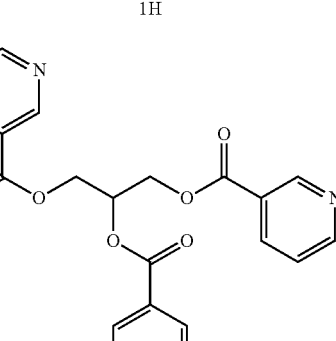<br>1I | Yield: 99%<br><br>$^1$H NMR (400 MHz; CDCl$_3$) δ 4.67 (dd, J = 12.2, 6.0 Hz, 2H), 4.77 (dd, J = 12.2, 4.2 Hz, 2H), 5.80-5.85 (m, 1H), 7.32-7.26 (m, 3H), 8.20-8.25 (m, 3H), 8.72-8.74 (m, 3H), 9.15 (d, J = 1.7 Hz, 2H), 9.17 (d, J = 1.7 Hz, 1H).<br><br>HRMS (ESI-MS) m/z calcd for C$_{21}$H$_{17}$N$_3$O$_6$Na (M + Na)$^+$ 430.1015, found 430.0952. |

Example 2: Ribosylation of Dipyridines

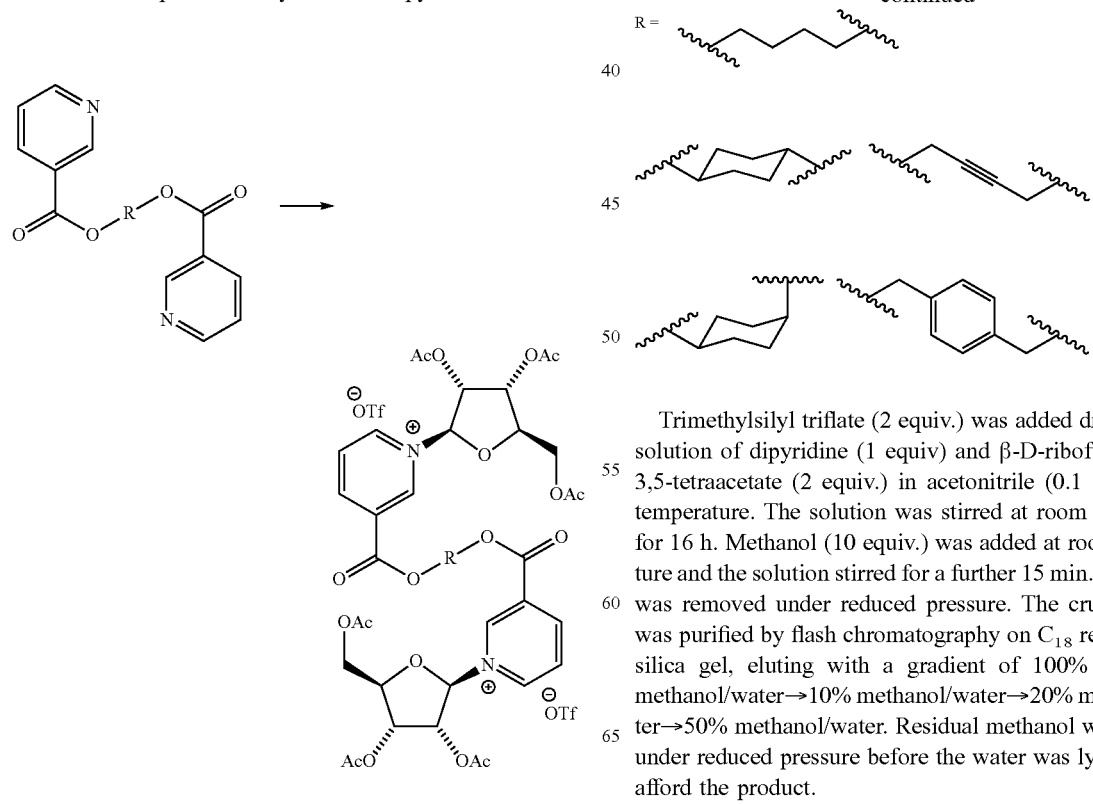

Trimethylsilyl triflate (2 equiv.) was added dropwise to a solution of dipyridine (1 equiv) and β-D-ribofuranose-1,2,3,5-tetraacetate (2 equiv.) in acetonitrile (0.1 M) at room temperature. The solution was stirred at room temperature for 16 h. Methanol (10 equiv.) was added at room temperature and the solution stirred for a further 15 min. The solvent was removed under reduced pressure. The crude material was purified by flash chromatography on C$_{18}$ reverse phase silica gel, eluting with a gradient of 100% water→5% methanol/water→10% methanol/water→20% methanol/water→50% methanol/water. Residual methanol was removed under reduced pressure before the water was lyophilised to afford the product.

TABLE 2

| Compound | Characterization Data |
|---|---|
| 2B | Yield: 30 %<br><br>¹H NMR (400 MHz; MeOD) δ 2.03-2.09 (m, 4H), 2.14 (s, 6H), 2.15 (s, 6H), 2.19 (s, 6H), 4.50 (dd, J = 12.9, 2.6 Hz, 2H), 4.57-4.61 (m, 6H), 4.81-4.83 (m, 2H), 4.43 (dd, J = 6.0, 5.5 Hz, 2H), 5.59 (dd, J = 5.5, 3.7 Hz, 2H), 6.62 (d, J = 3.7 Hz, 2H), 9.20-9.22 (m, 2H), 9.35-9.38 (m, 2H), 9.64-9.65 (m, 2H).<br><br>HRMS (ESI-MS) m/z calcd for $C_{38}H_{56}N_2O_{18}$ (M)⁺⁺ 409.1367, found 409.1357. |
| 2C | Yield: 23 %<br><br>¹H NMR (300 MHz; MeOD) δ 2.02-2.09 (m, 4H), 2.14-2.21 (m, 22H), 4.51 (dd, J = 13.2, 2.6 Hz, 2H), 4.60 (dd, J = 13.2, 3.4 Hz, 2H), 4.82-4.84 (m, 2H), 5.29-5.35 (m, 2H), 5.45 (dd, J = 5.8, 5.2 Hz, 2H), 5.59-5.62 (m, 2H), 6.64 (d, J = 3.7 Hz, 2H), 8.37-8.42 (m, 2H), 9.24-9.27 (m, 2H), 9.36-9.39 (m, 2H), 9.66-9.67 (m, 2H).<br><br>HRMS (ESI-MS) m/z calcd for $C_{40}H_{48}N_2O_{28}$ (M)⁺⁺ 422.1446, found 422.1436. |
| 2D | Yield: 27 %<br><br>¹H NMR (400 MHz; MeOD) δ 1.92-1.97 (m, 4H), 2.15 (s, 6H), 2.18 (s, 6H), 2.21 (s, 6H), 2.26-2.31 (m, 4H), 4.51 (dd, J = 13.1, 2.6 Hz, 2H), 4.61 (dd, J = 13.2, 3.4 Hz, 2H), 4.82-4.85 (m, 2H), 5.32-5.37 (m, 2H), 5.43 (dd, J = 6.1, 5.6 Hz, 2H), 5.60 (dd, J = 5.6, 3.5 Hz, 2H), 6.64 (d, J = 3.5 Hz, 2H), 8.39 (dd, J = 7.9, 6.2 Hz, 2H), 9.22-9.24 (m, 2H), 9.37-9.39 (m, 2H), 9.67-9.68 (m, 2H).<br><br>HRMS (ES1-MS) m/z calcd for $C_{40}H_{48}N_2O_{18}$ (M)⁺⁺ 422.1446, found 422.1437. |

TABLE 2-continued
| Compound | Characterization Data |
|---|---|
| 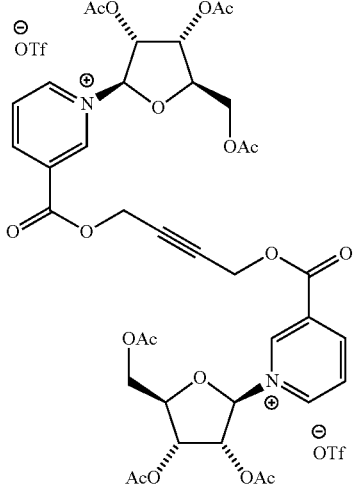  2F | Yield: 19%<br><br>$^1$H NMR (300 MHz; MeOD) δ 2.15 (s, 6H), 2.17 (s, 6H), 2.19 (s, 6H), 4.49 (dd, J = 13.1, 2.5 Hz, 2H), 4.59 (dd, J = 13.1, 3.1 Hz, 2H), 4.81-4.85 (m, 2H), 5.22 (s, 4H), 5.44 (dd, J = 5.7, 5.1 Hz, 2H), 5.59 (dd, J = 5.3, 3.8 Hz, 2H), 6.62 (d, J = 3.8 Hz, 2H), 8.40 (dd, J = 8.0, 6.4 Hz, 2H), 9.20-9.24 (m, 2H), 9.38-9.40 (m, 2H), 9.66-9.67 (m, 2H). HRMS (ESI-MS) m/z calcd-for $C_{38}H_{42}N_2O_{18}$ (M)$^{++}$ 407.1211, found 407.1201. |
| 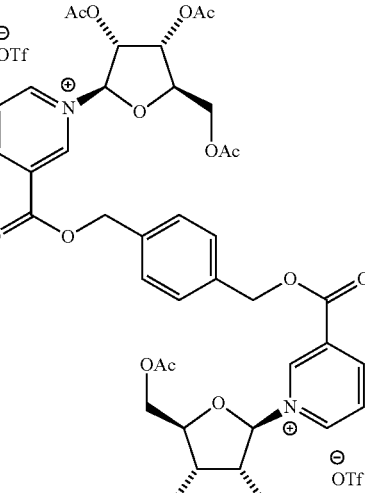  2H | Yield: 19%[1]<br><br>H NMR (300 MHz; MeOD) δ 2.01 (s, 6H), 2.13 (s, 6H), 2.17 (s, 6H), 4.42 (dd, J = 13.1, 2.5 Hz, 2H), 4.57 (dd, J = 13.1, 3.1 Hz, 2H), 4.79-4.85 (m, 2H), 5.36-5.40 (m, 2H), 5.51-5.56 (m, 6H), 6.60 (d, J = 3.6 Hz, 2H), 8.35-8.40 (m, 2H), 9.21-9.24 (m, 2H), 9.35-9.37 (m, 2H), 9.65-9.67 (m, 2H). HRMS (ESI-MS) m/z calcd for $C_{42}H_{46}N_2O_{18}$ (M)$^{++}$ 433.1367, found 433.1360. |

Example 3: Reduction of Dipyridinium Compounds

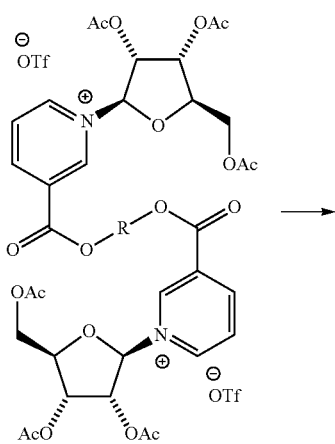

→

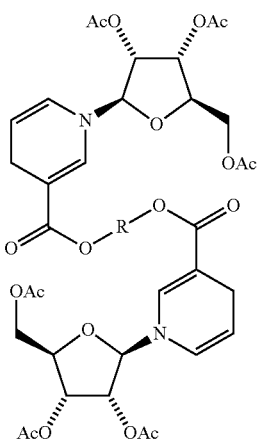

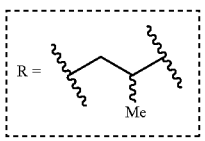

Sodium bicarbonate (12 equiv.) and sodium dithionite (5 equiv.) were added successively as solids to a solution of dipyridinium triflate (1 equiv.) in water (0.2 M) and acetonitrile (0.2 M) at room temperature. The solution was stirred at room temperature for 18 hours. The mixture was diluted with water (10 solvent volumes; 70% ethyl acetate/petroleum spirit) and extracted with ethyl acetate (3× solvent volume). The organic extracts were combined and dried ($Na_2SO_4$). The solvent was removed under reduced pressure and the crude material purified by flash chromatography on deactivated silica gel, eluting with an ethyl acetate/petroleum spirit mixture.

TABLE 3

| Compound | Characterization Data |
|---|---|
| 3A | Yield: 68 %<br><br>$^1$H NMR (300 MHz; MeOD) δ 1.26 (d, J = 6.5 Hz, 3H), 1.27 (d, J = 6.5 Hz, 3H), 2.08 (s, 6H), 2.10 (s, 6H), 2.13 (s, 6H), 3.02-3.04 (m, 4H), 4.16-4.34 (m, 8H), 4.88-4.92 (m, 2H), 5.04-5.08 (m, 2H), 5.16-5.27 (m, 6H), 6.02-6.05 (m, 2H), 7.25-7.27 (m, 2H).<br><br>HRMS (ESI-MS) m/z calcd for $C_{37}H_{46}N_2O_{18}Na$ (M + Na)$^+$ 829.2643, found 829.2576. |

Example 4: Pharmacokinetic/Pharmacodynamic Duration of Effect Study of Transcyclohexyl NaR Dimer Following a Single Oral Gavage Dose Administration to C57BL/6 Mice Transcyclohexyl nicotinic acid riboside (NaR) dimer was administered by oral gavage at a dose of 500 mg/kg in an Ethanol/PBS, pH 7.4/PEG400 (10/30/60) vehicle. The dosing volume was 5 ml/kg at a solution concentration of 100 mg/ml. The solution concentration was increased for the presence of counterion.

Animals were fasted for 16 hours prior to dosing. Samples were collected pre-dose and at 0.25, 0.75, 1, 2, 4, 8 and 24 hr post dosing. Following euthanasia, the entire liver and skeletal muscle (gastrocnemius with attached soleus muscle, bilateral) were rinsed with 0.9% saline, and frozen for later bioanalysis. Samples were maintained frozen at −80° C. until bioanalysis.

Samples were thawed, homogenized, extracted and analyzed by LC-MS on the same day. The LC used was a Shimadzu Nexera UPLC, and the mass spectrometer was an AB Sciex Qtrap 6500. Specimens were analyzed for levels of administered compound (transcyclohexyl NaR dimer), as well as for levels of NAD, NAAD, NAM, and NMN by the method of standard addition, to detect alterations from the basal levels of the analytes. Calibration standards for quantifying administered compound were prepared using transcyclohexyl NaR dimer in mouse liver or skeletal muscle homogenates. Corresponding standards for quantifying other metabolites were also prepared. Data are calculated as the mean concentration from n=6 animals per time point.

Table 4 shows the concentration (mmol/kg) of the analytes over time in C57BL/6 Mouse Mouse Skeletal Muscle.

TABLE 4

| | Analyte | | | | |
|---|---|---|---|---|---|
| Time (hr) | transcyclohexyl NaR dimer (mmol/kg) | NAD (mmol/kg) | NAAD (mmol/kg) | NAM (mmol/kg) | NMN (mmol/kg) |
| 0 | BQL | 0.781 | BDL | 0.159 | 0.00225 |
| 0.25 | 0.0142 | 0.826 | BDL | 0.161 | 0.00200 |
| 0.75 | 0.000749 | 0.861 | BDL | 0.208 | 0.00196 |

TABLE 4-continued

| | | | | | |
|---|---|---|---|---|---|
| 1 | 0.00109 | 0.720 | BDL | 0.184 | 0.00173 |
| 2 | BQL | 0.875 | BDL | 0.0918 | 0.00191 |
| 4 | BQL | 0.726 | 0.0101 | 0.166 | 0.00222 |
| 8 | BQL | 0.648 | 0.0128 | 0.170 | 0.00245 |
| 24 | BQL | 0.635 | BDL | 0.155 | 0.00199 |

| | transcyclohexyl NaR dimer (g/mol) | NAD (g/mol) | NAAD (g/mol) | NAM (g/mol) | NMN (g/mol) |
|---|---|---|---|---|---|
| Mol. Weight | 844.82 | 663.4 | 664.4 | 122.1 | 334.2 |

BQL—Below quantitation limit
BDL—Below Detection Limit, No Peak Detected

Table 5 shows the concentration (g/g) of the analytes over time in C57BL/6 mouse skeletal muscle. FIG. 1 illustrates this data in graphical form.

TABLE 5

| | Analyte | | | | |
|---|---|---|---|---|---|
| Time (hr) | transcyclohexyl NaR dimer (µg/g) | NAD (µg/g) | NAAD (µg/g) | NAM (µg/g) | NMN (µg/g) |
| 0 | BQL | 518 | BDL | 19.4 | 0.752 |
| 0.25 | 12.0 | 548 | BDL | 19.7 | 0.667 |
| 0.75 | BQL | 571 | BDL | 25.3 | 0.656 |
| 1 | 0.921 | 478 | BDL | 22.4 | 0.579 |
| 2 | BQL | 581 | BDL | 11.2 | 0.639 |
| 4 | BQL | 482 | 6.72 | 20.2 | 0.740 |
| 8 | BQL | 430 | 8.52 | 20.8 | 0.818 |
| 24 | BQL | 421 | BDL | 18.9 | 0.665 |

BQL—Below quantitation limit
BDL—Below Detection Limit, No Peak Detected

Table 6 shows the pharmacokinetic parameters of analyte in C57BL/6 mouse skeletal muscle.

TABLE 6

| | | Analyte | | | | |
|---|---|---|---|---|---|---|
| | | trans-cyclohexyl NaR dimer | NAD | NAAD | NAM | NMN |
| $AUC_{(0-x)}$ | µg · h/g | ND | 10765 | ND | 469 | 17.6 |
| $AUC_{(0-\infty)}$ | µg · h/g | ND | 91837 | ND | 5103 | 69.0 |
| % AUC Extrap | % | ND | 88.3 | ND | 90.8 | 74.5 |
| Cmax | µg/g | ND | 581 | ND | 25.3 | 0.818 |
| tmax | h | ND | 2.00 | ND | 0.750 | 8.00 |
| t½ | h | ND | 133 | ND | 170 | 53.6 |
| Regression Points | | ND | 4, 8, 24 | ND | 4, 8, 24[a] | 8, 24[b] |

[a]Although the concentration data for the time points selected for the regression line used to calculate PK parameters do not sequentially decline with time, the formed line has a negative/descending slope.
[b]Only 2 time points were selected for the regression line used to calculate PK parameters as these were the only ones available in the apparent terminal phase of the time-concentration curve.
ND = not determined Table 7 shows the concentration (mmol/kg) of the analytes over time in C57BL/6 mouse liver.

TABLE 7

| | Analyte | | | | |
|---|---|---|---|---|---|
| Time (hr) | transcyclohexyl NaR dimer (mmol/kg) | NAD (mmol/kg) | NAAD (mmol/kg) | NAM (mmol/kg) | NMN (mmol/kg) |
| 0 | BQL | 1.08 | BDL | 0.430 | 0.00637 |
| 0.25 | 0.0125 | 0.938 | BDL | 0.481 | 0.00556 |
| 0.75 | 0.000387 | 0.493 | BDL | 1.69 | 0.00977 |
| 1 | 0.000275 | 0.575 | BDL | 1.48 | 0.00945 |
| 2 | 0.0000706 | 1.19 | 0.0294 | 0.660 | 0.00706 |
| 4 | BQL | 2.23 | 0.206 | 0.791 | 0.0146 |
| 8 | BQL | 4.92 | 0.125 | 0.609 | 0.0250 |
| 24 | BQL | 1.10 | BDL | 0.381 | 0.00459 |

| | transcyclohexyl NaR dimer (g/mol) | NAD (g/mol) | NAAD (g/mol) | NAM (g/mol) | NMN (g/mol) |
|---|---|---|---|---|---|
| Mol. Weight | 844.82 | 663.4 | 664.4 | 122.1 | 334.2 |

BQL—Below quantitation limit
BDL—Below Detection Limit, No Peak Detected

Figure 2:
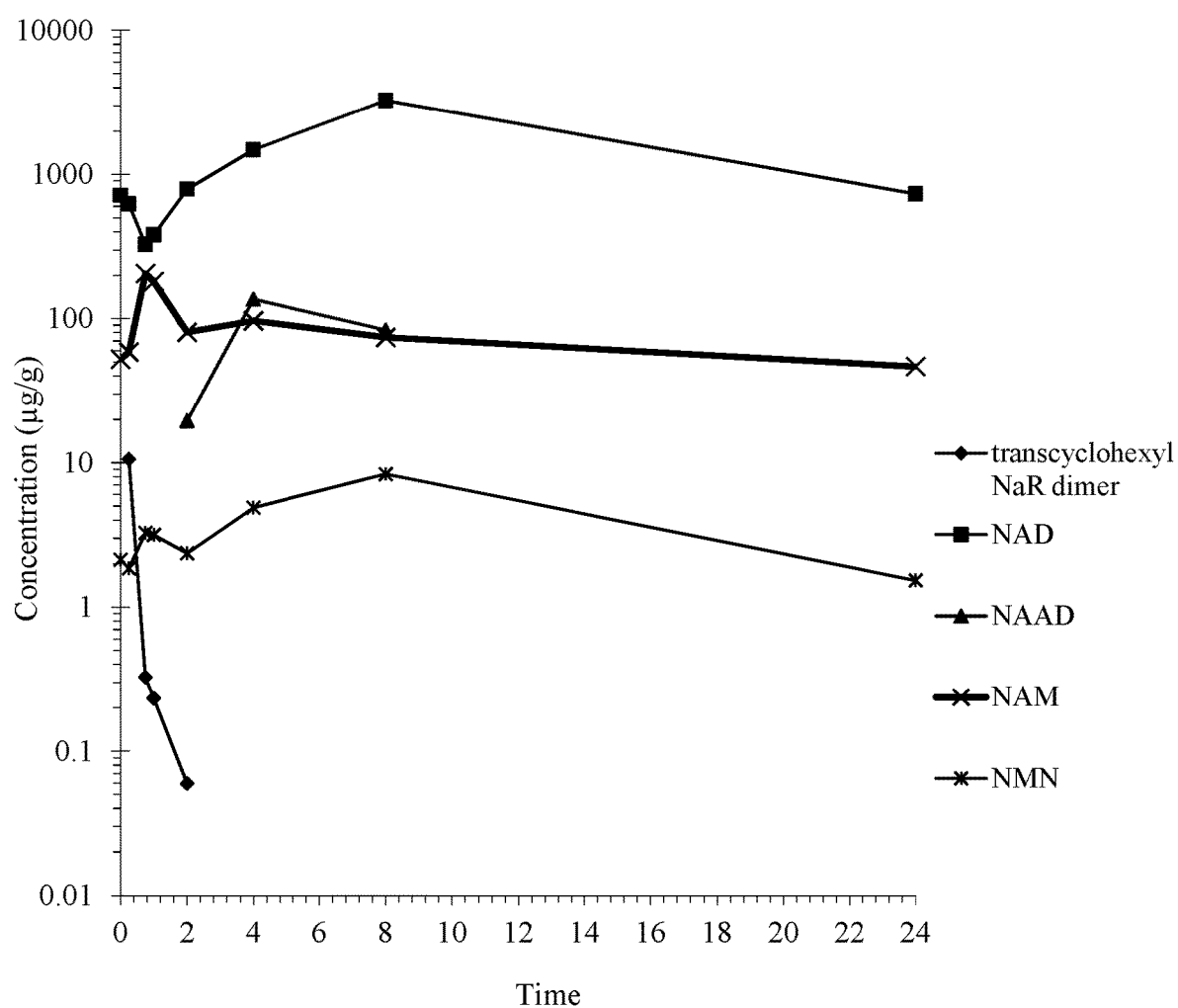
FIG. 2 depicts summary liver concentrations of transcyclohexyl NaR dimer, NAD, NAAD, NAM, and NMN following 500 mg/kg oral gavage administration of transcyclohexyl NaR dimer.

Table 8 shows the concentration (µg/g) of the analytes over time in C57BL/6 mouse liver. FIG. 2 illustrates this data in graphical form.

TABLE 8

| | Analyte | | | | |
|---|---|---|---|---|---|
| Time (hr) | transcyclohexyl NaR dimer (µg/g) | NAD (µg/g) | NAAD (µg/g) | NAM (µg/g) | NMN (µg/g) |
| 0 | BQL | 713 | BDL | 52.5 | 2.13 |
| 0.25 | 10.567 | 623 | BDL | 58.7 | 1.86 |
| 0.75 | 0.327 | 327 | BDL | 206 | 3.26 |
| 1 | 0.232 | 381 | BDL | 181 | 3.16 |
| 2 | 0.060 | 787 | 19.5 | 80.6 | 2.36 |
| 4 | BQL | 1478 | 137 | 96.5 | 4.87 |
| 8 | BQL | 3267 | 83.3 | 74.3 | 8.34 |
| 24 | BQL | 731 | BDL | 46.6 | 1.53 |

BQL—Below quantitation limit
BDL—Below Detection Limit, No Peak Detected

Table 9 shows the pharmacokinetic parameters of analyte in C57BL/6 mouse liver.

TABLE 9

| | | Analyte | | | | |
|---|---|---|---|---|---|---|
| | | trans-cyclohexyl NaR dimer | NAD | NAAD | NAM | NMN |
| $AUC_{(0-x)}$ | µg · h/g | 3.05 | 39921 | ND | 1719 | 103 |
| $AUC_{(0-\infty)}$ | µg · h/g | 3.05 | 47729 | ND | 3075 | 118 |
| % AUC Extrap | % | 0.00 | 16.4 | ND | 44.1 | 12.3 |
| Cmax | µg/g | 10.57 | 3267 | ND | 206 | 8.34 |
| tmax | h | 0.250 | 8.00 | ND | 0.750 | 8.00 |
| t½ | h | 0.509 | 7.40 | ND | 20.2 | 6.55 |
| Regression Points | h | 0.75, 1, 2 | 8, 24[a] | ND | 4, 8, 24 | 8, 24[a] |

[a]Only 2 time points were selected for the regression line used to calculate PK parameters as these were the only ones available in the apparent terminal phase of the time-concentration curve.
ND = not determined

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:
1. A compound having a structure of Formula (I):

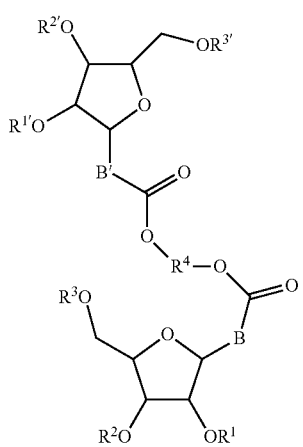

(I)

or a pharmaceutically acceptable salt thereof, wherein:
B and B' are each, independently

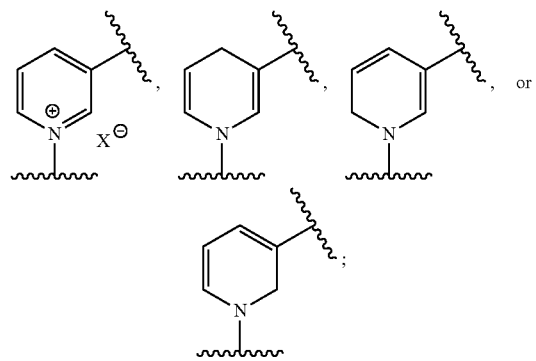

$X^-$ is a counteranion;
$R^1$, $R^2$, $R^3$, $R^{1'}$, $R^{2'}$, and $R^{3'}$ are each independently hydrogen, substituted or unsubstituted alkyl, or substituted or unsubstituted —C(O)-alkyl;
$R^4$ is $C_1$-$C_6$-alkylene, $C_2$-$C_6$-alkenylene, $C_2$-$C_6$-alkynylene, $C_3$-$C_6$-cycloalkylene, $C_3$-$C_6$-cycloalkenylene, arylene, heterocyclylene, heteroarylene, or heteroaryl-$C_2$-$C_6$-alkylene, each of which is unsubstituted or substituted with one or more substituents selected from halo, OH, $NO_2$, CN, $C_1$-$C_4$-alkyl, $C_1$-$C_4$-alkoxy, —C(O)—$C_1$-$C_4$-alkyl, —C(O)-aryl, —C(O)-heteroaryl, —OC(O)—$C_1$-$C_4$-alkyl, —OC(O)-aryl, —OC(O)-heteroaryl, —NR$^a$C(O)—$C_1$-$C_4$-alkyl, —NR$^a$C(O)-aryl, —NR$^a$C(O)-heteroaryl, aryl, and heteroaryl; and
$R^a$ is hydrogen or alkyl.

2. The compound of claim 1, wherein the compound has a structure of Formula (II):

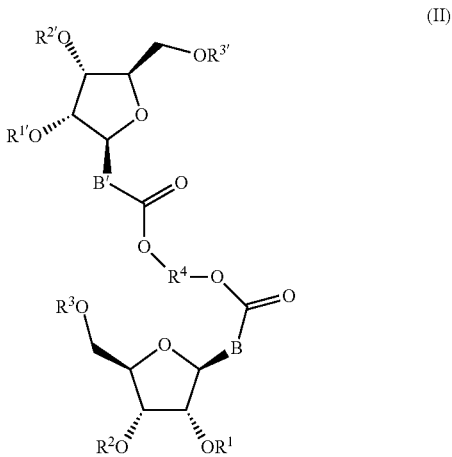

(II)

or a pharmaceutically acceptable salt thereof.

3. The compound of claim 1, wherein the compound has a structure of Formula (III):

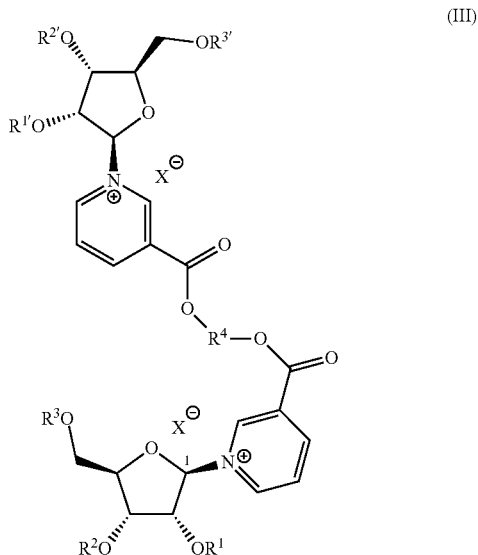

(III)

or a pharmaceutically acceptable salt thereof.

4. The compound of claim 1, wherein the compound has a structure of Formula (IV):

(IV)

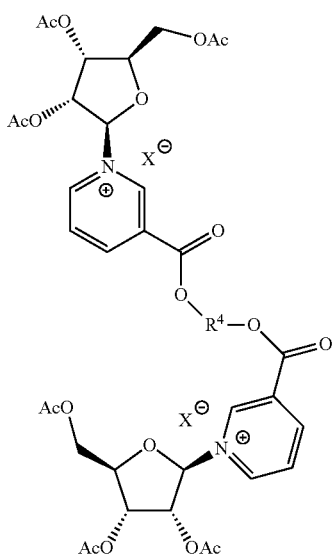

or a pharmaceutically acceptable salt thereof.

5. The compound of claim 1, wherein the compound has a structure of Formula (V):

(V)

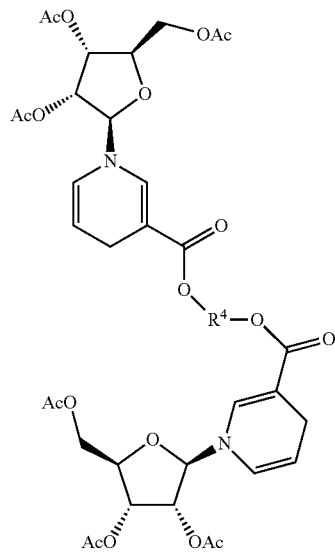

or a pharmaceutically acceptable salt thereof.

6. The compound of claim 1, wherein $R^4$ is a moiety of structural formula:

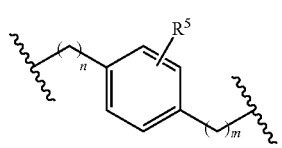

wherein $R^5$ is hydrogen, halo, OH, $NO_2$, CN, $C_1$-$C_4$-alkyl, $C_1$-$C_4$-alkoxy, —C(O)—$C_1$-$C_4$-alkyl, —C(O)-aryl, —C(O)-heteroaryl, —OC(O)—$C_1$-$C_4$-alkyl, —OC(O)-aryl, —OC(O)-heteroaryl, —NR$^a$C(O)—$C_1$-$C_4$-alkyl, —NR$^a$C(O)-aryl, —NR$^a$C(O)-heteroaryl, aryl, or heteroaryl; and m and n are each integers from 1 to about 6, wherein the value of m is independent of the value of n.

7. The compound of claim 1, wherein $R^4$ is selected from:

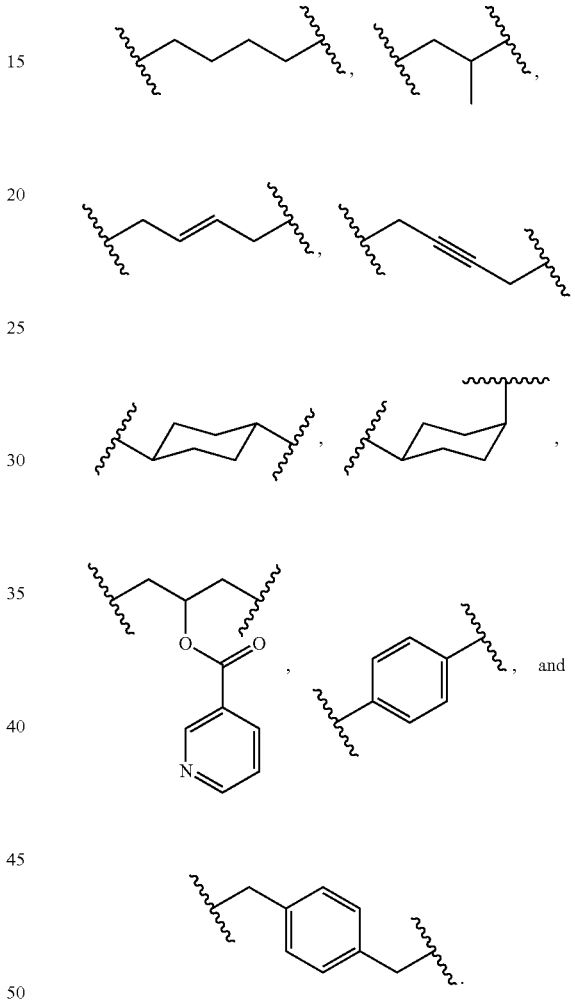

8. The compound of claim 1, wherein $R^4$ is heterocycloalkylene selected from monosaccharides, disaccharides, oligosaccharides, and polysaccharides, where the oxygen atoms attached to $R_4$ are oxygen atoms of the monosaccharide, disaccharide, oligosaccharide, or polysaccharide in its unbound form.

9. The compound of claim 1, wherein each $X^-$ is independently selected from $Cl^-$, $OH^-$, $SO_4H^-$, $HPO_4^{2-}$, $CH_3COO^-$, $CF_3COO^-$, $PF_6^-$, $CH_3SO_3^-$, $CF_3SO_3^-$, and $PhCO_2^-$.

10. The compound of claim 1, wherein each $X^-$ is $CF_3SO_3^-$.

11. The compound of claim 1, wherein the compound is selected from:

-continued
(2AA)
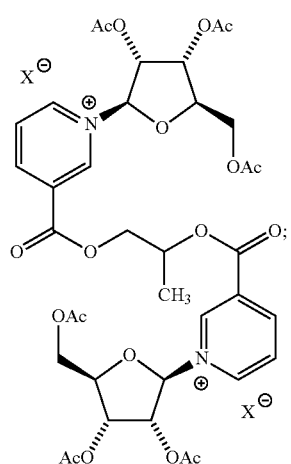
(2DD)
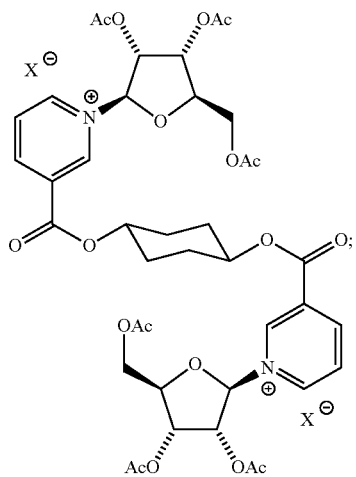
(2BB)
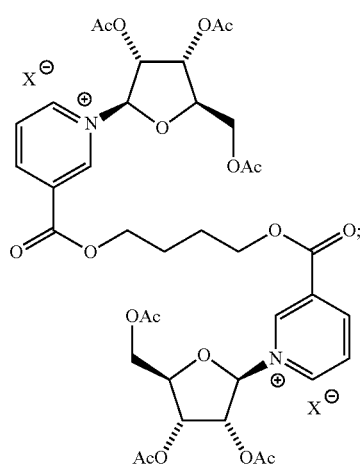
(2EE)
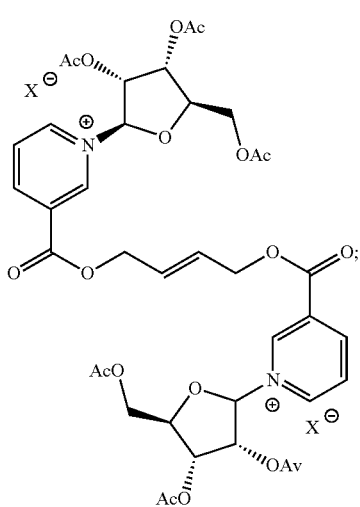
(2CC)
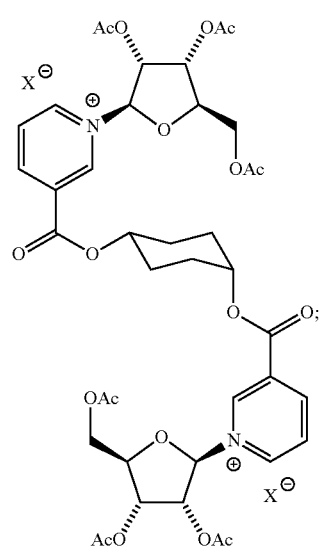
(2FF)
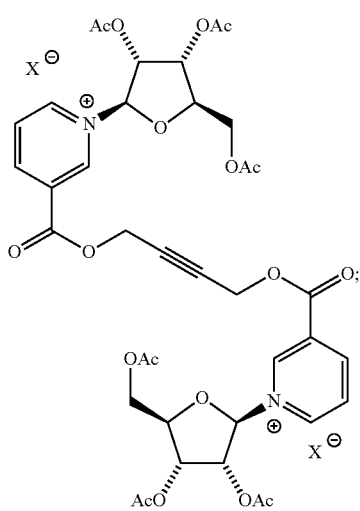

-continued
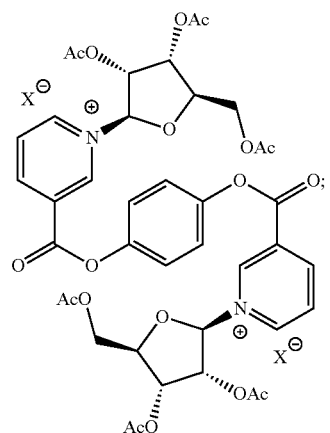
(2GG)
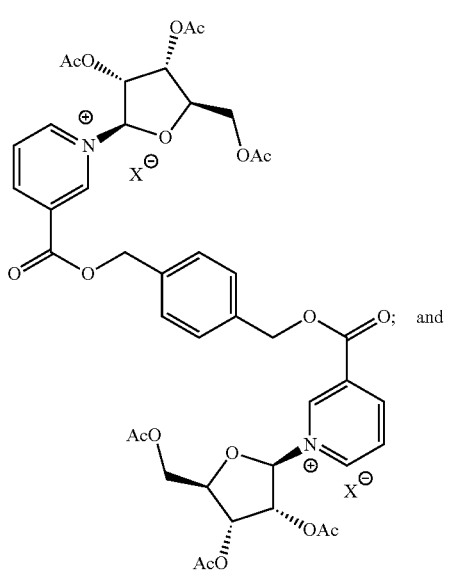
(2HH)
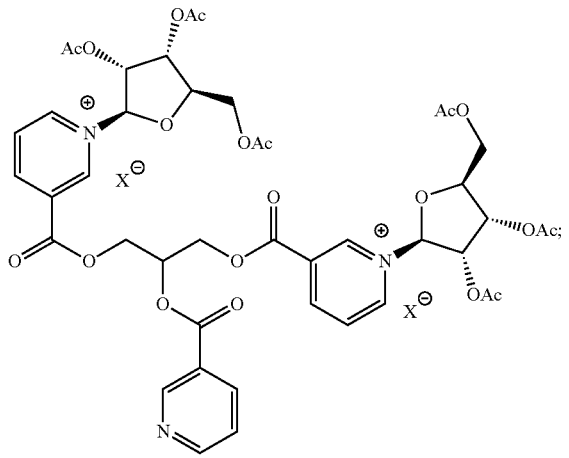
(2II)
or a pharmaceutically acceptable salt thereof.
12. The compound of claim 1, wherein the compound is selected from:
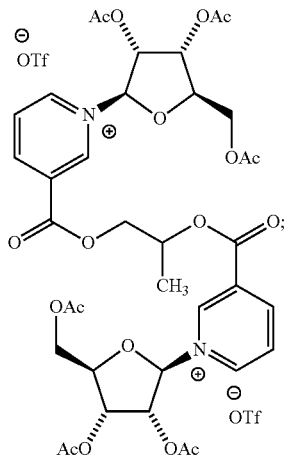
(2A)
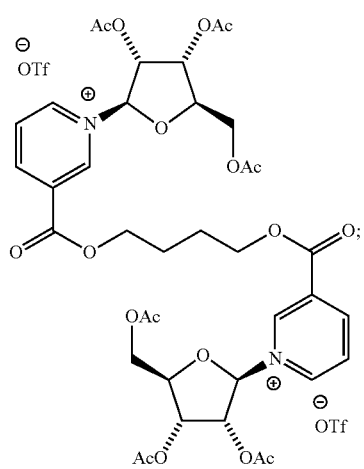
(2B)
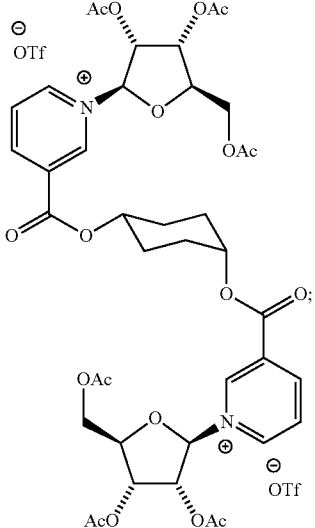
(2C)

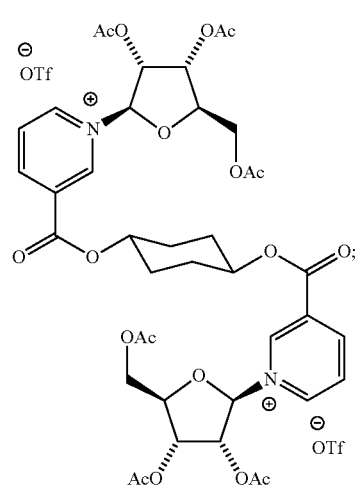
(2D)
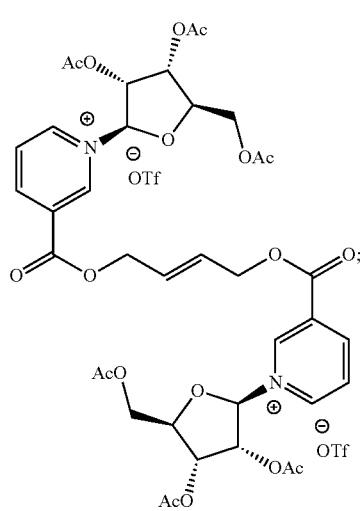
(2E)
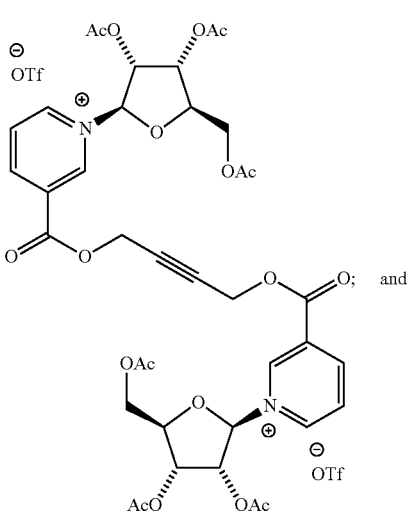
(2F)
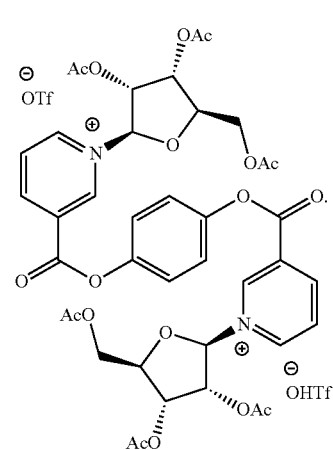
(2G)
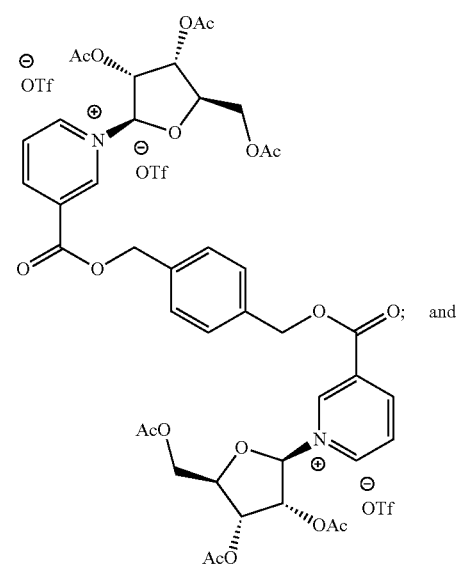
(2H)
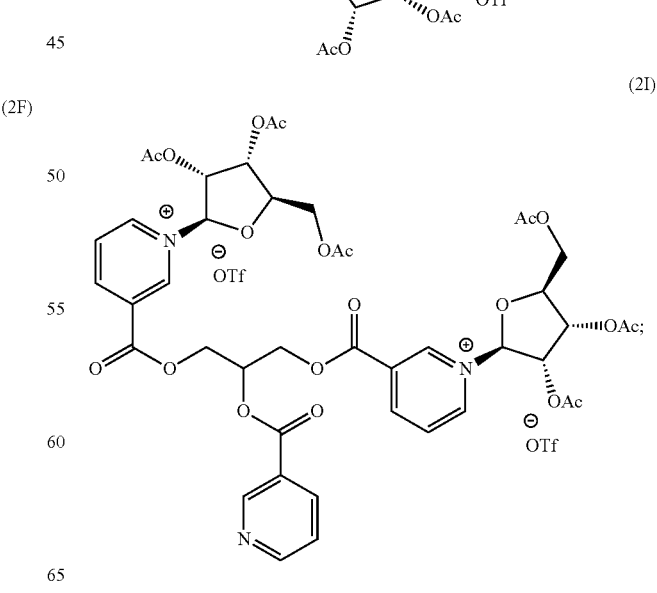
(2I)
or a pharmaceutically acceptable salt thereof.

13. The compound of claim 1, wherein the compound is selected from:
(3A)
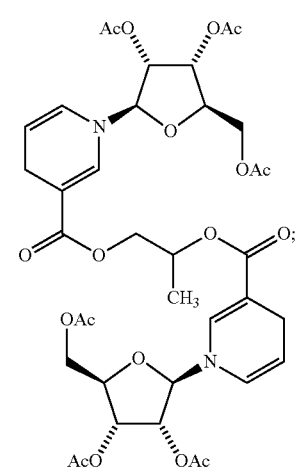
(3B)
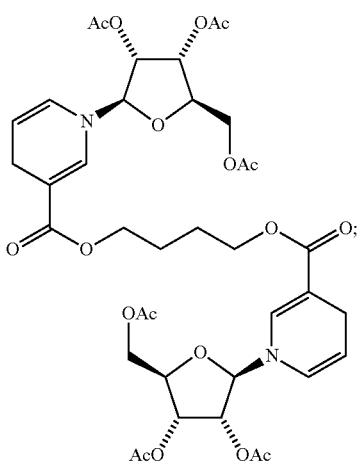
(3C)
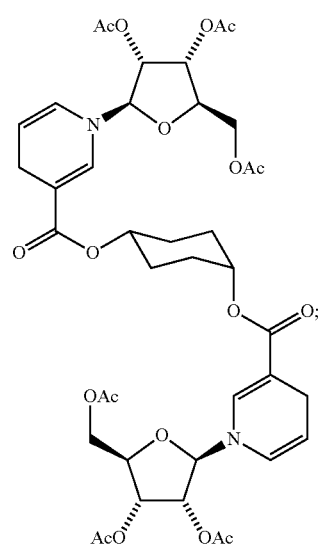
-continued
(3D)
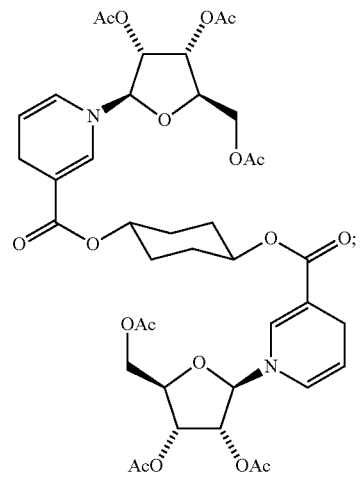
(3E)
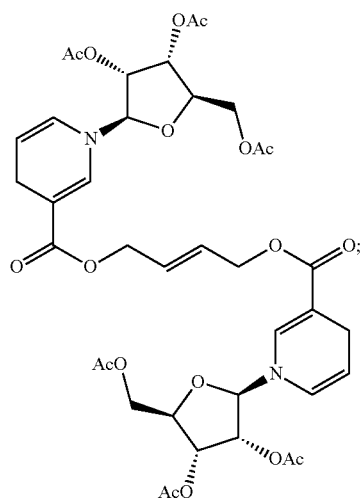
(3F)
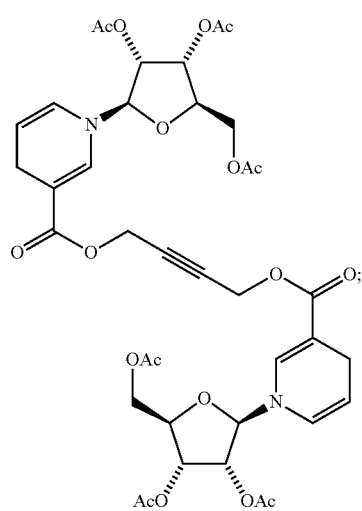

(3G)

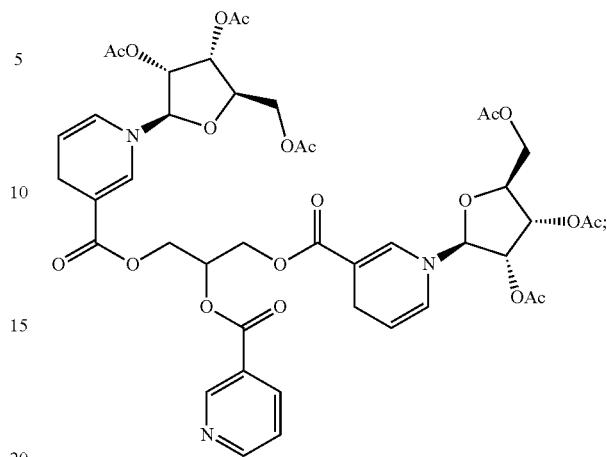

(3I)

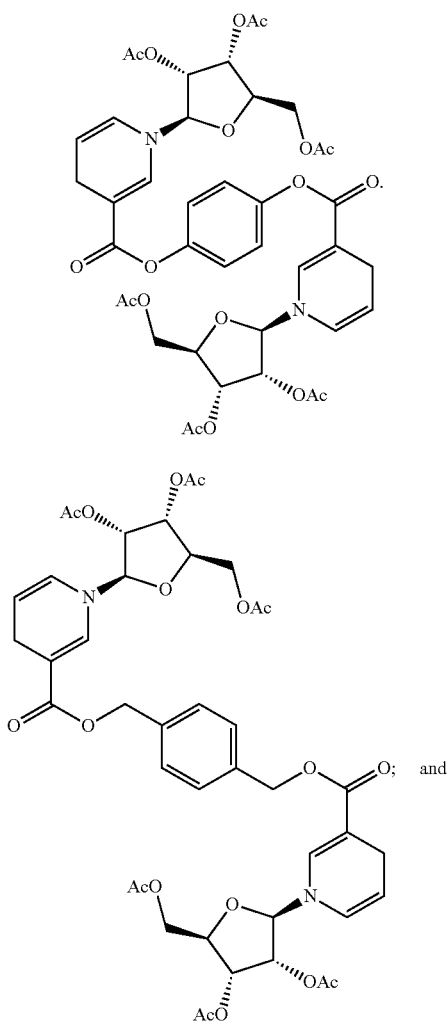

(3H)

or a pharmaceutically acceptable salt thereof.

14. A pharmaceutical composition comprising a compound of claim 1 or a pharmaceutically acceptable salt thereof and a pharmaceutically acceptable carrier or excipient.

15. A method for promoting survival of a eukaryotic cell, comprising contacting the cell with a compound of claim 1 or a pharmaceutically acceptable salt thereof.

16. A method for treating insulin resistance, a metabolic syndrome, hypercholesterolemia, atherogenic dyslipidemia, diabetes, or complications thereof, or for increasing insulin sensitivity in a subject, comprising administering to a subject in need thereof a compound of claim 1 or a pharmaceutically acceptable salt thereof.

17. A method for treating a neurological or neurodegenerative disorder in a subject, comprising administering to a subject in need thereof of a compound according to claim 1 or a pharmaceutically acceptable salt thereof.

18. The method of claim 16, wherein the subject is human.

19. The method of claim 17, wherein the subject is human.

\* \* \* \* \*